United States Patent
Kuracina et al.

(10) Patent No.: US 10,413,712 B1
(45) Date of Patent: Sep. 17, 2019

(54) LUER-ACTIVATED VALVES

(71) Applicant: Injectimed, Inc., Minden, NV (US)

(72) Inventors: Thomas C. Kuracina, Carson City, NV (US); Andy Narvaez-Nunez, Las Vegas, NV (US)

(73) Assignee: INJECTIMED, INC., Minden, NV (US)

( * ) Notice: Subject to any disclaimer, the term of this patent is extended or adjusted under 35 U.S.C. 154(b) by 0 days.

(21) Appl. No.: 16/289,223

(22) Filed: Feb. 28, 2019

(51) Int. Cl.
| | |
|---|---|
| *A61M 39/06* | (2006.01) |
| *A61M 25/00* | (2006.01) |
| *A61M 25/06* | (2006.01) |
| *A61M 39/02* | (2006.01) |

(52) U.S. Cl.
CPC ........ *A61M 39/06* (2013.01); *A61M 25/0097* (2013.01); *A61M 25/0606* (2013.01); *A61M 2039/027* (2013.01); *A61M 2039/0258* (2013.01); *A61M 2039/0282* (2013.01); *A61M 2039/062* (2013.01); *A61M 2039/0633* (2013.01)

(58) Field of Classification Search
CPC ...... A61M 39/06; A61M 39/24; A61M 39/26; A61M 25/007; A61M 25/0606; A61M 2039/027; A61M 2039/062; A61M 2039/0633; A61M 2039/0673
See application file for complete search history.

(56) References Cited

U.S. PATENT DOCUMENTS

| | | | | |
|---|---|---|---|---|
| 2008/0108944 | A1* | 5/2008 | Woehr | A61B 5/1411 604/164.08 |
| 2011/0240158 | A1* | 10/2011 | Py | A61M 39/18 137/614 |
| 2015/0045771 | A1* | 2/2015 | Hayakawa | A61M 5/3202 604/507 |
| 2017/0080200 | A1* | 3/2017 | Bickhart | A61M 39/0606 |
| 2018/0338778 | A1* | 11/2018 | Main | A61B 17/3417 |
| 2019/0030314 | A1* | 1/2019 | Sumanasinghe | A61M 39/28 |
| 2019/0070401 | A1* | 3/2019 | Merritt | A61M 39/0613 |
| 2019/0076640 | A1* | 3/2019 | Bhatnagar | A61M 39/0613 |

* cited by examiner

*Primary Examiner* — Laura A Bouchelle
*Assistant Examiner* — Dung T Ulsh
(74) *Attorney, Agent, or Firm* — Edell, Shapiro & Finnan, LLC

(57) ABSTRACT

Luer activated valves are disclosed herein that are capable of being integrated into different types of medical devices, such as, IV catheters, sheath introducers, tear-away sheaths, etc. for the purpose of regulating the passage of fluids and/or devices into and out of such devices.

26 Claims, 35 Drawing Sheets

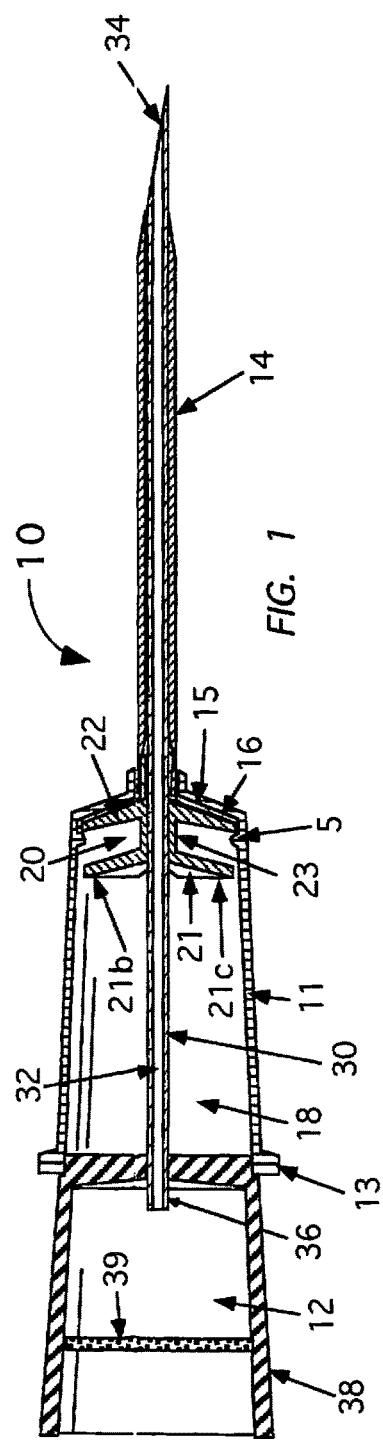
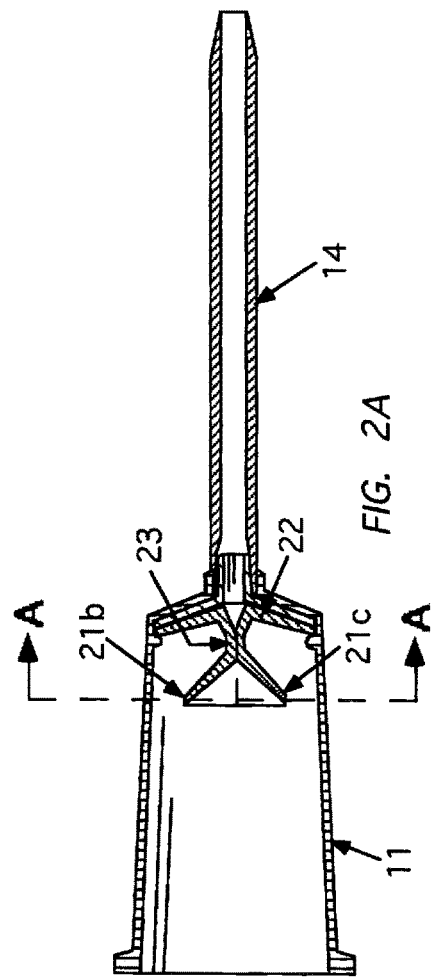
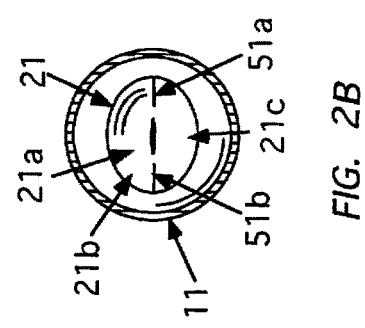
FIG. 1
FIG. 2A
FIG. 2B

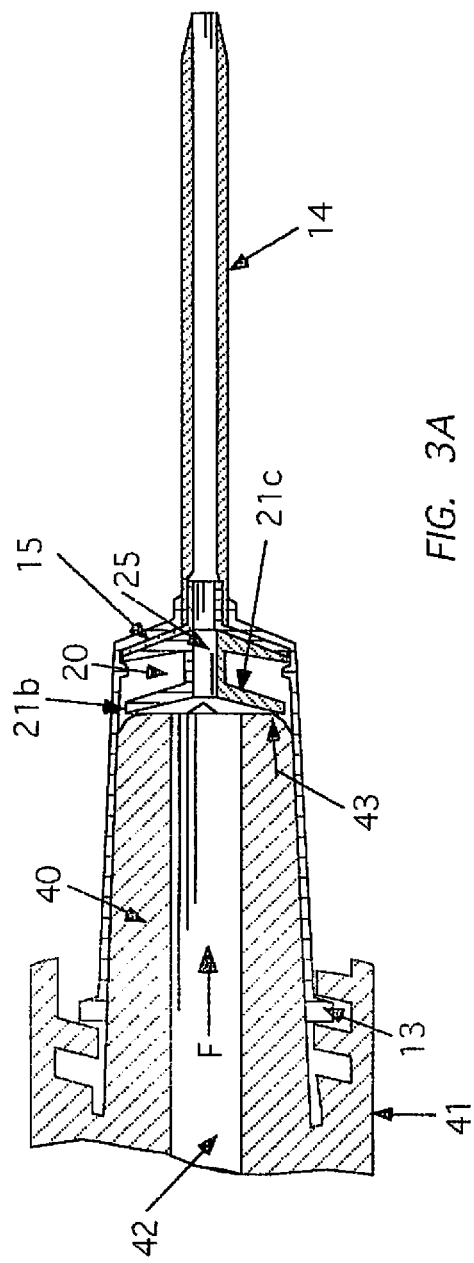

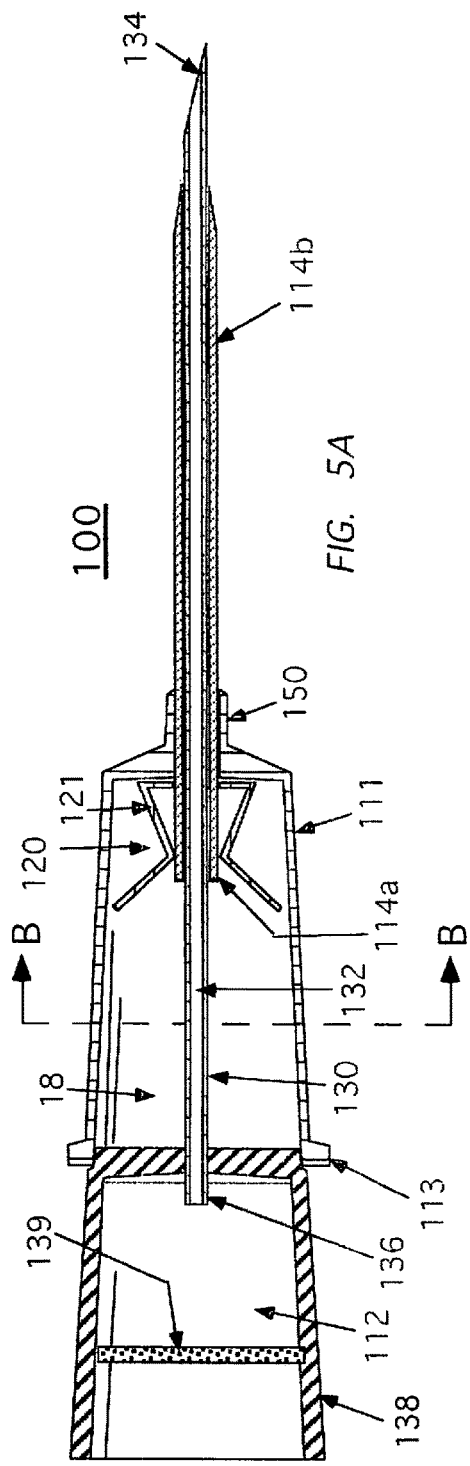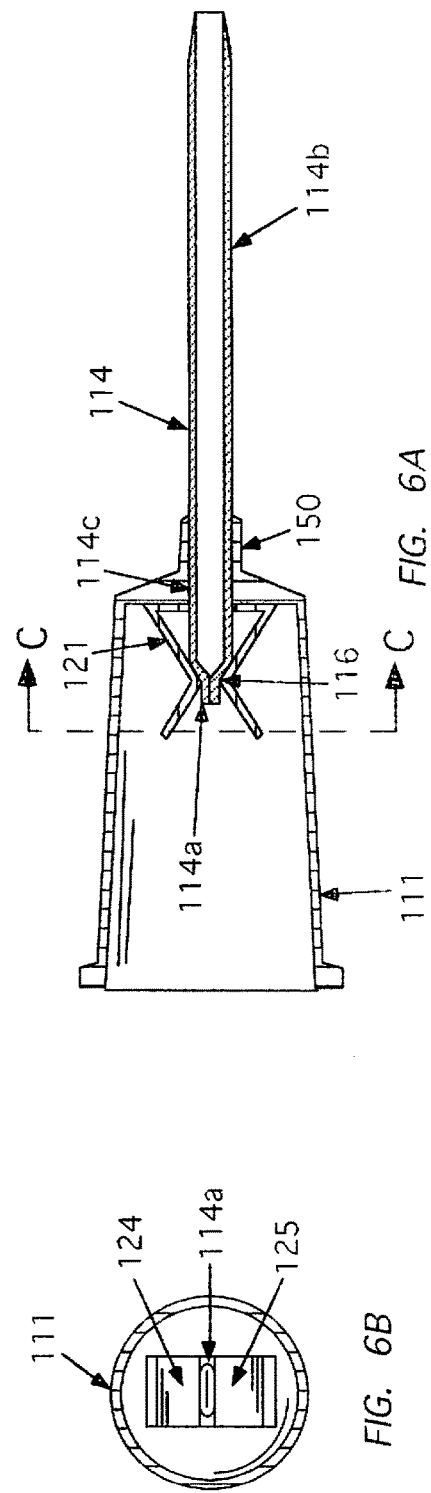

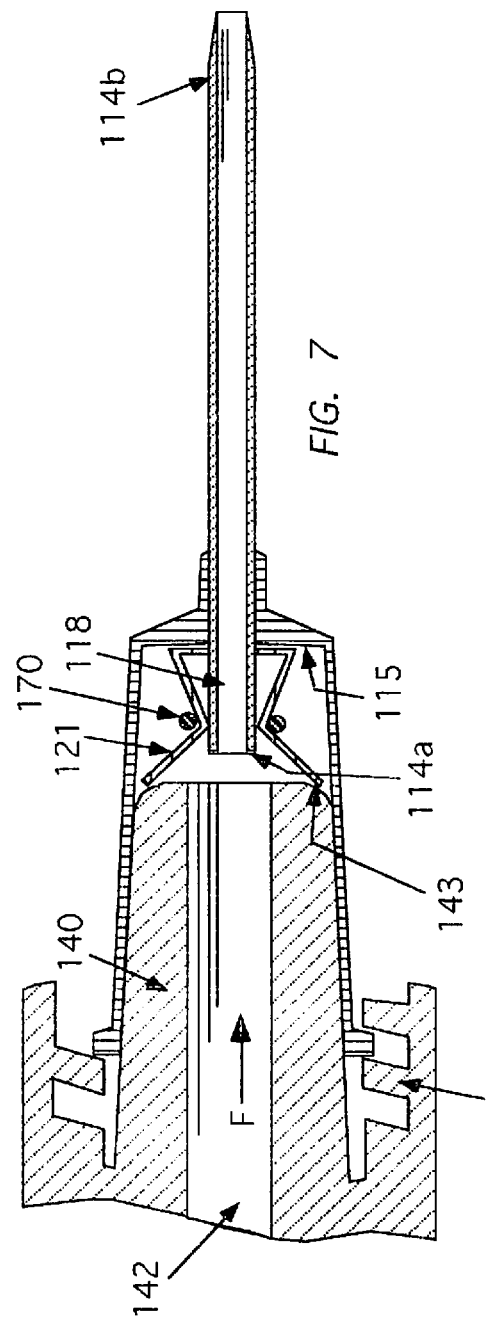
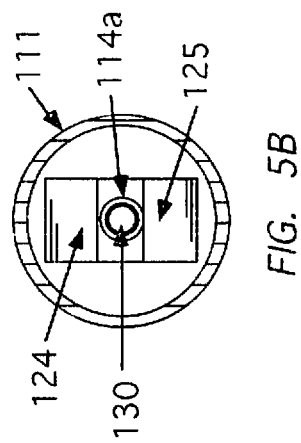

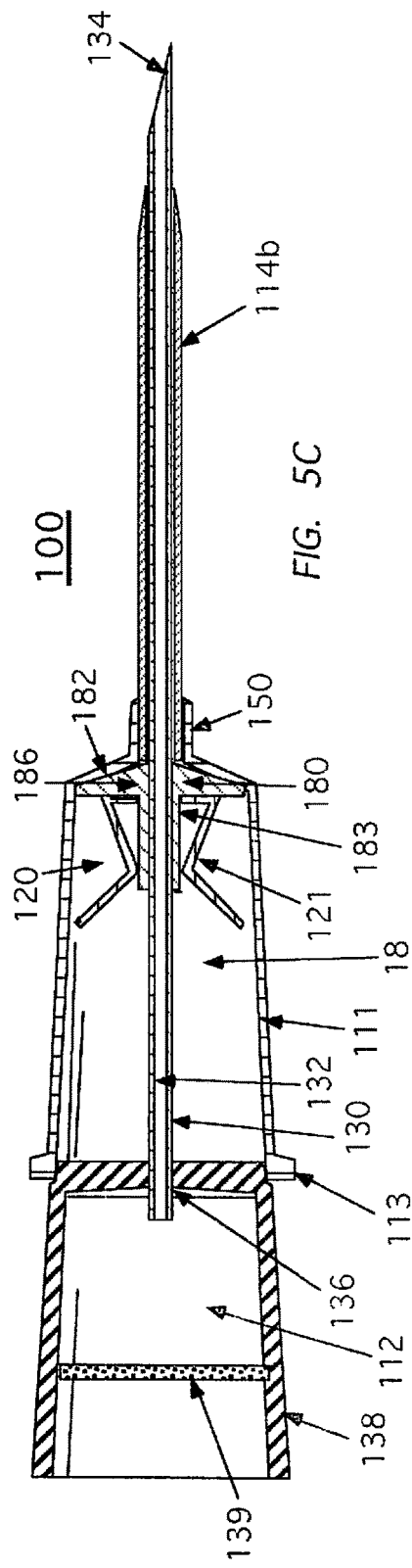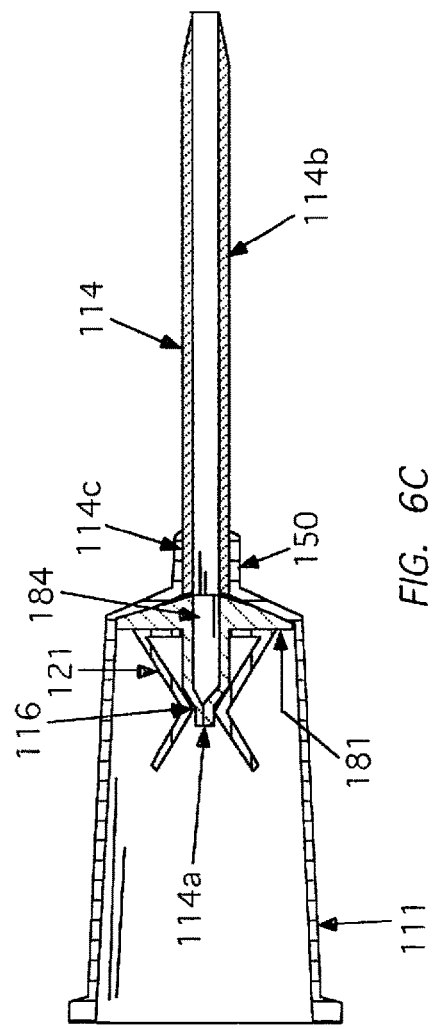

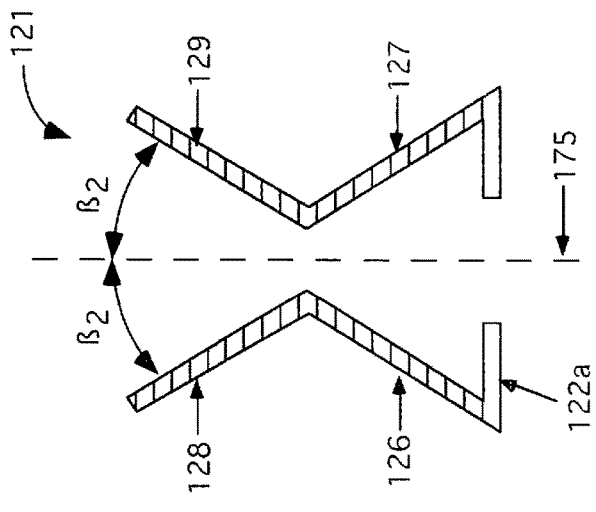
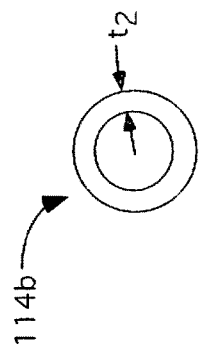
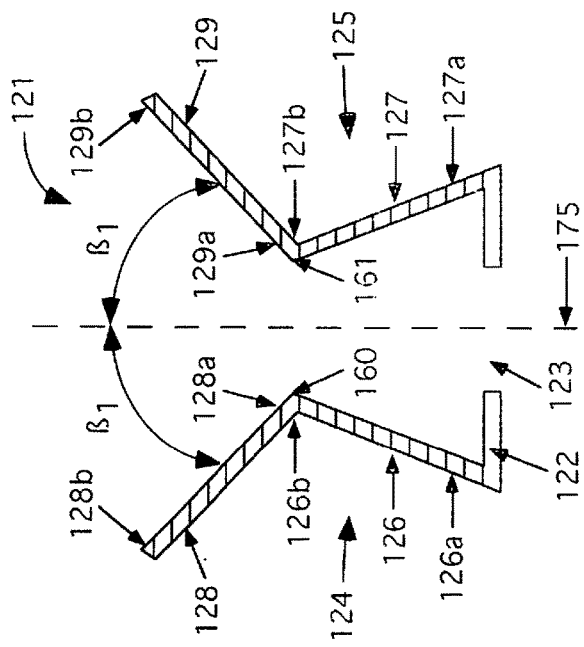
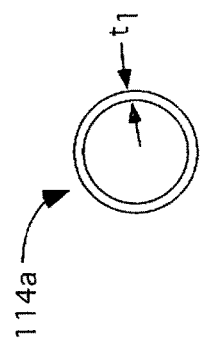
FIG. 9A
FIG. 9B
FIG. 10A
FIG. 10B

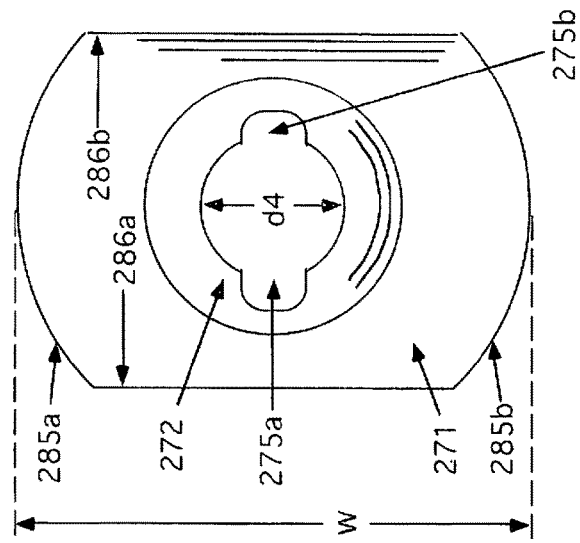
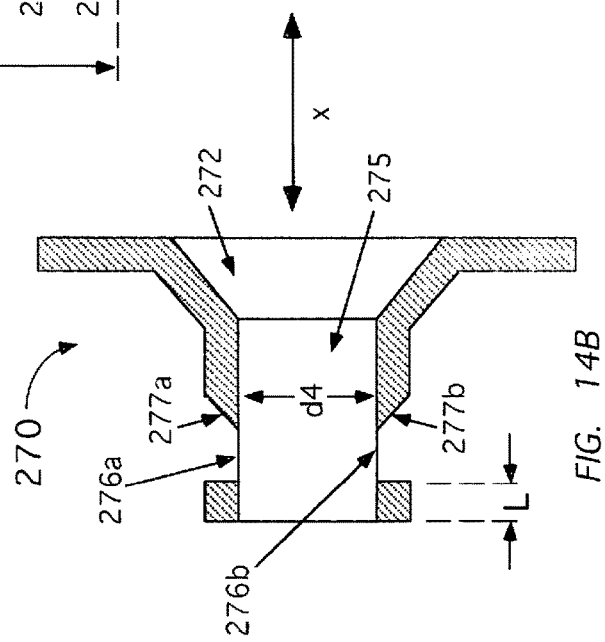
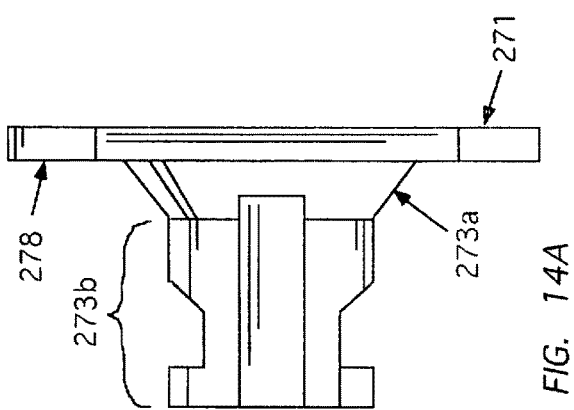
FIG. 14C
FIG. 14B
FIG. 14A

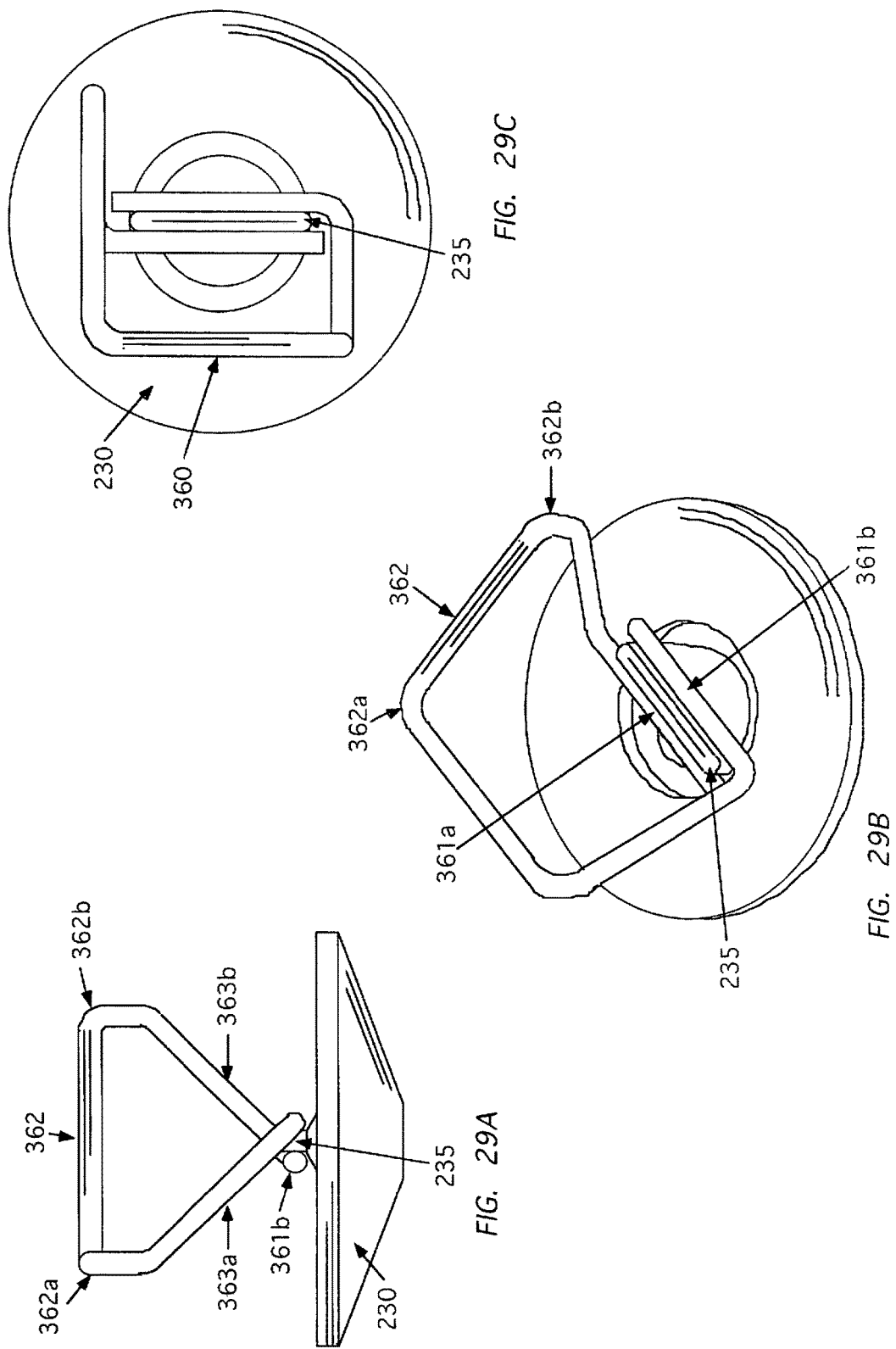

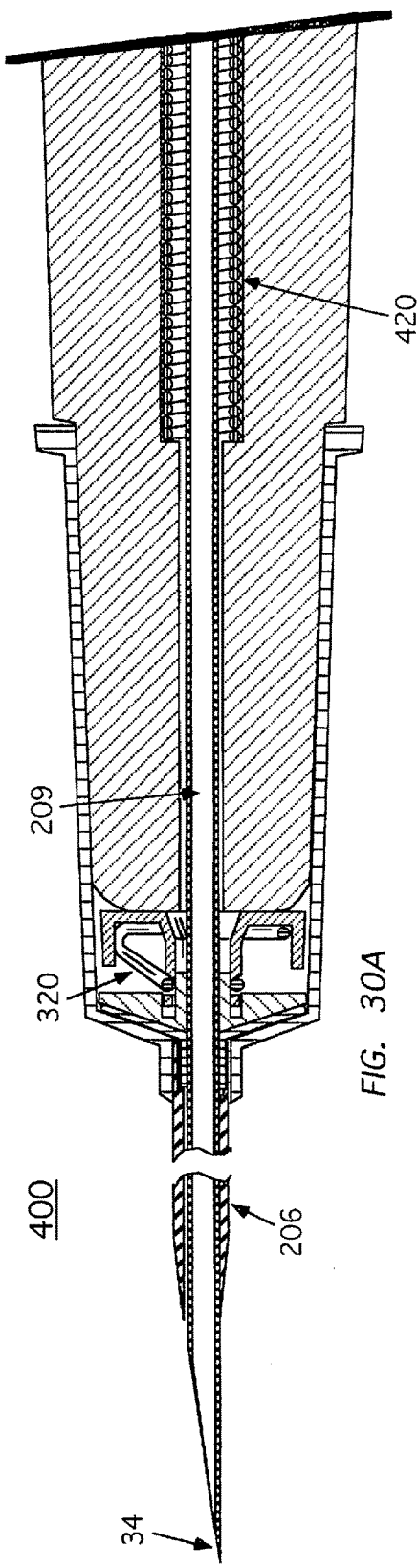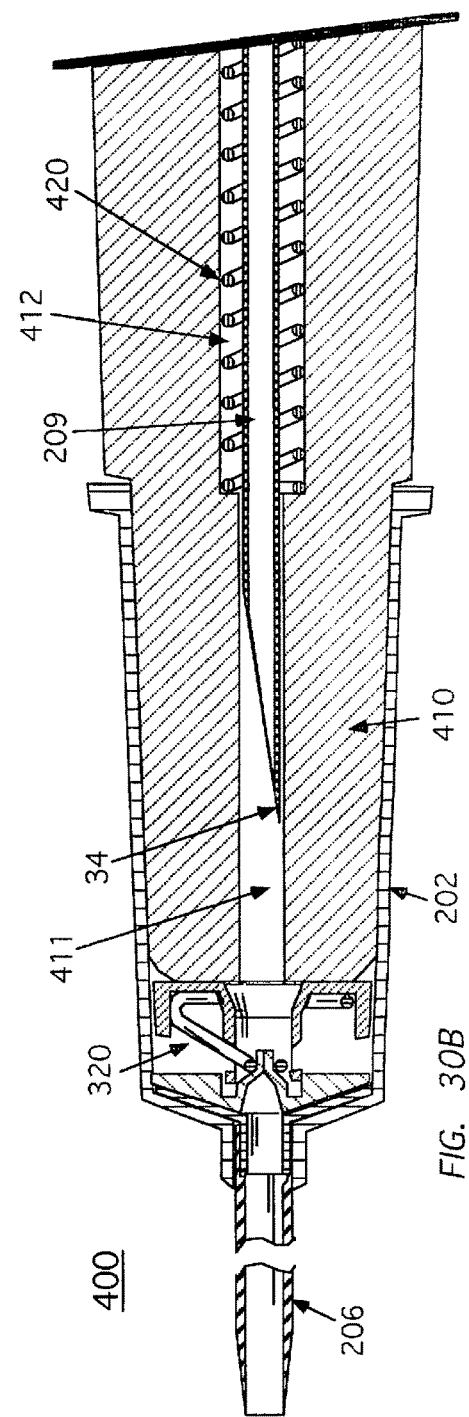

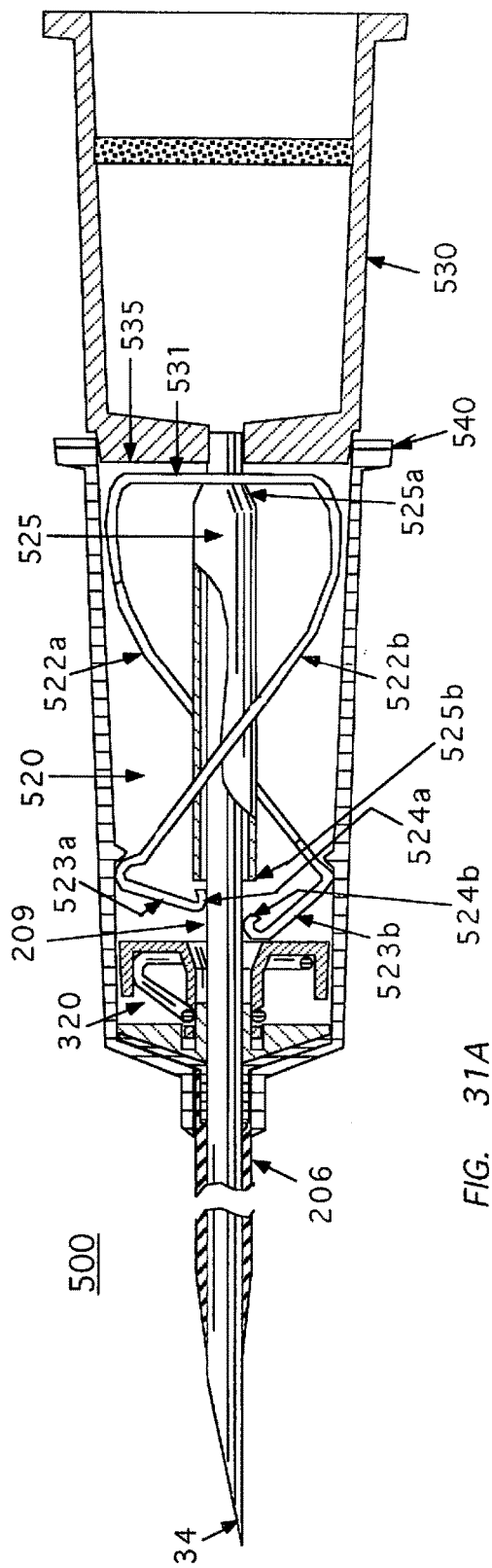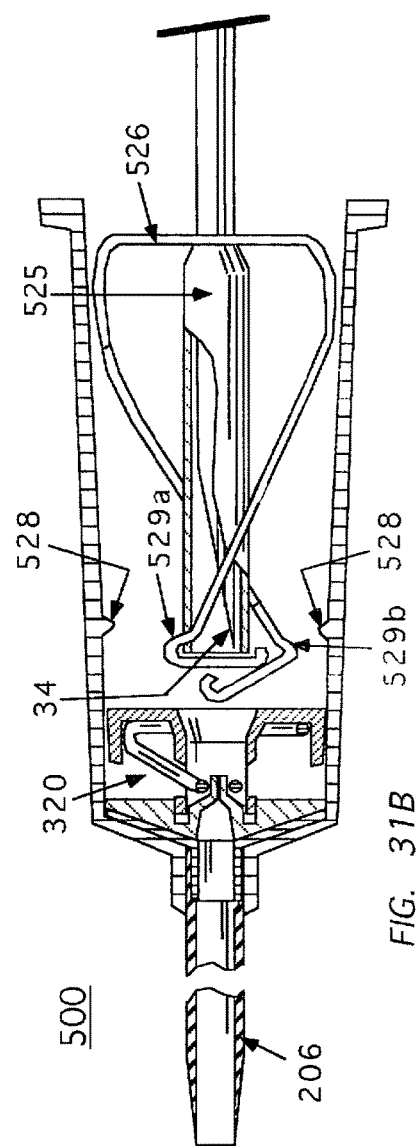
FIG. 31A
FIG. 31B

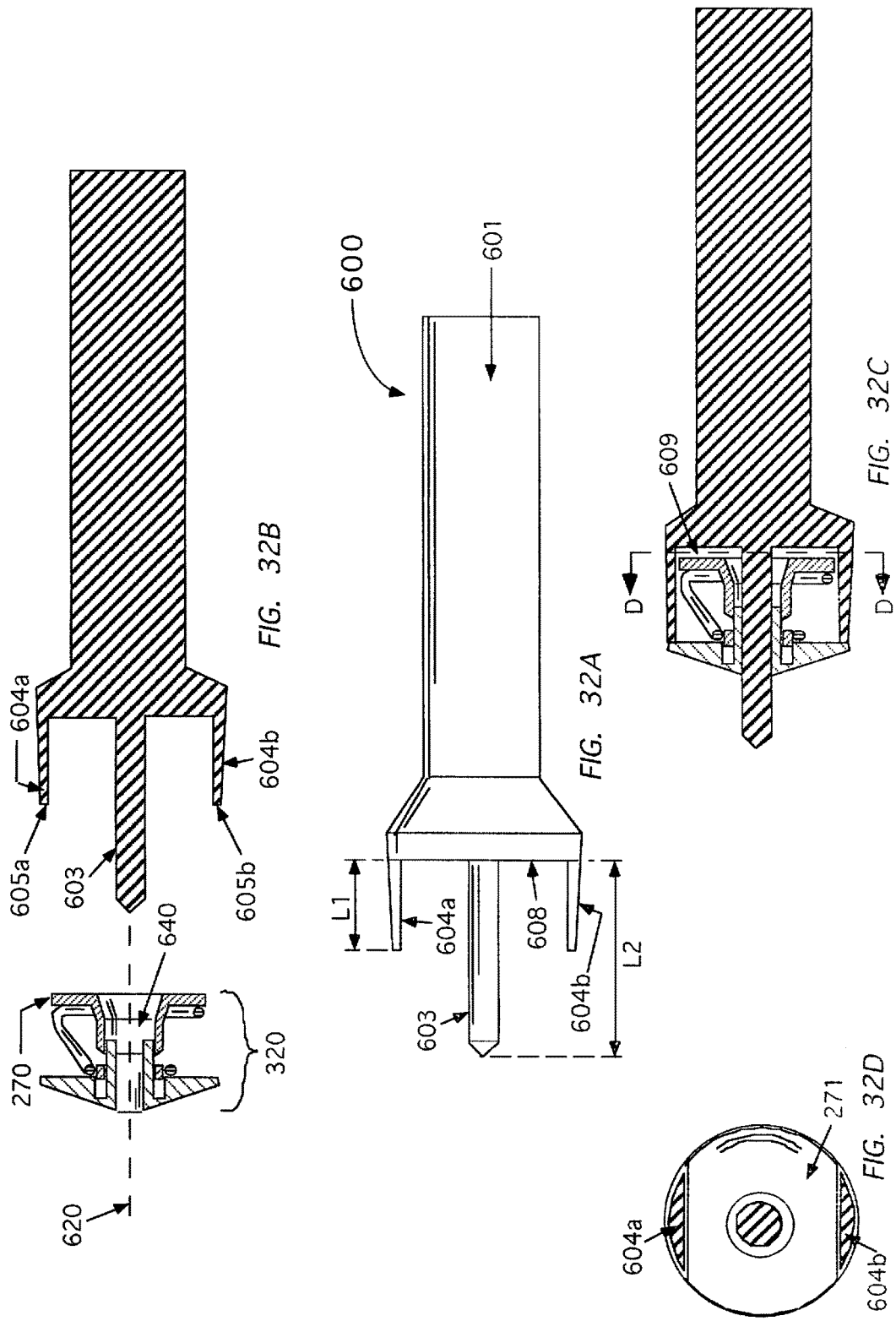

LUER-ACTIVATED VALVES

FIELD

The present invention relates to an apparatus, system and method for selectively blocking the fluid path or infusion stream of a medical device, particularly related to flushable intravenous (IV) catheters, sheath introducers, tear-away sheaths or in-line intravenous infusion valves and connectors.

BACKGROUND

Catheters are universally used to administer fluid, medicine or parenteral nutrients, withdraw blood, aspirate an embolism, or monitor a patient in need of medical attention. An over-the-needle catheter is used to access a blood vessel, the needle is withdrawn and IV tubing is coupled to the proximal end catheter hub via a luer-lock connector. As the needle is removed from the catheter, the clinician simultaneously places a digital pressure on the catheter tube in the vessel to constrict the fluid path to stop blood leaking from the catheter hub into the workplace, and in doing so, reduces the probability of a blood exposure to the clinician. If the clinician fails to constrict the fluid path, blood is free to flow from the patient and out of the sheath, creating a potential blood exposure for the clinician.

Introducer sheaths and tear-away sheaths are widely used to facilitate vascular or bodily access into a patient. The core or obturator of the introducer sheath or tear-away sheath is withdrawn leaving the distal portion of the sheath positioned in the patient and the proximal end of the sheath outside the patient. Some tear-away sheaths include duck-bill valves in an attempt to limit blood loss. However, blood typically leaks through the sheath.

Fluids administered to a patient through an IV catheter are delivered through a series of tubes, connectors and valves. In-line infusion, or needleless valves and connectors are classified in use as: split septum (creates negative displacement); capped luer (creates negative displacement); mechanical valve (creates negative displacement); and surface septum (creates positive displacement). Negative or positive endolumenal displacement in the fluid path is well known in the medical literature to cause catheter occlusion via blood reflux.

A number of safety IV catheters now include a luer-activated valve comprising a longitudinally movable piston, co-operable resilient duck-bill or split septum membrane positioned orthogonally to the piston axis, requiring these split septum flaps to be stored in a stressed or deformed state the entire time the needle resides in the catheter hub. This means the flaps are deformed from the time components are assembled until the device is used. Resilient material takes a "set" when it is positioned in a configuration that differs from its original formed configuration. With an extended shelf life of up to 5 years, the material integrity of the split septum flaps degrades and fatigues significantly, and performs poorly and leaks when the needle is finally removed after the IV catheter is advanced into the patient. The movement of the piston also displaces fluid in the fluid path, creating positive endolumenal pressure when the piston moves distally, and creating a negative endolumenal pressure when the piston moves proximally, increasing the probability of catheter occlusion. These split septum/piston valves also require the catheter hub dimensions to be increased, both outside diameter and length, adding mass to the device, adding bulk to the packaging and medical waste stream, and altering the clinician's proprioception associated with IV catheter placement.

SUMMARY

According to one implementation a luer-activated valve is provided that allows the clinician to selectively occlude or close, or open the fluid path of a flushable IV catheter, sheath introducer, tear-away sheath or in-line infusion connector valve multiple times without creating a positive or negative displacement within the fluid path of the device.

According to some implementations a luer-activated valve of unitary construction (i.e. made from a single piece of material) is provided. According to some implementations a luer-activated valve is provided that includes a deformable, resilient elongate member having a through passage or fluid path that can be selectively opened with the use of a luer fitting and transitions to a closed position to occlude blood flow through the valve by removing the needle or luer fitting from the valve. According to some implementations the luer-activated valve is a displacement-neutral valve and is stored in a non-stressed or relaxed state, automatically blocking the fluid path when the needle is removed from an IV catheter hub, selectively opens when a male luer connector is inserted into the catheter hub, selectively closes when the luer connector is removed, and functions multiple times when a male luer connector is inserted or removed from the catheter hub.

According to some implementations the luer-activated valve reduces assembly cycle time and simplifies the assembly process and insures the tip of the needle remains sharp because it is not touched or damaged during assembly.

According to one implementation the valve includes a clamping member that is triggered by an actuator when a needle or luer hub is positioned within the catheter hub. In a first position, the clamping member is retained on a distal wall portion of the actuator and does not contact the exterior wall of the through passage of resilient member of the luer-activated valve. The second position is created when the needle and needle hub are inserted in the IV catheter hub, engaging the moveable ferrule or actuator to release the clamping member from a first retained position, to a second ready-to-use position where a compressive radial force is placed on the resilient elongate tube of the luer-activated valve. When the needle is removed from the catheter hub, the clamping arms or segments move to a third position, squeezing the elongate tube and closing the fluid path. The compressive force of the clamping arms or segments is selectively releasable when the distal end of a luer connector engages the clamping arms and opens the luer-activated valve.

According to other implementations, a luer-activated valve is provided that includes a clamp co-operable with a resilient elongate member. According to some implementations, a luer-activated valve is provided that includes a resilient member, a clamp and an actuator. According to some implementations, a valve is provided that comprises a metal clip with opposing arms co-operable with a male luer connector to open or close the fluid path of a resilient elongate member. According to some implementations, a luer-activated valve is provided that comprises a sub-assembly having an open, un-restricted through passage. According to some implementations, a valve is provided that comprises a base, a mid-section valve and opposing arms co-operable with a male luer connector to selectively open or close the fluid path of the valve.

These and other implementations along with their advantages and features will become evident in view of the drawings and the detailed description.

BRIEF DESCRIPTION OF THE DRAWINGS

FIG. 1 shows a cross-sectional side view of a ready-to-use IV catheter according to one implementation having a luer-activated valve in a first position with the needle of the IV catheter passing through the luer-activated valve.

FIG. 2A shows a cross-sectional side view of the luer-activated valve of FIG. 1 in a second position with the needle removed, having an obstructed, clamped or closed fluid path.

FIG. 2B shows a rear view of the luer-activated valve shown in FIG. 2A along axis AA.

FIG. 3A shows a cross-sectional side view of the luer-activated valve of FIG. 1 in a third position having an unobstructed, or open fluid path when a luer-tipped connector is placed within the IV catheter hub.

FIG. 5A shows a cross-sectional side view of a ready-to-use IV catheter having a luer-activated valve in a first, retained position with a spring clip placing a compressive, clamping force on a resilient elongate tube that is in fluid communication with the catheter tube.

FIG. 5B shows a rear view of the luer-activated valve shown in FIG. 5A in the IV catheter in axis BB in a first, retained position with the needle passing through the luer-activated valve.

FIG. 5C is a side cross-sectional view of a luer activated valve located inside an IV catheter, the luer activated valve acting on a tubular projection of a valve plug.

FIG. 6A shows a cross-sectional side view of the luer-activated valve of FIG. 5A in a closed position with the needle removed, having an obstructed, clamped or closed fluid path.

FIG. 6B shows a rear view of the luer-activated valve shown in FIG. 6A in the IV catheter in axis CC in the closed position.

FIG. 6C is a side cross-sectional view of a luer activated valve located inside an IV catheter, the luer activated valve acting on a tubular projection of a valve plug to effectuate a closing an internal through lumen located inside the tubular projection.

FIG. 7 shows a cross-sectional side view of a luer-activated valve in a second open position having an unobstructed or open fluid path when a luer fitting is placed within the IV catheter hub.

FIG. 9A is a stand-alone cross-sectional side view of the spring clip in an open position.

FIG. 9B is a stand-alone cross-sectional side view of the spring clip in a closed position.

FIG. 10A shows a cross-sectional view of a proximal portion of the resilient elongate tube.

FIG. 10B shows a cross-sectional view of the distal end portion of the catheter tube.

FIG. 14A shows a side view of a valve actuator according to one implementation.

FIG. 14B is a cross-sectional side view of the valve actuator of 14A.

FIG. 14C is a proximal end view of the actuator shown in FIGS. 14A and 14B.

FIGS. 29A-C show alternative views of the spring member and valve plug with the valve in the closed position as depicted in FIG. 26.

FIGS. 30A and 30B are cross-sectional side views of an IV catheter similar to that of FIG. 25 having incorporated therein a needle guard.

FIGS. 31A and 31B are cross-section side views of an IV catheter having incorporated therein a spring clip needle guard.

FIGS. 32A-G illustrate a method of loading a valve assembly into the hub of an IV catheter with the use of a mandrel.

DETAILED DESCRIPTION

Figure 3B:
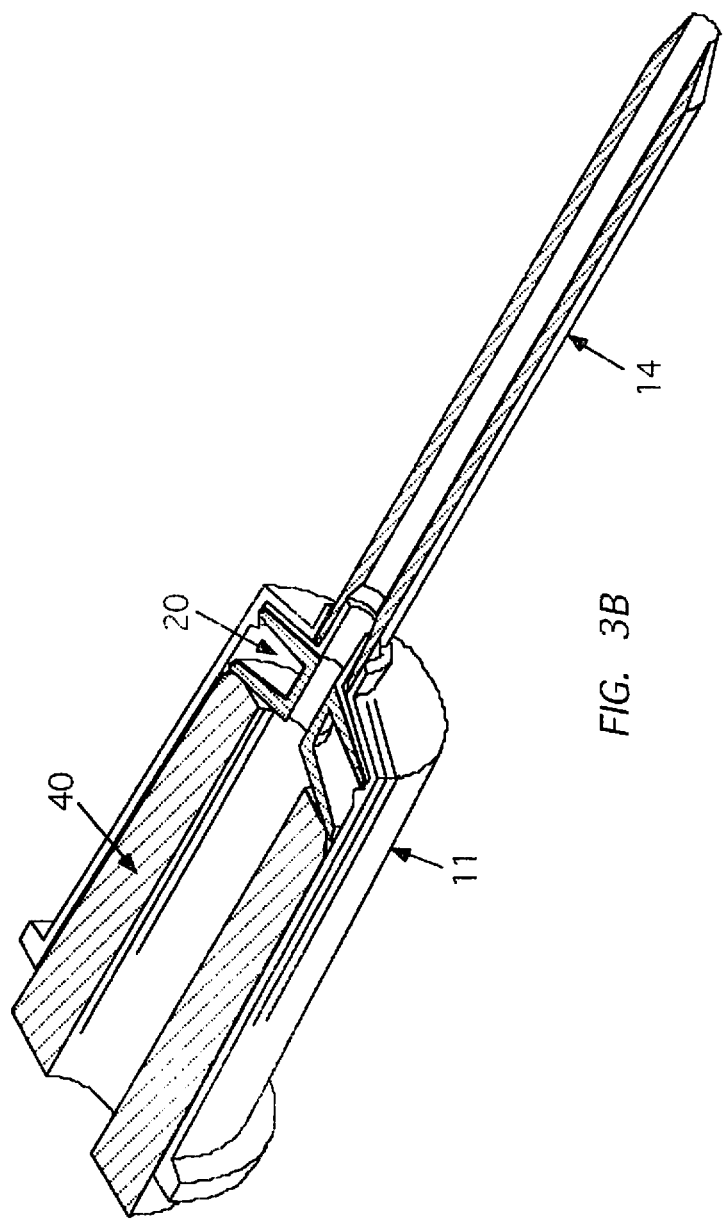
FIG. 3B is an isometric, cross-sectional view of the luer-activated valve of shown in FIG. 3.

A number of luer-activated valves are disclosed herein. In the following description, numerous specific details are set forth in order to provide a thorough understanding of the present invention. However, it will be obvious to one of ordinary skill in the art that the invention may be practiced without these specific details. In other instances, well-known structures and processing steps have not been shown in particular detail in order to avoid unnecessarily obscuring the present invention. Additionally, it should be noted that the invention is applicable to a variety of hypodermic devices and infusion devices such as IV catheters, sheath introducers, tear-away sheaths or in-line infusion valves. It is appreciated, however, that the present invention is not limited to these devices.

It is understood that the luer-activated valves disclosed herein in regard to IV catheters can easily be adapted to all types of other devices where a needle or guidewire may be used, including, but not limited to, sheath introducers, tear-away sheaths, or in-line infusion valves and connectors. The luer-activated valves disclosed herein in use with an IV catheter can also be easily adapted to an endovascular needle, or other needles used in invasive procedures.

FIG. 1 illustrates a cross-sectional side view of a ready-to-use over-the-needle, flushable IV catheter 10 having luer-activated valve 20 in a first retained position with a hollow bore needle 30 extending through the luer-activated valve. According to some implementations the needle 30 includes an inner lumen 32 and a distal sharpened, beveled tip 34. A proximal end portion 36 of needle 30 is attached to a needle hub 38. According to one implementation the needle hub 38 includes a gas-permeable portion 39 for venting air as blood fills the catheter hub 11. The catheter hub 11 includes a flashback chamber 12 and has at its proximal end a proximal luer flange 13 for attaching a luer-lock fitting. The catheter 10 includes a polymeric hollow catheter tube 14 that, according to one implementation, is press fit in the distal end of hub 11 over ferrule 16. According to one implementation the proximal luer flange 13 is configured to facilitate an attachment of a male luer fitting 40 to the catheter hub 11 as shown in FIGS. 3A and 3B.

The luer-activated valve 20 is located inside the catheter hub 11 and includes a proximal flange portion 21, a distal flange portion 22 and a tubular portion 23 a tubular part extending between the proximal and distal flanges. The valve 20 is configured to assume an open position as shown in FIGS. 1, 3A and 3B and a closed position as shown in FIGS. 2A and 2B. According to one implementation the valve 20 is made of a resilient polymeric material and constructed such that the valve is continuously urged toward the closed position.

Figure 4B:
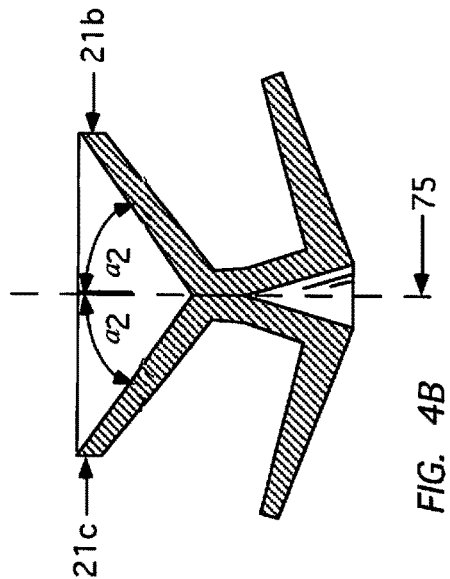
FIG. 4B is a cross-sectional side view of the luer-activated valve in a closed position.
Figure 4A:
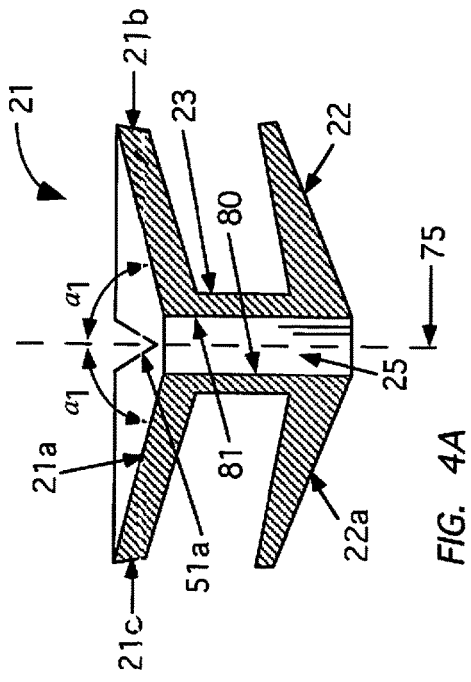
FIG. 4A is a cross-sectional stand-alone side view of the luer-activated valve in a first open position.
Figure 4C:
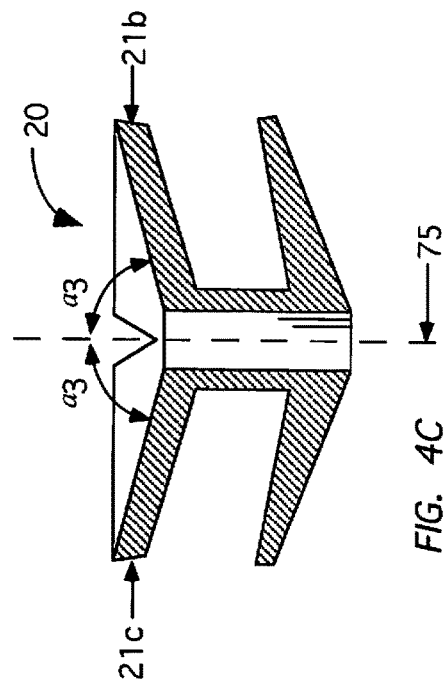
FIG. 4C is a cross-sectional stand-alone side view of the luer-activated valve in a second open position.

In use, valve 20 has first and second open positions. The first open position is shown in FIG. 1 wherein the inner walls of the tubular portion of the valve 20 are pressed outward as a result of the needle 30 passing therethrough. When the needle 30 is removed from the IV catheter 10, the valve 20 automatically transitions to the closed position as shown in FIGS. 2A and 2B due to the resilient nature of the tubular portion 23. In the closed position a part of the tubular portion 23 of the valve 20 is caused to close on itself as shown in FIG. 2A. According to one implementation, the outer diameter of the needle 30 and the inner diameter of the tubular portion 23 of the valve 20 are dimensioned to cause the inner walls 80 and 81 (see FIG. 4A) of the tubular portion 23 of the valve to press against the outer surface of the needle 30 to prevent the passage of blood between them. FIGS. 4A and 4C are enlarged cross-section views of the valve 20 respectively shown in the first and second open positions. FIG. 4B is an enlarged cross-section view of the valve 20 shown in the closed position.

When valve 20 is in the closed position it is capable of assuming the second open position as shown in FIGS. 3A and 3B upon there being a distally applied force to a proximal face 21a of the proximal flange 21, the valve transitions from the closed position to the second open position and subsequently returns to the closed position when the distally applied force is removed. In the second open position fluid flow is permitted through an opening 25 that extends through the proximal and distal flanges and the tubular part. When valve 20 is in the closed position fluid flow is impeded by a closing of the opening 25.

The valve 20 is in a rest position when the valve assumes the closed position. According to one implementation the proximal flange 21 includes first and second wing portions 21b and 21c. According to one implementation one or both of the wing portions 21b and 21c is positioned at an angle $\alpha_1$ with respect to the valve's longitudinal axis 75 when the valve 20 in the first open position as shown in FIG. 4A and an angle $\alpha_2$ when the valve is in the closed position as shown in FIG. 4B, the angle $\alpha_1$ being greater than $\alpha_2$. When the valve 20 is in the second open position one or both of the wing portions 21b and 21c is positioned at an angle $\alpha_3$ with respect to the longitudinal axis 75 of the valve 20 as shown in FIG. 4C with angle $\alpha_3$ being greater than $\alpha_2$. According to one implementation $\alpha_3$ is also greater than $\alpha_1$. When the valve 20 is in either the first or second open position, the change in angular orientation of the wing portions 21b and 21c occurs automatically due to the resilient nature of the valve.

According to one implementation, valve 20 is positioned at the distal end of the catheter hub 11 such that the distal face 22a of the distal flange 22 faces the inner distal wall 15 of the catheter hub. In the implementation shown in FIGS. 1-3B the distal face of the distal flange 22 abuts a portion of the ferrule 16 located inside the catheter hub, the ferrule being interposed between distal face of the flange and the inner distal wall of the catheter hub 11. According to one implementation the distal flange 22 of valve 20 is held in the distal end portion of the catheter hub 11 by a rigid annular lip 5 protruding radially inward from an inner wall of the catheter hub. When valve 20 is initially introduced into the catheter hub 11, the distal flange 22 is endowed with sufficient flexibility to allow it to deform sufficiently to pass across the annular lip 5. When the distal flange 22 has passed across the annular lip 5 it then, by its resilient nature, returns towards its initial unstressed state and works in conjunction with the annular lip 5 to hold the valve in place inside the catheter hub 11 without the need to use an adhesive. According to one implementation, after placement of the valve 20 inside the catheter hub 11, the distal flange 22 and annular lip 5 further function together to form an annular leak tight seal between them.

According to one implementation the valve 20 is molded part of a unitary construction. That is, it is made of a single piece of material. One or both of the proximal and distal flanges 21 and 22 may be formed or treated in any of a number of ways to provide them with a higher rigidity than that of the tubular portion 23. This has several advantages. By enhancing the rigidity of the distal flange 22 it can be more securely fixed inside the catheter hub 11 making it more difficult to proximally move the distal flange across the annular lip 5 inside the catheter hub. By enhancing the rigidity of the proximal flange 21, it can safeguard against a folding of the flange on itself to ensure a sufficient amount of force is capable of being applied to the proximal flange by the male luer connector to cause the opening of the tubular portion 23 of the valve when the distally applied force is applied to the proximal flange.

FIG. 1 illustrates the IV catheter 10 in a ready-to-use state with the needle hub 38 attached to the proximal end of the catheter hub 11 and the introducer needle 30 passing through the through opening 25 of valve 20 and through the catheter tube 14. The sharpened distal tip 34 of the needle 30 extends beyond the distal end of the catheter tube 14.

After the catheter tube 14 has been properly placed inside a vein or another part of the patient, the needle 30 is withdrawn by decoupling the needle hub 38 from the catheter hub 11 and withdrawing the needle from the device so that thereafter the assembly of FIG. 2A is produced. As discussed above, as the needle 30 is withdrawn from the through opening 25 of the valve 20, the valve transitions from the first open position as shown in FIG. 1 to the closed position as shown in FIGS. 2A and 2B. Thereafter, fluids may be withdrawn from or administered to the patient through the indwelling catheter tube 14. According to one implementation this is accomplished by introducing a male luer fitting 40 into the catheter hub 11 as shown in FIGS. 3 and 4. The male luer connector 40 includes a part 41 (e.g. threads) that cooperates with the proximal luer flange 13 of the catheter hub to secure the luer connector to the catheter hub. The luer fitting 40 also includes an internal through lumen 42 that is placed into fluid communication with the catheter tube 14 through the valve 20 when the valve has transitioned from the closed position to the second open position.

As the male luer fitting 40 is introduced into the catheter hub 11, its distal end surface 43 makes contact with the wings 21b and 21c of the proximal flange 21 to cause the wings 21b and 21c to flex distally from the first angular position as with respect to the longitudinal axis 75 to a second angular position $\alpha_3$ with respect to the longitudinal axis 75 as discussed above. The valve 20 is constructed such that as the wings 21b and 21c are forced toward and to the second angular position by the distally applied force applied to them by the distal end surface 43 of the luer connector 40, a through passage 25 is established through the valve 20 to place the catheter tube 14 and the inner lumen 42 of the luer connector 40 in fluid communication. When the luer fitting 40 is subsequently removed from the catheter hub 11, the assembly of FIG. 2A is automatically reestablished with the valve 20 reassuming the closed position. According to some implementations the outer diameter of the male luer fitting 40 and the inner diameter of the catheter hub 11 are dimensioned such that when the fitting 40 is positioned inside the catheter hub to cause an opening of the valve 20, a fluid seal is established between the outer circumferential surface of the fitting 40 and the inner wall of the catheter hub.

According to one implementation valve 20 is positioned at a distal end section of the catheter hub 11 without freedom of rotation. This can be achieved by establishing a press-fit relationship between the outer circumferential surface of the distal flange 22 and the inner wall of the catheter hub 11. One or more projections extending radially inward from the inner wall of the catheter hub 11 and acting on the distal flange 22 of the valve 20 may alternatively be provided to inhibit or prevent rotation of the valve 20 during the male luer 40 being advance into or out of the catheter hub 11. The distal face 22a of the distal flange 22 of valve 20 may additionally or alternatively be roughened.

As discussed above, FIGS. 2A and 2B illustrate the valve 20 in the closed position. To assist in facilitating a separating and bringing together of the inner walls of the tubular portion 23 of the valve, the proximal flange 21 may be provided with first and second slits 51a and 51b that each extend partially radially inward form an outer circumference of the proximal flange.

FIGS. 5A-10B illustrate other implementations of a luer-activated valve 120. In the examples of FIGS. 5A-8 the valve 120 is shown being a part of an IV catheter 100.

FIG. 5A illustrates a cross-sectional side view of a ready-to-use over-the-needle, flushable IV catheter 100 having luer-activated valve 120 in a first retained position with a hollow bore needle 130 extending through the luer-activated valve. According to some implementations the needle 130 includes an inner lumen 132 and a distal sharpened, beveled tip 134. A proximal end portion 136 of needle 30 is attached to a needle hub 138. According to one implementation the needle hub 138 includes a gas-permeable portion 139 for venting air as blood fills the catheter hub 111. The catheter hub 111 includes an inner cavity 18 terminating at a proximal luer flange 113. The catheter 100 includes a hollow catheter tube 114 that has a proximal portion 114a residing inside the catheter hub 111 and a distal portion 114b that resides distal to the catheter hub. A segment 114c of the catheter tube 114 is fixed to the catheter hub 111 in a leak-tight manner. The distal-most end of the catheter hub 111 may include an elongate conduit 150 inside which the catheter tube segment 114c resides and is fixed. According to one implementation the proximal luer flange 113 is configured to facilitate an attachment of a male luer fitting 140 as shown in FIG. 7.

Figure 8:
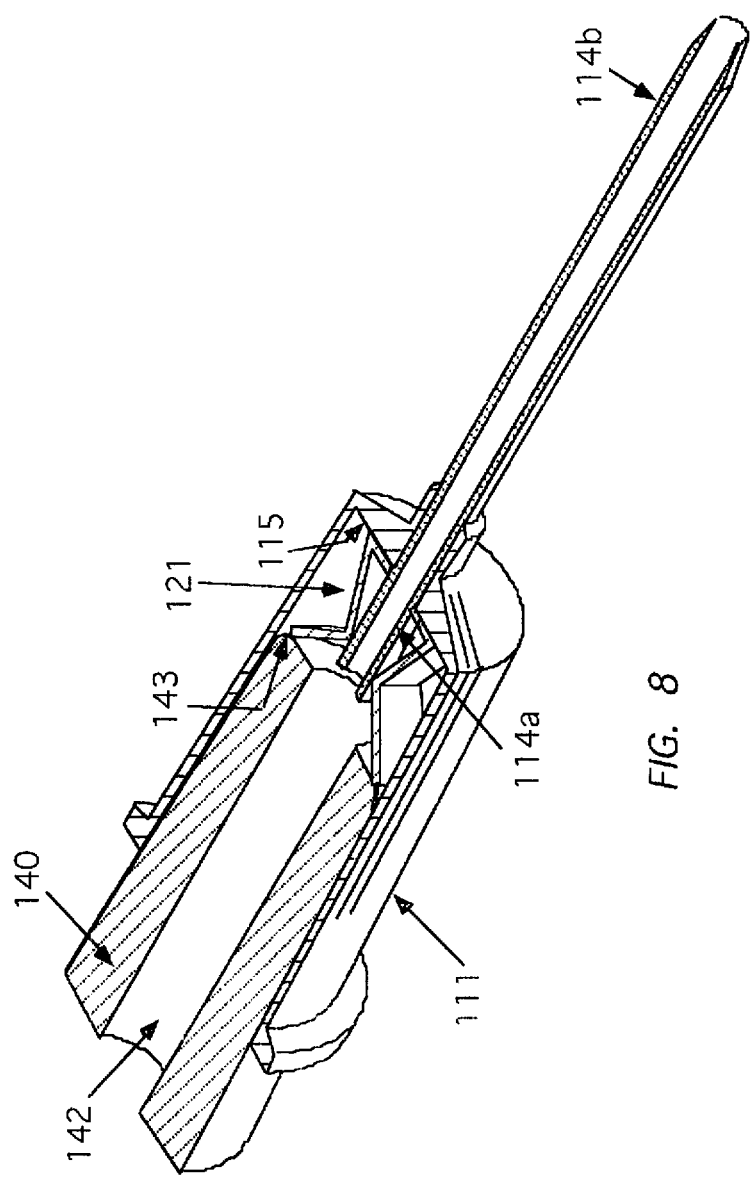
FIG. 8 shows an isometric, cross-sectional view of a luer-activated valve of FIG. 7 having an open fluid path.

The luer-activated valve 120 is located inside the catheter hub 111 and comprises a spring clip 121 and the proximal portion 114a of the catheter tube 114. The valve 120 is configured to assume a first open position as shown in FIGS. 5A and 5B, a second open position as shown in FIGS. 7 and 8, and a closed position as shown in FIGS. 6A and 6B. According to one implementation the spring clip 121 is made of a metal (e.g. stainless steel) and the proximal portion 114a of the catheter tube is made of a resilient polymeric material. The proximal portion 114a is constructed such that it has an ability to be pinched closed by the spring clip 121 as shown in FIGS. 6A and 6B and is thereafter able to automatically assume an open position as shown in FIGS. 7 and 8 when the spring clip 121 seizes to pinch the proximal portion 114a.

FIG. 9A shows an enlarged cross-section view of the spring clip 121 in the second open position. FIG. 9B shows an enlarged cross-section view of the spring clip 121 in the closed position.

The spring clip 121 includes a base 122 having a through opening 123 through which a section of the proximal portion 114a of the catheter tube passes. The spring clip 121 includes first and second arms 124 and 125 that are positioned about the outer surface 116 of the proximal portion 114a of the catheter tube. Each of the first and second arms 124 and 125 respectively includes a first section 126 and 127 having a distal end 126a and 127a and a proximal end 126b and 127b. The distal end 126a of the first section 126 of arm 124 is coupled to the base 122 with the proximal end 126b of the first section 126 being disposed radially inward of the distal end 126a of the first section 126 with respect to the longitudinal axis 175. In a similar manner, the distal end 127a of the first section 127 of arm 125 is coupled to the base 122 with the proximal end 127b of the first section 127 being disposed radially inward of the distal end 127a of the first section with respect to the longitudinal axis 175.

Each of the first and second arms 124 and 125 respectively includes a second section 128 and 129 located proximally to first sections 126 and 127. The second section 128 of the first arm 124 has a distal end 128a and a proximal end 128b with the distal end 128a being coupled to the proximal end 126b of the first section 126 of the first arm 124 to form a first pinching site 160. The proximal end 128b of the second section 128 is disposed radially outward of the distal end 128a of second section 128 with respect to the longitudinal axis 175. The second section 129 of the second arm 125 has a distal end 129a and a proximal end 129b with the distal end 129a being coupled to the proximal end 127b of the first section 127 of the second arm 125 to form a second pinching site 161. The proximal end 129b of the second section 129 is disposed radially outward of the distal end 129a of second section 128 with respect to the longitudinal axis 175.

Each of the first and second arms 124 and 125 is made of a resilient material and constructed such that the first and second pinching sites 160 and 161 are continuously urged radially inward toward one another to position the valve in the closed position. In the closed position of the valve 120, the first and second pinching sites 160 and 161 press against opposite sides of the outer surface 116 of the proximal portion 114a of the catheter tube 114 with a force sufficient to cause the tubular wall of the proximal portion 114a to collapse as shown in FIGS. 6A and 6B to cause a full or substantially full closing of the inner lumen 118 of the proximal tube portion 114a.

In the second open position of the valve 120, as shown in FIGS. 7 and 8, the first and second pinching sites 160 and 161 are positioned radially apart from one another so as not to press against the outer surface of the proximal portion of the catheter tube 114a to permit an opening of the inner lumen 118 of the proximal catheter tube portion 114a. As discussed above, the proximal portion 114a of the catheter tube is made of a resilient material that allows the inner lumen to automatically expand from the closed position as shown in FIG. 6A to a full or partial open position as shown in FIGS. 7 and 8.

FIGS. 5A and 5B show the valve 120 in the first open position when the IV catheter 100 is in a ready-to-use state with the introducer needle 130 residing inside the catheter tube 114 with its distal sharpened tip 134 extending distally to the distal-most end of the catheter tube. According to one implementation, in the first open position of valve 120 the first and second pinching sites 160 and 161 press against the outer surface 116 of proximal portion 114a of the catheter tube 114 while the inner lumen 118 of the proximal portion 114a of the catheter tube is maintained open by a passing of the introducer needle 130 through the inner lumen 118. That is, the outer circumferential surface of the needle shaft acts on the inner luminal wall of the proximal catheter portion 114a to maintain the inner lumen 118 open.

According to one implementation, the outer diameter of the needle 130 and the inner diameter of the proximal portion 114a of the catheter tube 114 are dimensioned to cause the inner walls of the proximal portion 114a to press against the outer surface of the needle 30 to prevent the passage of blood between them.

When the needle 130 is removed from the IV catheter 100, the valve 120 automatically transitions to the closed position as shown in FIGS. 6A and 6B due to the resilient nature of the spring clip arms 124 and 125.

When valve 120 is in the closed position as shown in FIGS. 6A and 6B, it is capable of assuming the second open position, as shown in FIGS. 7 and 8, upon there being a distally applied force F to the second sections 128 and 129 of the first and second arms 124 and 125 of spring clip 121. When the distally applied force F is subsequently removed, the valve 120 automatically returns to the closed position.

According to one implementation, one or both of the first and second sections 128 and 129 of arms 124 and 125 is position at an angle $\beta_1$ with respect to the longitudinal axis 175 of the clip when the valve 120 is in at least one of the first and second open positions. When the valve is in the closed position one or both of the first and second sections 128 and 129 of arms 124 and 125 is positioned at an angle $\beta_2$ with respect to the longitudinal axis 175 of the spring clip 121 as shown in FIG. 9B, the angle $\beta_1$ being greater than the angle $\beta_2$.

According to one implementation, spring clip 121 is positioned at the distal end of the catheter hub 111 such that the distal face 122a of the spring clip base 122 faces the distal inner wall 115 of the catheter hub 111. According to one implementation the base 122 is held tight or fixed to the base 115 of the catheter hub 111 without freedom of rotation.

According to one implementation the spring clip 121 is unitarily constructed. That is, it is made of a single piece of material.

As explained above, FIG. 5A illustrates the IV catheter 100 in a ready-to-use state with the needle hub 138 attached to the proximal end of the catheter hub 111 and the introducer needle 130 passing though the valve 120 and catheter tube 114.

After the catheter tube 114 has been properly placed inside a vein or another part of the patient, the needle 130 is withdrawn by decoupling the needle hub 138 from the catheter hub 111 and withdrawing the needle from the device so that thereafter the assembly of FIG. 6A is produced. As discussed above, as the needle 130 is withdrawn, the valve 120 transitions from the first open position as shown in FIGS. 5A and 5B to the closed position as shown in FIGS. 6A and 6B. Thereafter, fluids may be withdrawn from or administered to the patient through the indwelling catheter tube 114 located inside the patient. According to one implementation this is accomplished by introducing a male luer fitting 140 into the catheter hub 111 as shown in FIGS. 7 and 8. The male luer fitting 140 includes a part 141 (e.g. threads) that cooperates with the proximal luer flange 113 of the catheter hub 111 to secure the luer connector to the catheter hub. The luer connector 140 also includes an internal through lumen 142 that is placed into fluid communication with the catheter tube 114 through the valve 120 when the valve has transitioned from the closed position to the second open position. In the implementation of FIGS. 5A-8, the valve 120 is comprised of the spring clip 121 and the proximal portion 114a of the catheter tube 114 on which the spring clip acts.

As the male luer fitting 140 is introduced into the cavity of the catheter hub 111, its distal end surface 143 makes contact with the second sections 128 and 129 of the arms 124 and 125 of spring clip 121 to cause the second sections 128 and 129 to flex distally from angular position $\beta_2$ with respect to angular position Pi. The spring clip is constructed such that as the second sections 128 and 129 of arms 124 and 125 are forced to angular position $\beta_1$ by the distally applied force applied to them by the distal end surface 143 of the luer connector 140, the first and second pinching sites 160 and 161 move radially away from one another to enable the proximal portion 114a of the catheter tube 114 to automatically open to place the catheter tube 114 and the inner lumen 142 of the luer connector 140 in fluid communication. When the luer connector 140 is subsequently removed from the catheter hub 111, the assembly of FIG. 6A is automatically reestablished with the valve 120 assuming the closed position.

As shown in FIG. 7, according to one implementation the luer-activated valve 120 further includes a resilient O-ring 170 positioned about the first and second pinching sites 160 and 161. The resilient O-ring 170 is dimensioned and positioned on the spring clip 121 in the region of the first and second pinching sites 160 and 161 in a manner that results in a continuous compressive force being applied to the arms 124 and 125 of the spring clip 121 by the O-ring to assist in urging the valve 120 continuously toward the closed position.

As shown in FIGS. 10A and 10B, according to one implementation the proximal portion 114a of the catheter tube 114 has a wall thickness t1 that is less than the wall thickness t2 of the distal portion 114b. The reduced wall thickness in the proximal portion 114a causes it to be more easily compressed by the spring clip 121. According to other implementations the tubular walls of the proximal portion 114a are made to have a Shore hardness that is less than the Shore hardness of the tubular walls of the distal portion 114b of the catheter tube 114.

In the implementations of FIGS. 5A-10B the tubular portion 114a of valve 120 forms a single part with the remaining part of the catheter tube 114. According to other implementations the tubular portion 114a is not a part of the catheter tube 114, yet is coupled to the catheter tube in a way that places them in fluid communication with one another.

As shown in FIGS. 5C and 6C, according to some implementations the proximal end of the catheter tube 114 does not extend into the inner cavity of the catheter hub 111, but is instead coupled to a distal end of the catheter hub. In the implementations of FIGS. 5C and 6C a valve plug 180 is positioned at the internal distal end of the catheter hub 111. The valve plug 180 includes a through opening 184 and is arranged in the catheter hub 111 to substantially place the through opening 184 in axial alignment with a proximal end of the catheter tube. The valve plug includes a base 186 having a proximal facing surface 181 and a distal facing surface 182. Extending proximally from the base is a tubular projection 183. According to some implementations a recess is provided in the proximally facing surface 181 in which resides the base 122 of the spring clip 121. In FIG. 5C the valve clip 121 is arranged as shown in FIG. 9A so that the first and second pinching sites 160 and 161 press against the outer wall of the tubular projection 183, the through opening 184 of the plug 180 being maintained in an open state as a result of the needle 130 passing therethrough. In FIG. 6C the valve clip 121 is arranged as shown in FIG. 9B with the needle 130 having been removed from the IV catheter. With the needle 130 removed from the IV catheter the first and second pinching sites of the valve clip 121 automatically move radially inward towards one another to cause at least a portion of the through opening extending through the tubular projection 183 to close.

According to some implementations the valve plug 180 is disposed inside the catheter hub 111 in a manner that prevents its rotation therein. According to some implementations the valve clip 121 is supported on or in a recess of the valve plug 180 in a manner that prevents or resists its rotation thereon or therein.

Figure 11:
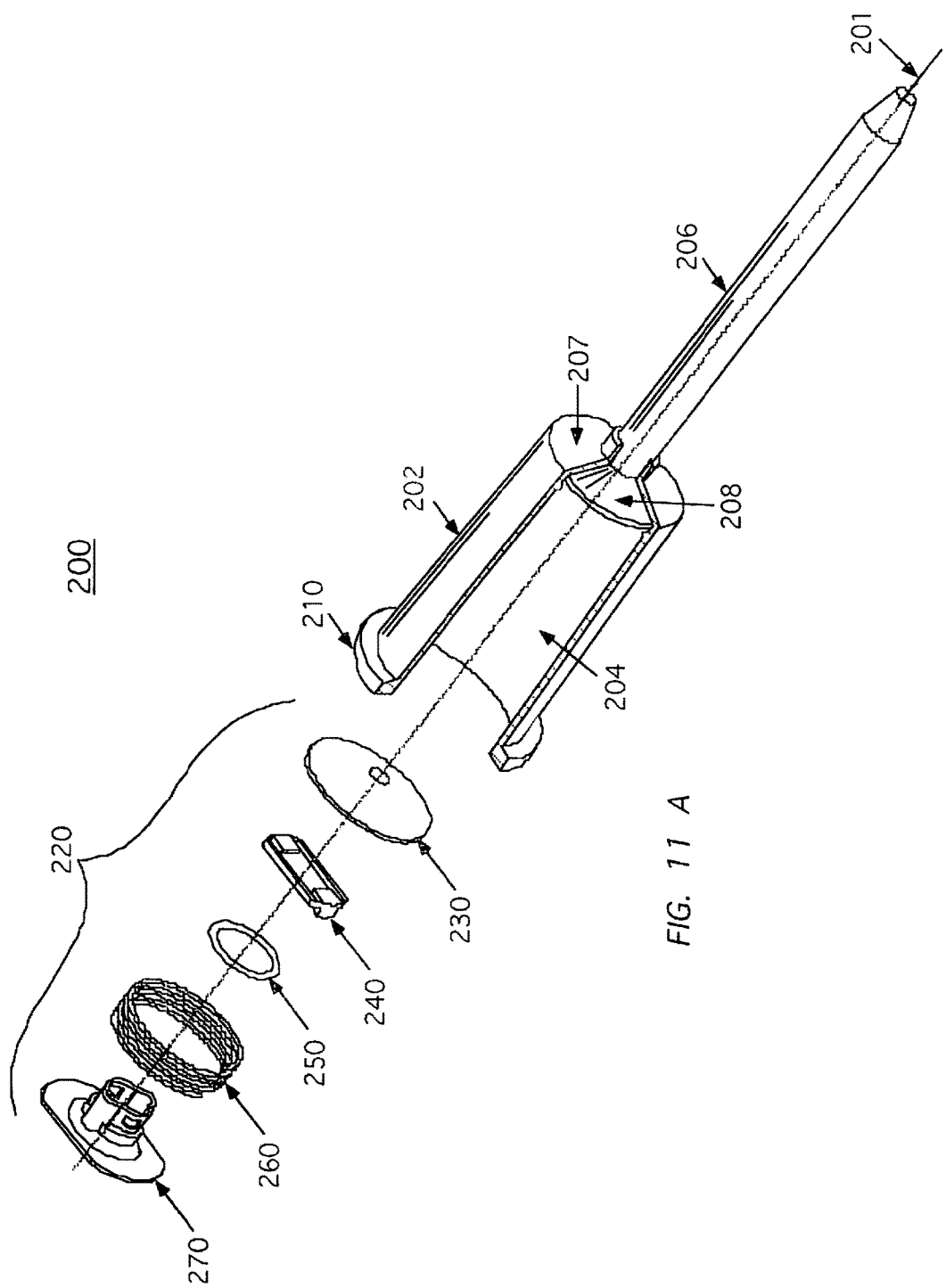
FIG. 11 shows an exploded isometric view of an IV catheter without a needle according to another implementation.

FIG. 11A is an isometric exploded view of an IV catheter 200 without the introducer needle according to another implementation. The IV catheter includes a catheter hub 202 having an internal cavity 204 that is in fluid communication with an elongate polymeric catheter tube 206 that extends distally from a base 207 of the catheter hub. As will be discussed in more detail below, according to one implementation the proximal end portion of the catheter tube 206 is secured to the catheter hub 202 by use of a ferrule 208 on which the proximal end of the catheter tube is press-fit.

The catheter hub 202 has at its proximal end a proximal luer flange 210 for attaching a luer-lock fitting. According to one implementation the proximal luer flange 210 is configured to facilitate an attachment of a male luer fitting to the catheter hub 202 is a manner like that shown in FIGS. 3A, 7 and 18.

The IV catheter 200 has a longitudinal axis 201 and includes a valve assembly 220 that comprises a valve plug 230, a valve clamp 240, a restraining element 250, a spring 260 and a valve actuator 270. In use, the valve assembly components function together to regulate the opening and closing of a valve element to respectively permit ef or prevent the passage of fluids therethrough. To this end, according to one implementation, the valve assembly 220 is transitional from a first open position to a closed position, and is thereafter transitional between the closed position and a second open position.

Figure 12:
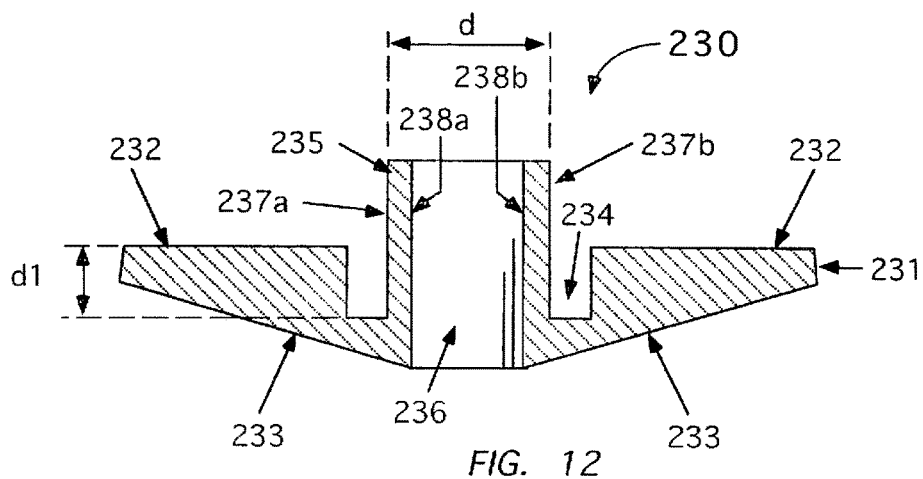
FIG. 12 is a cross-sectional side view of a valve plug according to another implementation.

FIG. 12 illustrates a cross-sectional side view of the valve plug 230 according to one implementation. The valve plug 230 includes a base 231 having proximal facing wall 232 and a distal facing wall 233. The proximal facing wall 232 includes a ring-shaped recess or annularly configured cavity 234 that circumferentially surrounds tubular projection 235 that extends proximally from the base 231. According to one implementation the tubular projection 235 is circular, and together with the base 231 includes a passage 236 that extends through the valve plug 230. The tubular projection 235 includes opposing outer walls 237a and 237b, and opposing inner walls 238a and 238b.

According to one implementation at least the tubular projection 235 is made of an elastomer that enables the opposing outer walls 237a and 237b to be radially pressed toward one another to cause the opposing inner walls 238a and 238b to come together in a manner that closes passage 236. The tubular projection 235 is configured such that when the outer walls 237a and 237b are not being pressed upon, the passage 236 resumes a full or partial open configuration. According to one implementation the entirety of the plug 230 is made of an elastomer.

According to one implementation the tubular projection 235 is made of a first material and the remainder of the plug is made of a second material that has a durometer greater than that of the first material. According to another implementation the tubular projection 235 and plug base 231 are two separate pieces that can be bonded together.

According to one implementation the plug 230 is unitarily formed (i.e. made of a single piece) by, for example, a molding process.

Figure 13A:
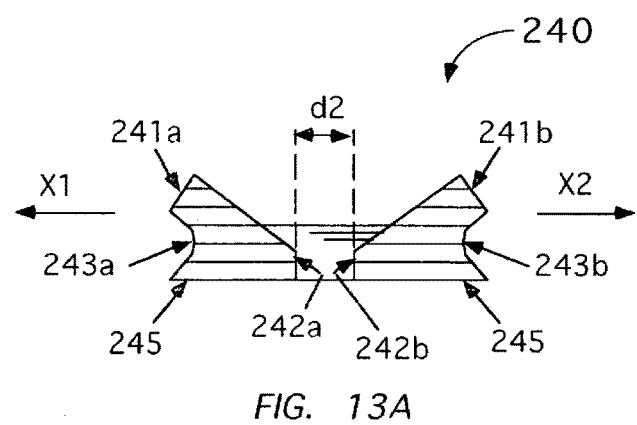
FIG. 13A is a cross-sectional side view of a valve clamp in a non-radially expanded state according to one implementation.
Figure 13B:
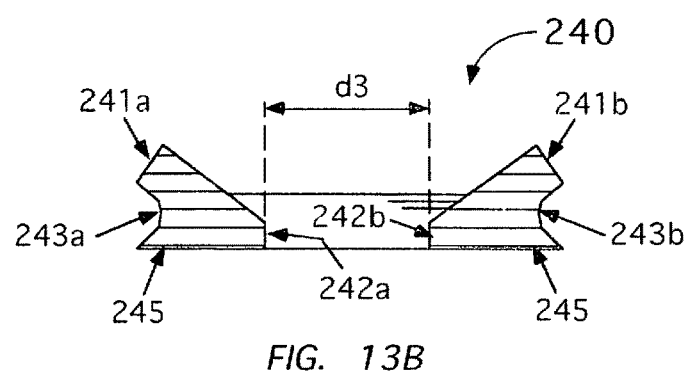
FIG. 13B is a cross-sectional side view of the valve clamp in a radially expanded state according to one implementation.

FIGS. 13A and 13B shows a cross-sectional side view of the valve clamp 240 according to one implementation. According to one implementation the clamp 240 is made of an elastomer and includes first and second opposing arms 241a and 241b. Each of arms 241a and 241b respectively includes an inner clamping surface 242a and 242b. According to one implementation the outer contour of each of arms 241a and 241b respectively includes an indentation 243a and 243b to accommodate a placement and retention of the resilient member 250 about the arms 241a and 241b.

FIG. 13A shows a cross-section view of clamp 240 in a rest state with the distance d2 separating the inner clamping surfaces 242a and 242b being less than the outer diameter d of the tubular projection 235 of plug 230. The valve clamp 240 is configured to expand radially outward to increase the distance between the clamping surfaces 242a and 242b when forces in the directions of $X_1$ and $X_2$ are respectively applied to arms 241a and 241b.

FIG. 13B shows a cross-section view of the valve clamp 240 in a stressed state when the forces in the $X_1$ and $X_2$ directions are applied to the arms 241a and 241b. In the stressed state the clamp 240 elongates in the directions $X_1$ and $X_2$ to cause the distance d3 between the clamping surfaces 242a and 242b to be greater than or equal to the diameter d of the tubular projection 235 of the plug 230.

Figure 15A:
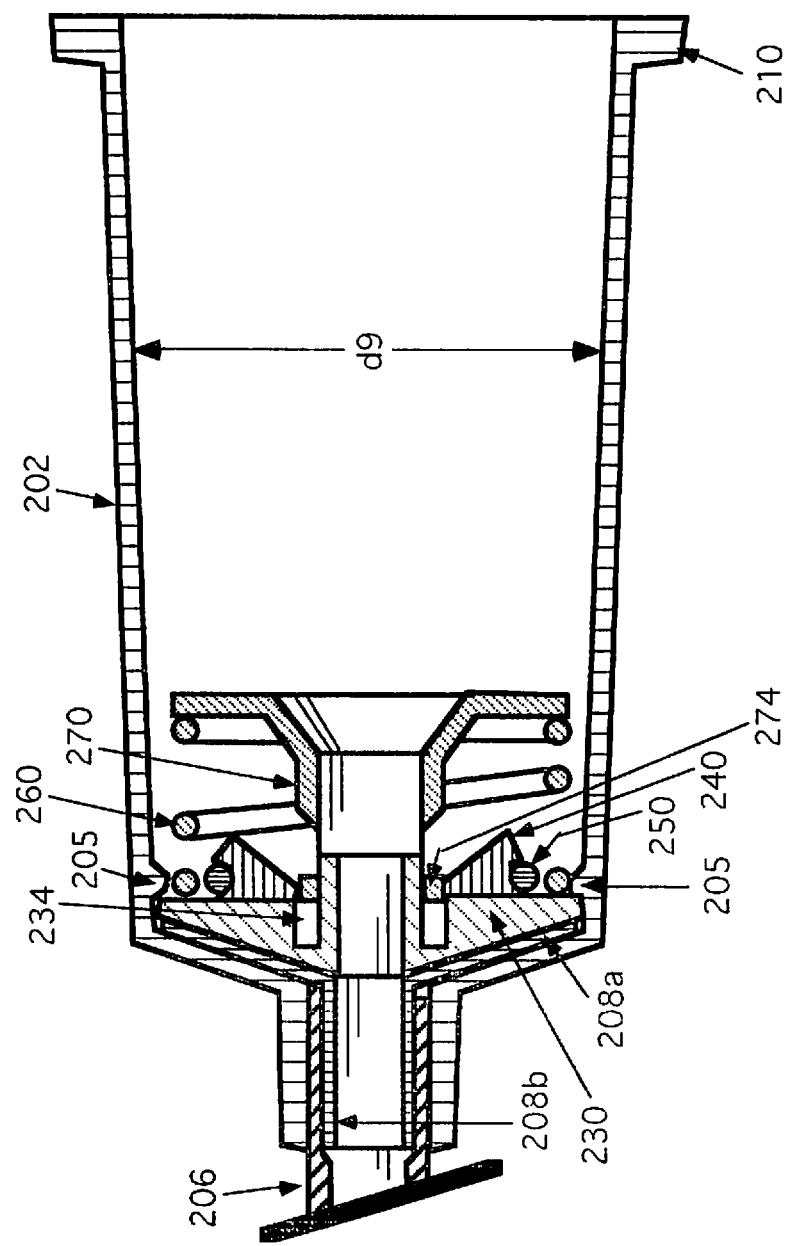
FIG. 15A shows a cross-sectional side view of a luer-activated valve having an axial through-hole with a clamping device in a first, retained position within an IV catheter hub before a needle is coaxially introduced into the IV catheter.
Figure 15B:
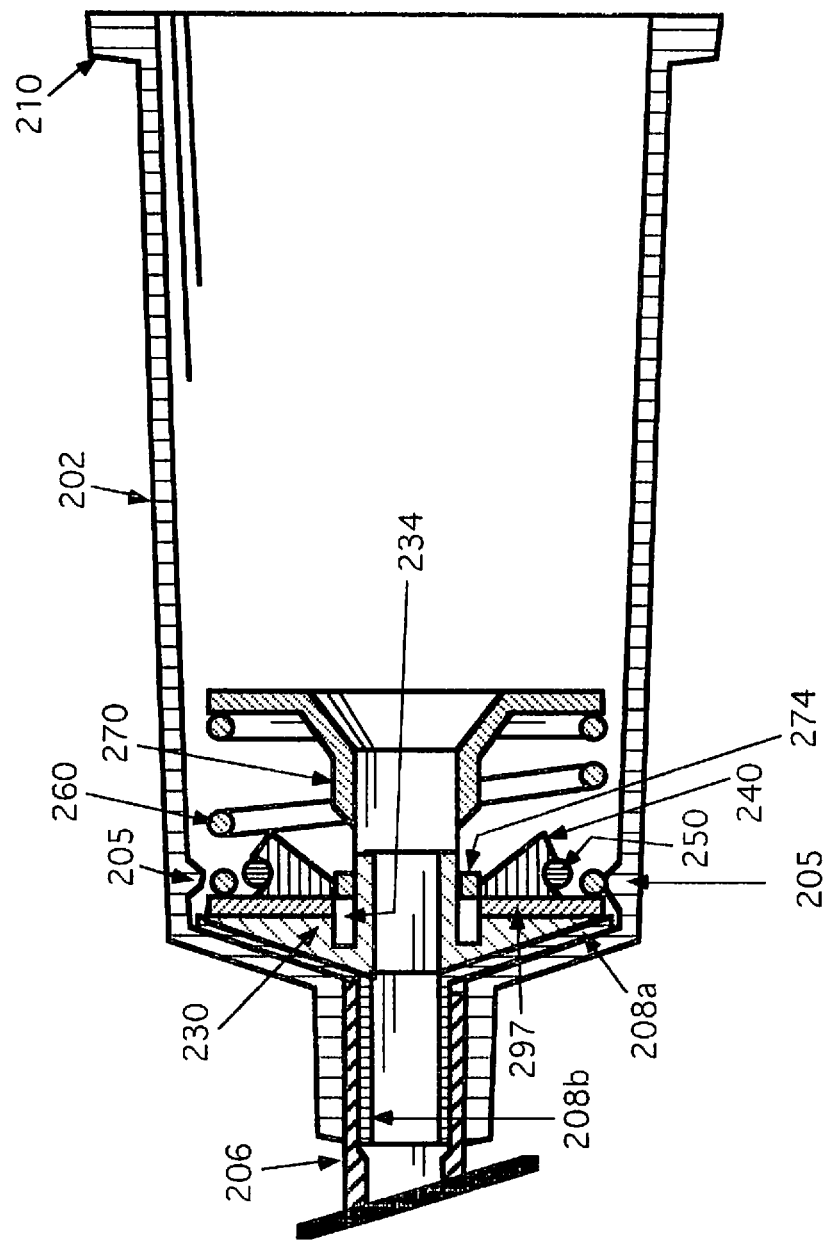
FIG. 15B shows a cross-sectional side view of the luer-activated valve of FIG. 15A having an annular rigid plate disposed between the clamp member and the proximal facing wall of the valve plug.
Figure 16:
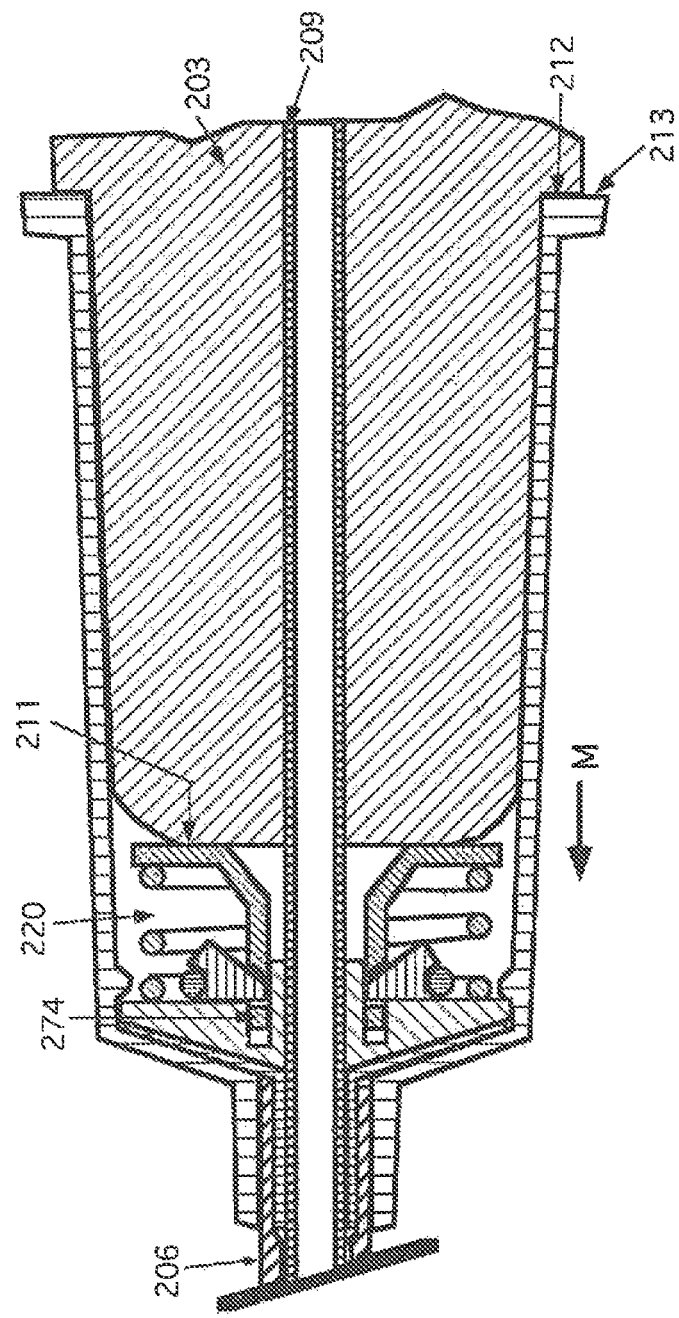
FIG. 16 shows a cross-sectional side view of a needle coaxially located in the luer-activated valve of FIG. 15A in a second, retained position placing a clamping force on a resilient elongate tube through which a needle passes.
Figure 17:
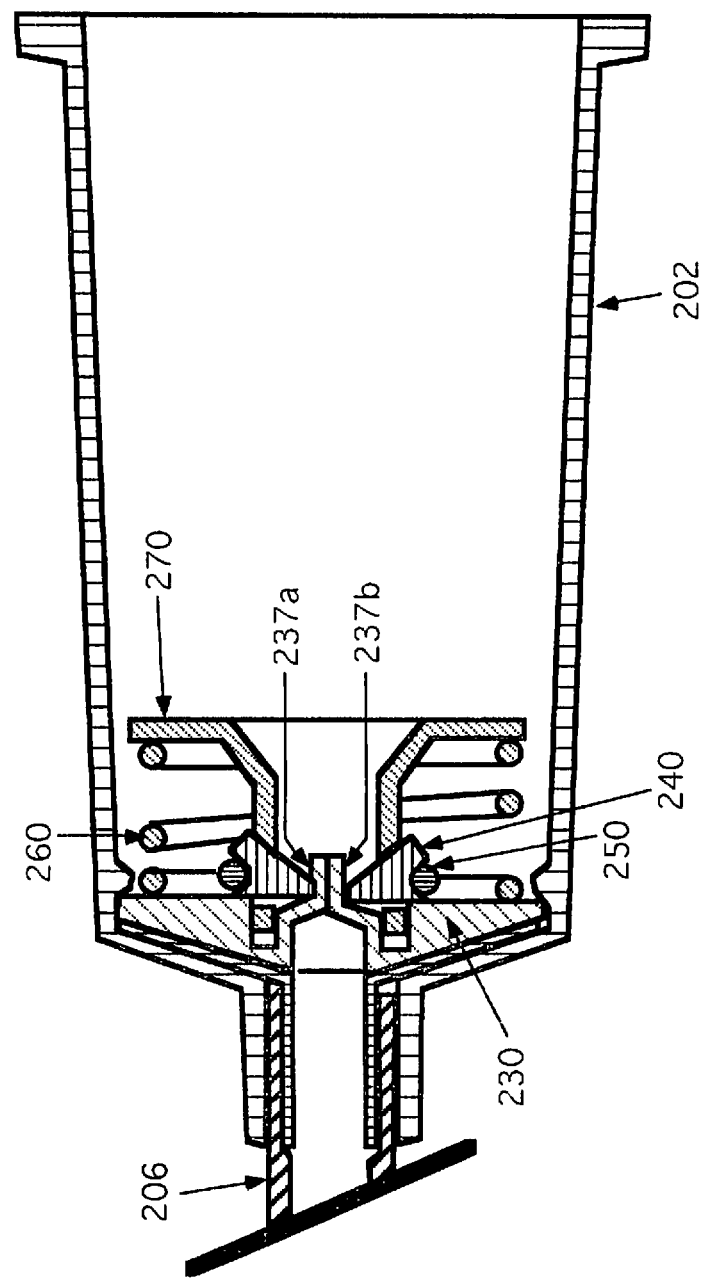
FIG. 17 shows a side view of the luer-activated valve shown in FIG. 15A in a third position (i.e. closed position) having a closed fluid path.

In use, the valve clamp 240 resides positioned about the tubular projection 235 of the plug 230. When the valve clamp 240 is in the rest state the clamping surfaces 242a and 242b respectively press inward against the outer walls 237a and 237b of the tubular projection 235 to cause the outer walls to deform radially inward sufficiently to cause a coming together of the inner walls 238a and 238b as shown in FIG. 17. The coming together of the inner walls 238a and 238b causing a closure of the passage 236. Thereafter, the inner walls 238a and 238b of the tubular projection 235 may automatically expand outward, due to their elasticity, to cause a full or partial opening of the passage 136. This is accomplished by respectively applying forces to the arms 241a and 241b of the clamp 240 in the $X_1$ and $X_2$ directions to cause the distance d2 between the clamping surfaces 242a and 242b to be greater than or equal to the diameter d of the tubular projection 235 of the plug 230. FIGS. 15A, 15B and 16 respectively show the valve 220 in first and second open positions with the clamp 240 being in a stressed state. FIG. 17 shows the valve 220 in the closed position when the clamp 240 is in a rest state.

In regard to the present disclosure, the term "rest state" encompasses any state of the clamp 240 whereby the distance between the clamping surfaces 242a and 242b is less than the outer diameter d of tubular projection 235 of the plug 230.

In addition, although the tubular projection 235 has thus far been described as having a diameter, other configurations are possible. For example, the tubular projection 235 may have a rectangular outer profile and a rectangular inner profile that defines the passage 236. In such instances, the notation "d" in FIG. 12 represents the distance between the outer walls 237a and 237b and not a diameter.

According to some implementations, to enhance the closing capability of the valve clamp 240, a resilient member 250 is disposed about the valve clamp 240 in a manner that continuously urges the clamping surfaces 241a and 241b inwardly toward one another. As noted above, according to one implementation the outer profile of the valve clamp 240 includes on each side a recess 243a and 243b in which at least portions of the resilient member 250 are retained.

As will be discussed in detail below, the valve actuator 270 is used to alter the state of the valve clamp 240 for the purpose of opening and closing the valve 220. In doing so, the actuator 270 is arranged in the valve assembly 220 with freedom of axial movement along the longitudinal axis 201 in both a distal direction and a proximal direction.

Arranged in the valve assembly 220 is spring 260 that is configured to urge the actuator 270 in the proximal direction. According to one implementation the spring is a coil spring made of a resilient polymeric or metal material.

FIGS. 14A-D show various views of the actuator 270 according to one implementation. The actuator 270 includes a proximal flange 271 having a central opening 272. Extending distal from the proximal flange 271 is a prolongation 273. According to one implementation a proximal end portion 273a of the prolongation 273 is funnel-shaped and includes a through opening that communicates the flange opening 272 with a keyhole type opening 275 located in a distal end portion 273b of the prolongation. The opening 275 need not be keyhole-shaped and may include an oblong configuration 275a-b and any shaped opening that can accommodate a widening of the tubular projection 235 of the valve plug 230 when it is clamped between the clamping surfaces 242a and 242b of clamping member 240 as will be discussed in detail below.

Figure 14D:
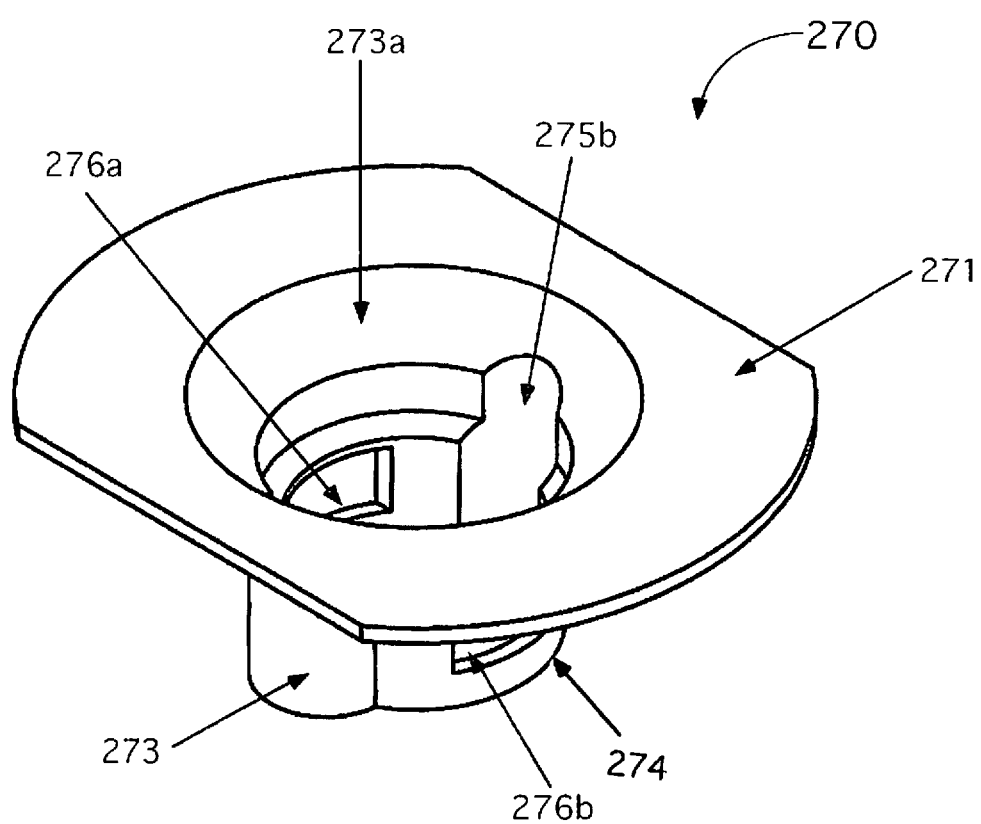
FIG. 14D is an isometric view of the valve actuator of FIGS. 14A and 14B.

According to one implementation, a distal-most end portion of the prolongation 273 includes an annular segment 274 having a length L that is equal to or less than the depth d1 of the recess 234 located in plug 230. It is important to note that segment 274 need not be annular, and may include other configurations. One such configuration is shown in FIG. 14D wherein the segment 274 possesses a key-shaped outer profile. In any event, according to some implementations, the shape of the recess 234 in the valve plug 230 generally corresponds to the shape/outer profile of the distal-most segment 274 of the valve actuator prolongation 273. According to some implementations, like those shown in FIGS. 14A-D, the outer profile of the distal-most segment 274 is non-circular in order to prevent a rotation of the actuator 270 inside recess 234.

Located proximal to the distal-most segment 274, and located in opposing sides of the distal end portion 273b of the prolongation, are first and second side openings 276a and 276b. Each of the first and second side openings 276a and 276b provides a side passage into the internal longitudinal opening 275 of the distal end portion 273b of the prolongation. The first and second side openings 276a and 276b are respectively sized to accommodate a passage of the arms 241a and 241b of the clamp member 240 into and out of the internal longitudinal opening 275 of the distal end portion 273b of the prolongation 273, as will be described in detail below.

Located proximally adjacent to the first and second side openings 276a and 276b of the prolongation there respectively includes first and second external inwardly tapered walls 277a and 277b. As will be described in more detail below, in use, the valve actuator 270 moves proximally and distally in the direction X as shown in FIG. 14B. The first and second external tapered walls 277a and 277b are configured to respectively act on the arms 241a and 241b of the clamp member 240 to cause an incremented radial separation of the clamp arms from the positions shown in FIG. 13A to the positions shown in FIG. 13B.

Figure 14E:
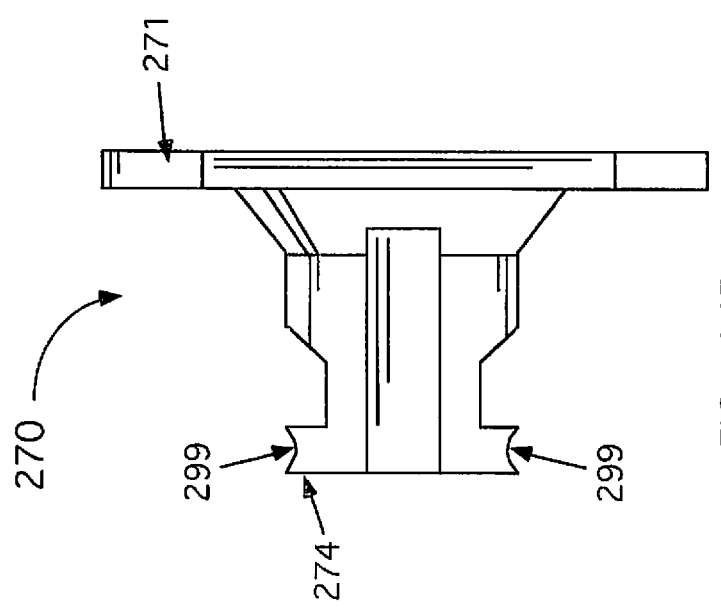
FIG. 14E is a side view of an actuator according to another implementation.

According to some implementations, as shown in FIG. 14E, outer walls of the distal segment 274 of the actuator 270 comprise one or more indentation 299. As will be discussed in more detail below, the one or more indentations 299 are configured to assist in holding the inner surfaces of clamp 240 on the actuator 270 when the valve assembly 220 is in its first operational state.

In the implementation shown in FIG. 14E the one or more indentations 299 have a concaved shape but may possess other shapes that are sufficient for holding the inner surfaces of clamp 240 on the actuator 270 when the valve assembly is in its first operational state. It is important to note that the implementation of FIG. 14D is applicable to all implementations disclosed herein that comprise an actuator.

FIG. 15A shows a partial cross-sectional side view of IV catheter 200 with the valve assembly 220 positioned inside the catheter hub 202. The catheter tube 206 is coupled to the distal end of the catheter hub 202 by being fitted over an elongate portion 208b of the ferrule 208. According to one implementation the ferrule includes a first segment 208a that fits flush against an inner wall of the base 207 of the catheter hub 202. According to one implementation, like that shown in FIG. 15A, the distal facing wall 233 of the valve plug 230 in turn fits flush against the proximal side of the ferrule 208.

According to some implementations the valve plug 230 is held in place inside the catheter hub 202 only as a result of being press-fit in the distal end of the catheter hub 202. According to other implementations the valve plug 230 is secured inside the catheter hub 202 by use of an adhesive. According to some implementations, as shown in FIG. 15A, one or more lips 205 protrude inward from the inner wall of the catheter hub 202 and function to hold or assist in holding the valve plug 230 in place.

As described previously in conjunction with the implementation of FIG. 1, prior to use, the IV catheter includes an introducer needle. The introducer needle is attached to a needle hub that is fixed to the catheter hub via a luer connection. In the "ready to use" state the introducer needle extends through the catheter hub and into the catheter tube with the sharpened distal tip of the needle protruding distally from the catheter tube as shown in FIG. 1. The use of an introducer needle applies to each of the IV catheter implementations disclosed herein.

FIG. 15A shows the IV catheter 200 prior to the introducer needle being introduced therein. In FIG. 15A the valve assembly is shown in a first operational state that allows the introducer needle to freely pass through the valve 220 and into the inner lumen of the catheter tube 206 during an assembly of the introducer needle into the IV catheter. In this first operational state, as with all operational states of the valve assembly, a spring 260 may be held between a distal face 278 of the valve actuator flange 271 and the proximal facing wall 232 of the valve plug 230.

In regard to each of the operational states of the IV catheter shown in FIGS. 15A-18, according to some implementations the distal surface 245 of the clamp member 240 is positioned on the proximal facing wall 232 of the valve plug 230. According to other implementations a rigid annular plate or film 297 is disposed between the distal surface 245 of the clamp member 240 and the proximal facing wall 232 of the valve plug 230 as shown, for example, in FIG. 15B. According to some implementations the film may comprise a lubricious film applied to the proximal facing wall 232 of the valve plug 230.

According to some implementations the main body of the plug 230 is made of a first material having a first durometer and the annular plate 297 is made of a second material having a second durometer that is greater than the first durometer. According to some implementations the proximal facing surface of the annular plate 297 has a first surface roughness and the proximally facing wall 232 of the main body of the plug 230 has a second surface roughness that is greater than the first surface roughness.

As explained above, according to one implementation, the clamp member 240 is made of a resilient material and is arranged in the valve assembly 220 such that the clamping surfaces 242a and 242b are continuously urged toward one another. Disposed between the clamping surfaces 242a and 242b is the tubular projection 235 of the valve plug 230. Hence, when the clamping surfaces 242a and 242b are not being held apart by the actuator 270, they are free to move radially inward toward one another to respectively press against the outer walls 237a and 237b of the tubular projection 235 of the valve plug 230. As explained above, a resilient member 250 may be positioned about the clamp member 240 to act on the clamping arms 241a and 241b to provide an additional force for urging the inner walls 238a and 238b of the tubular projection 235 into contact with one another to effectuate a closing of the valve 220.

According to one implementation spring 260 is a coil spring that includes a distal-most coil 261 that is positioned between the outer peripheral surface of resilient member 250 and an inner surface of catheter hub 202 as shown in FIGS. 15A-18.

In the first operational state of FIG. 15A, the actuator 270 is in a first axial position with the distal segment 274 of the actuator 270 being disposed between the clamping surfaces 242a and 242b and the tubular projection 235 of the valve plug 230, preventing the clamping surfaces 242a and 242b from pressing against the tubular projection. As a result, a through passage is provided through the valve assembly 220 to enable an introduction of the introducer needle 209 into the IV catheter 200 allowing the needle to be threaded through the valve passageway during the assembly process without the need for a mandrel to open the passageway. The open passageway allows the needle bevel to move through the passageway without being damaged. FIG. 16 shows the introducer needle 209 assembled in the IV catheter 200. According to one implementation the diameter d4 of the distal segment 273b of the prolongation 273 is greater than the diameter d of the tubular projection 235 of the valve plug 230.

FIG. 16 shows the IV catheter 200 in a second operational state with the actuator 270 located in a second axial position distal to the first axial position. The second operational state corresponds to the "ready to use" state discussed above. When the actuator 270 is in the second axial position, the distal end segment 274 of the prolongation 273 resides inside the recess 234 of the valve plug 230 allowing the clamping surfaces 242a and 242b of the clamp member 240 to move radially inward to press against the outer walls 237a and 237b of the tubular projection 235. Because the introducer needle 209 resides inside the tubular projection 235, the tubular projection substantially maintains its tubular form when the actuator 270 is in the second axial position.

As shown in FIG. 16, the introducer needle 209 is affixed to a needle hub 203 that resides inside the cavity 204 of the catheter hub 202. When the introducer needle 209 is assembled in the IV catheter 200, the distal end surface 211 of the needle hub 203 is caused to press against the flange 271 of the actuator 270 to cause the actuator to move from the first axial position to the second axial position. During the assembly process the needle hub 203 is moved distally in the direction M. According to one implementation the needle hub 203 is equipped with a stop 212 that engages with a part of the catheter hub 202 to limit the distal advancement of the needle hub into catheter hub to ensure or prevent the actuator 270 from being moved distally beyond the second axial position. In the example of FIG. 16 the stop 212 comprises one or more radially extending protrusions that are configured to act against a proximal end surface 213 of the catheter hub 202. According to one implementation the stop 212 constitutes threaded part of the needle hub 203 that is configured to cooperate with the proximal luer flange 210 of the catheter hub 202 to achieve a fixation of the needle hub with the catheter hub.

According to some implementations, not shown in the figures, the IV catheter 200 is equipped with a needle guard that is used to cover the distal sharpened tip of the introducer 209 upon its removal from the IV catheter. According to some implementations, the needle guard is disposed between the needle hub 203 and the actuator 270, and may in some instances transmit the force applied by the needle hub to the actuator during an assembly of the introducer needle 209 into the IV catheter.

With the IV catheter 200 in the "ready to use" state the clinician may introduce the catheter tube 206 into a vessel of a patient by puncturing the skin of the patient and also the wall of the vessel with the sharpened distal tip of the introducer needle 209 followed by an introduction of the distal end of the catheter tube 206 into the vessel. Upon the catheter tube 206 being successfully introduced into the vessel, the introducer needle is removed entirely from the IV catheter by disconnecting the needle hub from the catheter hub and withdrawing the needle 209 proximally.

When the introducer needle 209 is removed from inside the tubular projection 235 of the valve plug 230, the forces exerted by clamping surfaces 242a and 242b are capable of causing the outer walls of the tubular projection 235 to collapse causing the coming together of the opposing inner walls 238a and 238b to effectuate a closing of the valve as shown in FIG. 17. The configuration of FIG. 17 represents a third operational state of the IV catheter 200.

As discussed above, according to some implementations the actuator 270 includes a keyhole-shaped opening 275. The keyhole-shaped opening includes a central opening and first and second lobes 275a and 275b that protrude from opposite sides of the central opening. According to some implementations, when the tubular projection 235 of the valve plug 230 widens when being clamped, portions of the tubular projection extend outward from the central opening and into the first and second lobes 275a and 275b. According to some implementations the central opening has a circular shape and the lobes are defined by curved walls.

Figure 18:
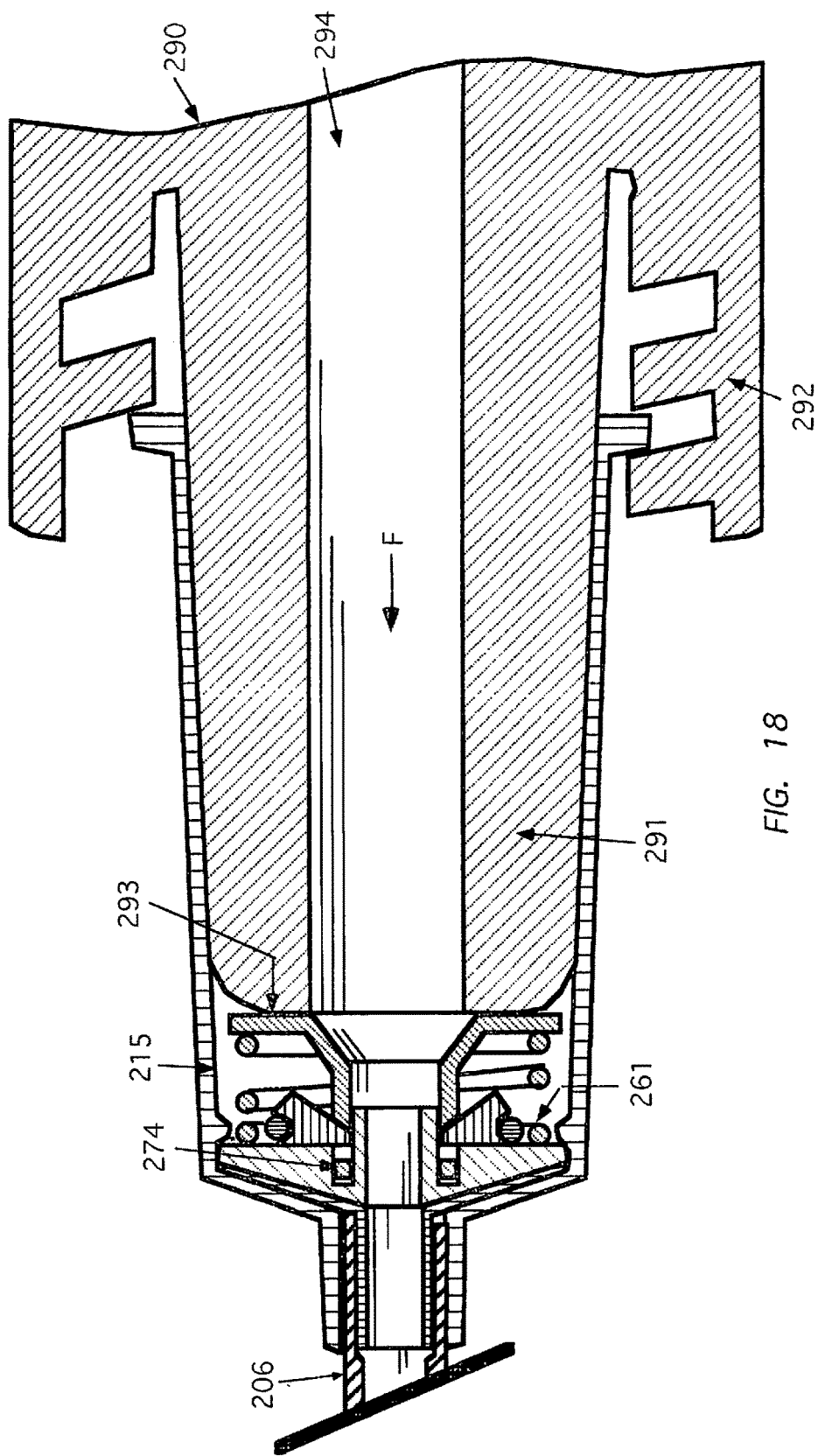
FIG. 18 shows a side view of the luer-activated valve shown in FIG. 15A in a fourth position having an unobstructed fluid path when a luer connector is placed within the IV catheter hub.

When the IV catheter 200 is in the third operational state it is poised to receive a luer connector 290 as shown in FIG. 18 to facilitate an infusion of a therapeutic fluid into the vessel of the patient. In FIG. 18 the IV catheter 200 is shown in a fourth operational state. The luer connector 290 typically includes an elongate body 291 that extends into the cavity 204 of the catheter hub 202 as shown in FIG. 18. The luer connector 290 includes a threaded part 292 that is configured to cooperate with the proximal luer flange 210 of the catheter hub 202 to lock the luer connector in a fixed position inside the catheter hub 202 when the IV catheter is in the fourth operational state. As the luer connector 290 is advanced distally into the cavity of the catheter hub 202, at some point its distal end wall 293 makes contact with the proximal flange 271 of the actuator 270 and applies a force F to the actuator to cause the actuator to move in a distal direction to assume a third axial position as shown in FIG. 18. As the actuator 270 is moved distally toward the third axial position, the first and second external tapered walls 277a and 277b respectively engage the arms 241a and 241b of the clamp member 240 to cause the clamping surfaces 242a and 242b to disengage with the outer walls of the tubular projection 235 of the valve plug 230 to effectuate an opening of the valve 220. Thereafter, the through passage 236 of the valve plug 230 communicates a through passage 292 of the luer connector 290 with the inner lumen of the catheter tube 206 to enable a therapeutic agent to be administered into the vessel of the patient.

Figure 19C:
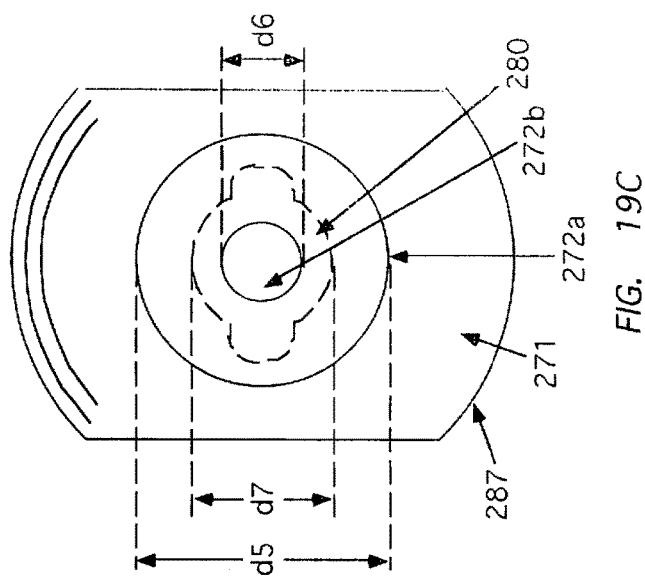
FIG. 19C is a proximal end view of the actuator shown in FIGS. 19A and 19B.
Figure 19B:
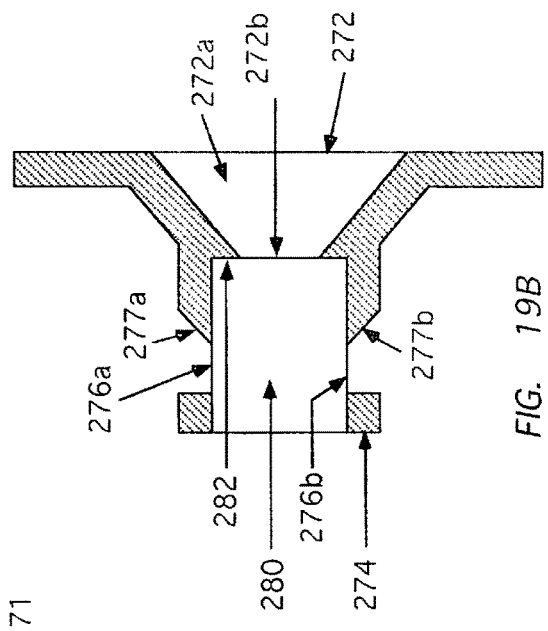
FIG. 19B is a cross-sectional side view of the valve actuator of 19A.
Figure 19A:
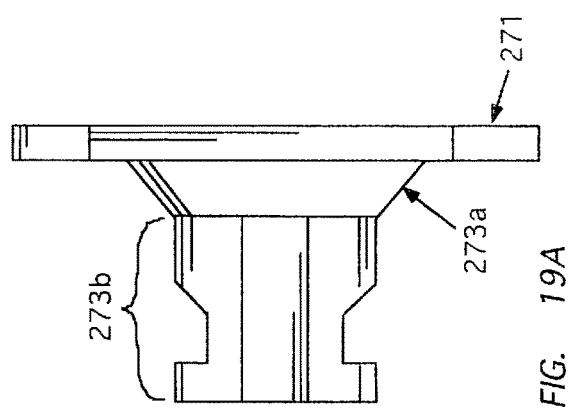
FIG. 19A shows a side view of a valve actuator according to another implementation.

FIGS. 19A-C depict a valve actuator according to another implementation. The actuator is similar in construction to the actuator described above in conjunction with the FIGS. 14A-E with the exception that a portion of the through passage extending through a central region of the actuator is designed to have a diameter d7 that is less than the outer diameter d of the tubular projection 235 of the valve plug 230. The funnel-shaped flange opening 272 has a proximal opening 272a having a diameter d5 and a distal opening having a diameter d6 which is less than d5. In addition, the opening 280 that extends across a length of the distal segment 273b of the prolongation 273 has a diameter d7 that is greater than diameter d6 and less than or equal to diameter d5. As a result of the diametric dissimilarities an inner shoulder 282 is formed at the juncture of openings 272 and 280 as shown in FIG. 19B.

Figure 20:
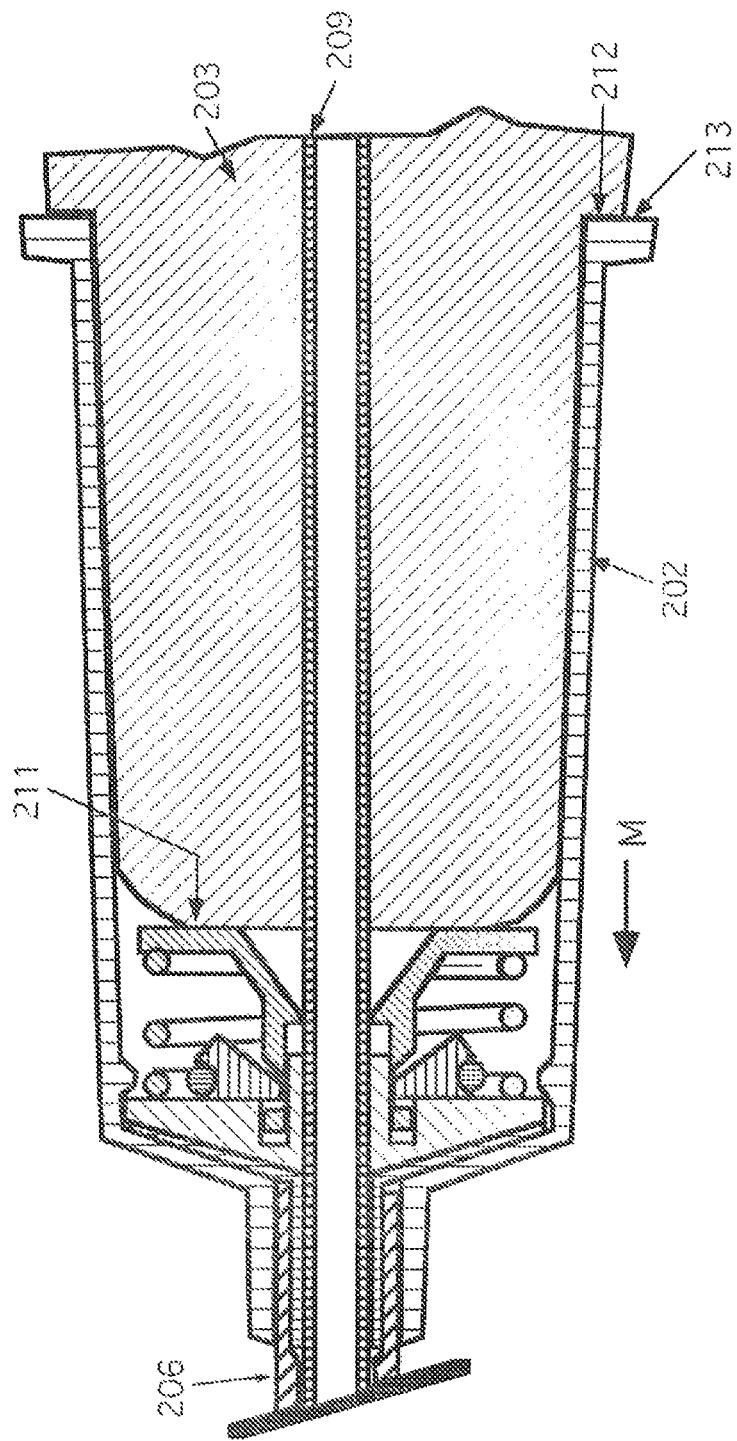
FIGS. 20 and 21 show an IV catheter in different operational states that incorporate the actuator of FIGS. 19A-C.
Figure 21:
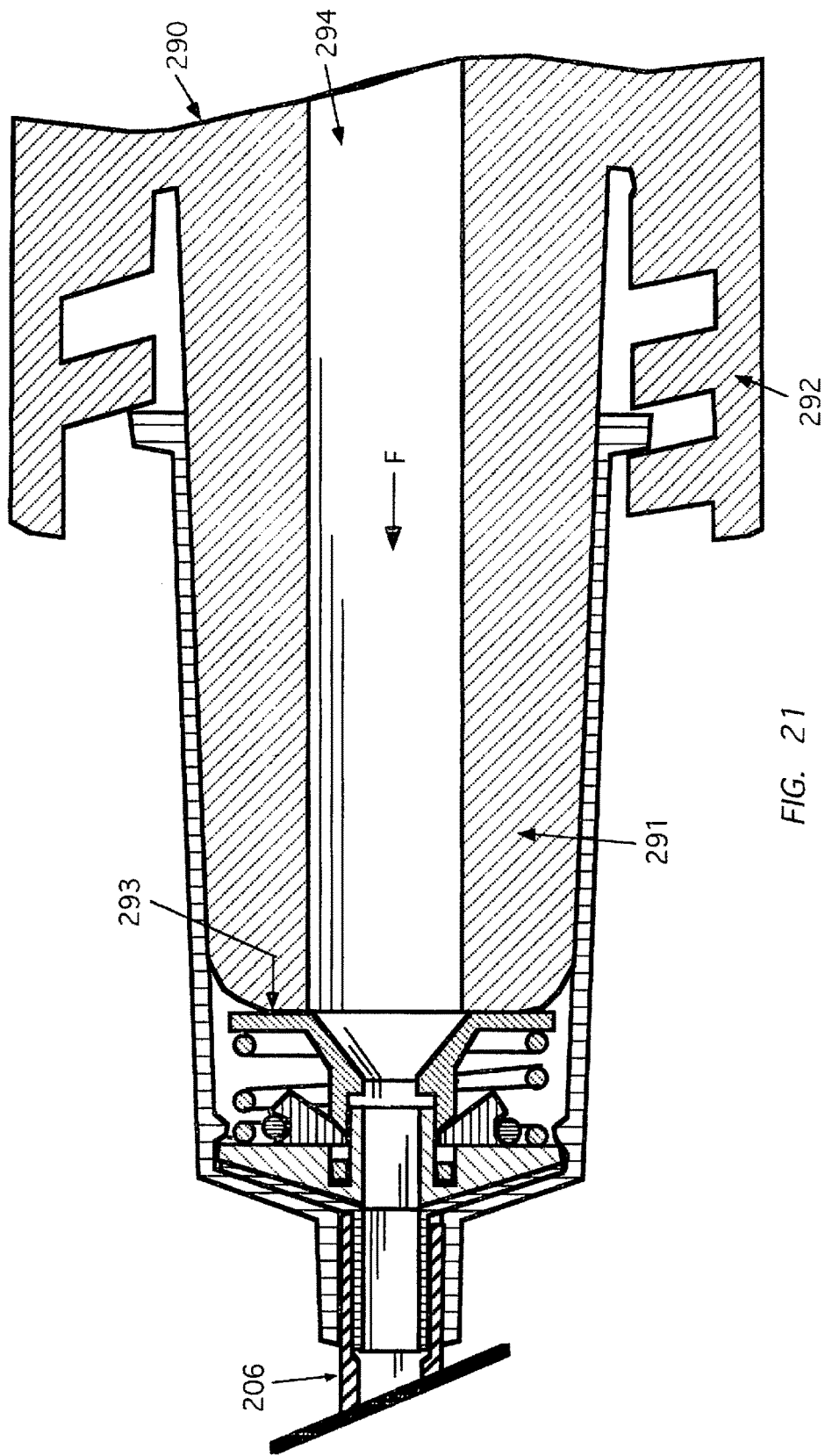

FIGS. 20 and 21 respectively show the IV catheter 200 in the second and fourth operational states and having a valve actuator like that shown in FIGS. 19A-C. In the implementations of FIGS. 20 and 21 the inner diameter d7 of opening 280 is slightly larger than the outer diameter d of the tubular projection 235 of valve plug 230 to create a sliding fit between the actuator and the tubular projection. However, opening 272b at the junction of openings 272 and 280 is less than the inner diameter of the tubular projection 235, and according to some implementations the diameter d6 opening 272a is sized to be slightly larger than the outer diameter of the introducer needle 209 such that a sliding fit exists between the actuator and the outer surface of the introducer needle shaft. The funnel-shaped opening 272 at the proximal end of the actuator in conjunction with the reduced diameter portion 272b operates to guide the introducer needle 209 into and through the valve assembly 220 and to place the introducer needle in concentric alignment with the valve assembly 220.

Figure 22B:
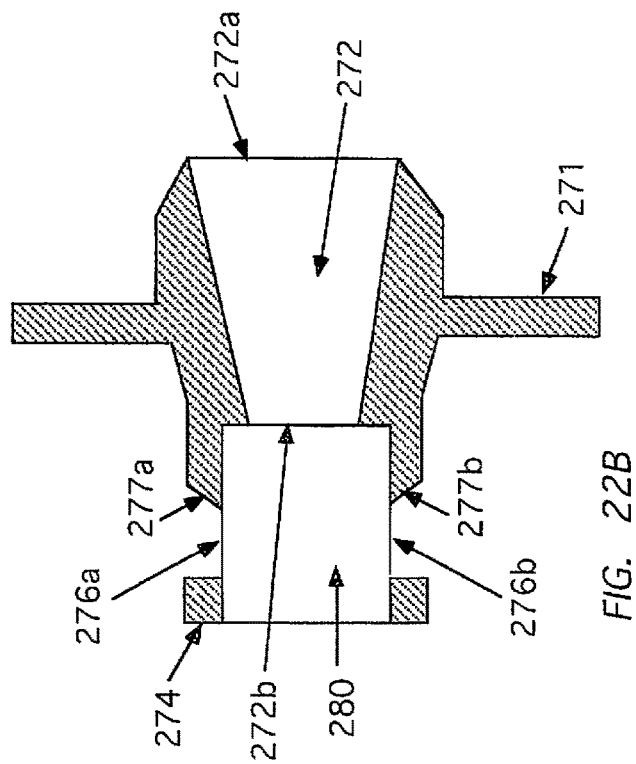
FIG. 22B is a cross-sectional side view of the valve actuator of 22A.
Figure 22A:
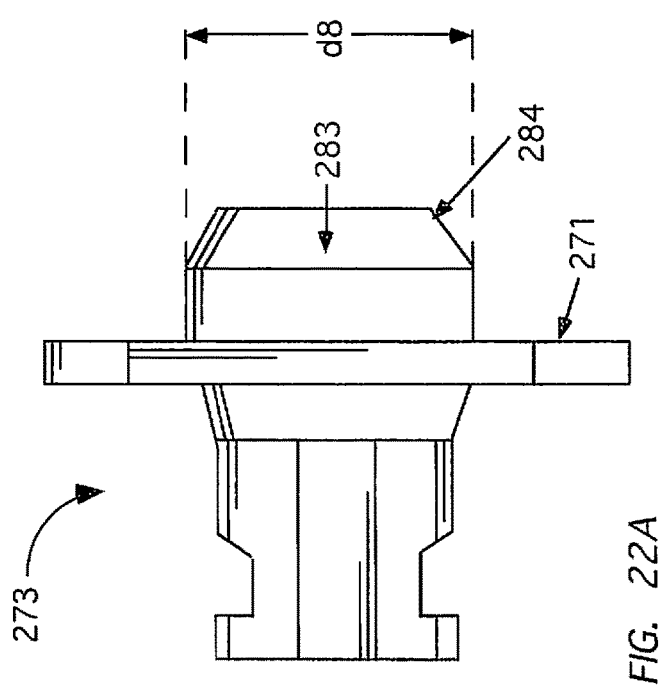
FIG. 22A shows a side view of a valve actuator according to another implementation.
Figure 23:
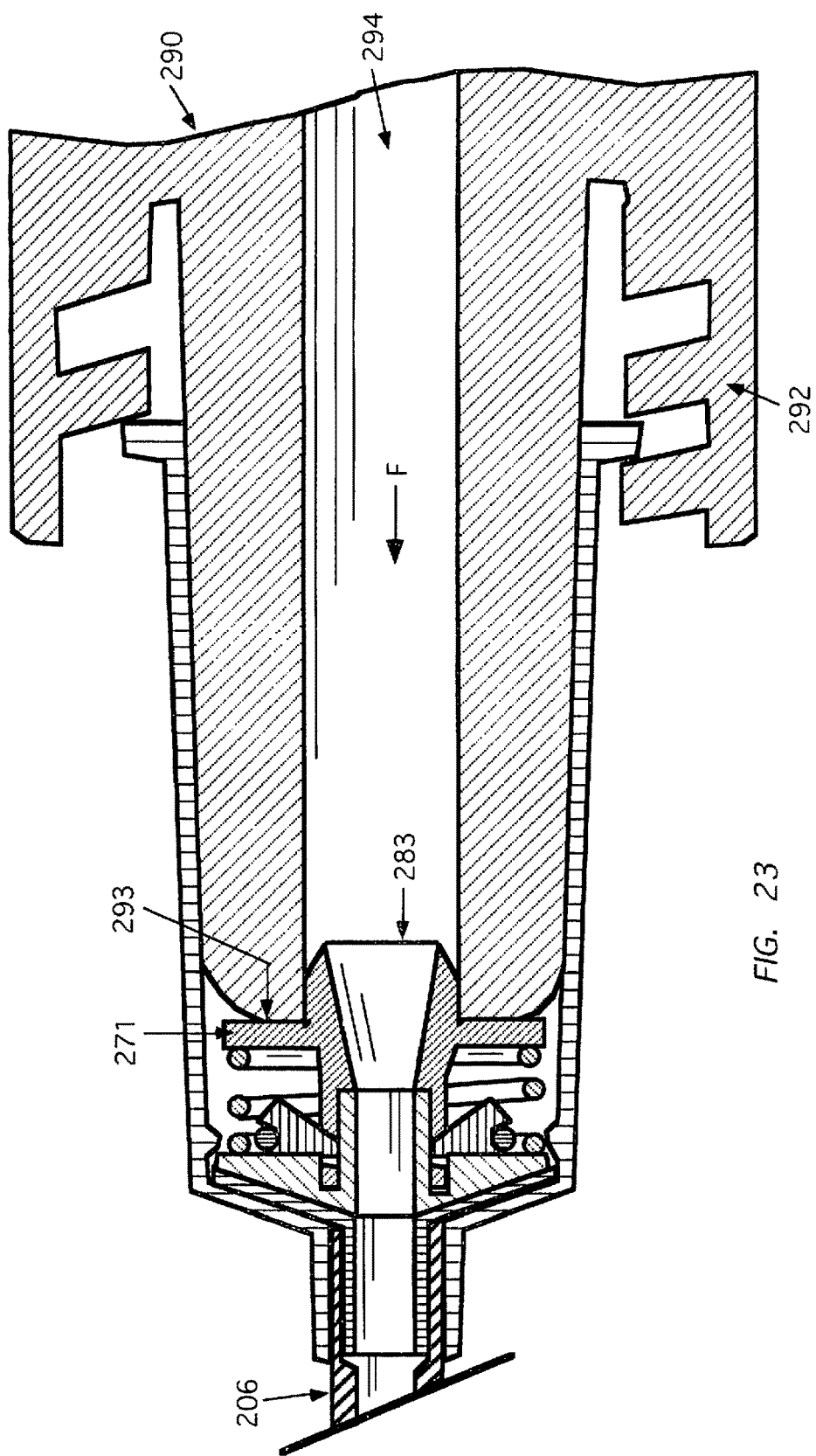
FIG. 23 is a cross-sectional side view of an IV catheter having incorporated therein the valve actuator of FIGS. 22A and 22B.

FIGS. 22A and 22b respectively show a side view and cross-sectional side view of a valve actuator according to another implementation. The actuator is similar in construction to the actuator described above in conjunction with FIGS. 19A-C and additionally includes a proximal projection 283 that projects proximally from the flange 271. In use, when the luer connector 290 is advanced into the catheter hub 202 to place the IV catheter 200 in the fourth operational state, as shown in FIG. 23, the proximal projection 283 functions to concentrically align the luer connector lumen 294 with the valve assembly 220. The proximal end of the projection 283 includes a tapered lead-in 284 to facilitate a mating of the projection 283 inside the lumen of the luer connector. According to one implementation, the outer diameter d8 of the projection 283 is slightly less than the inner diameter of the luer connector lumen 294 such that a sliding fit exists between the inner wall of lumen 294 and the outer wall of projection 283. The concentric alignment of the luer connector 290 with the valve assembly 220 assists in ensuring a more uniform application of force applied by the distal end 293 of the luer connector 290 onto the flange 271 of the actuator. That is, the use of the proximal projection 283 safeguards against there being a skewed relationship between the luer connector and the flange of the actuator which could result in the valve assembly 220 not functioning properly.

In FIGS. 14C and 19C, the flange 271 of the actuator 270 is shown having first and second curved sides 285a and 285b and first and second straight sides 286a and 286b. This configuration may be included in all actuators disclosed herein. In FIGS. 15-18, 20, 21 and 23 the curved ends 285a and 285b of the actuator 272 are shown spaced apart from the inner wall cylindrical wall 215 of the catheter hub 202. According to other implementations the width W of the flange 271, as shown in FIG. 14C, is substantially equal to the inner diameter d9 of the catheter hub 202 at least when the valve assembly 220 is in the fourth operational state in order to produce a close sliding fit between the first and second curved sides 285a and 285b of the flange 271 and the inner wall 215 of the catheter hub 202. According to some implementations the curvature of the first and second curved sides 285a and 285b is the same or substantially the same as the curvature of the inner wall 215 of the catheter hub 202.

According to some implementations the flange 271 has a circular profile in lieu of having curved and straight sides. According to such implementations the diameter of the flange 271 is substantially equal to but less than the inner diameter d9 of the catheter hub 202, at least when the valve assembly 220 is in the fourth operational state, in order to produce a close sliding fit between the first and second curved sides 285a and 285b of the flange 271 and the inner wall 215 of the catheter hub 202. According to some implementations the close sliding fit is sufficient to limit, at least to some degree, a tilting of the flange 271 inside the hub cavity 204.

In FIGS. 15A-18, 20, 21 and 23 the cylindrical inner wall 215 of the catheter hub 202 is shown tapering inward such that a cross-sectional view of the hub cavity 204 is cone-shaped having a truncated distal end. In other words, the inner diameter d9 of the cavity 204 diminishes along the length of the cavity when moving in the distal direction. According to other implementations at least the length of the cavity 204 located proximal to the proximal end of the tubular projection 235 of the valve plug 230 has a uniform inner diameter.

The flange 271 of the actuator 270 has a longitudinal range of motion between a proximal-most position inside the hub cavity 204 when the valve assembly is in the first operational state and a distal-most position inside the hub cavity 204 when the valve assembly is in the fourth operational state. According to some implementations at least the inner diameter of the hub cavity 204 between the proximal-most and distal-most positions is uniform. According to such implementations the width W or diameter of the actuator flange 271 is dimensioned such that the outer perimeter wall 287 of the flange rides along the inner wall 215 of the catheter hub 202 with there being a sliding fit between walls 287 and 215.

In order to prevent a rotation of the actuator 270 inside the catheter hub 202, according to some implementations the outer peripheral wall of the actuator flange 271 is equipped with one or more notches and the inner wall of the catheter hub 202 is equipped with one or more longitudinally extending protuberances fitted respectively inside the one or more notches.

FIGS. 24A-27 illustrate an IV catheter 300 according to another implementations. According to some implementations the IV catheter 300 is similar to the IV catheter 200 depicted in FIGS. 15A-18 except in the construction of the valve assembly 320. The valve assembly 320 includes a valve plug 230 like that described above. The valve assembly also includes a valve actuator 270 like that described above.

The valve assembly 320 differs from valve assembly 220 in that it does not include a separate valve clamp 240 or resilient member 250 or helical spring 260. The valve assembly 320 instead includes a spring element 360 having distal first and second clamping segments 361a and 361b that are configured to move radially inward and outward to respectively effectuate an opening and closing of the tubular projection 235 passage way. The spring clip 360 is held between the distal face 278 of the valve actuator flange 271 and the proximal facing wall 232 of the valve plug 230. The spring clip element 360 includes a proximal end segment 362 that is configured to be acted upon by the actuator flange 271 in order to cause the valve assembly 320 to assume various operational states like the first, second, third and fourth operational states described above. Additionally, the valve may operate multiple times between the third and fourth operational positions providing multi-cycle use. Like spring 260 disclosed above, the spring is assembled in valve assembly 320 such that the spring clip 360 continuously urges the actuator 271 in the proximal direction at least in the second, third and fourth operational states. The proximal end segment 362 of the spring clip 360 includes first and second ends 362a and 362b that are respectively coupled to the first and second clamping segments 361a and 361b by first and second crossing arms 363a and 363b.

Figure 24A:
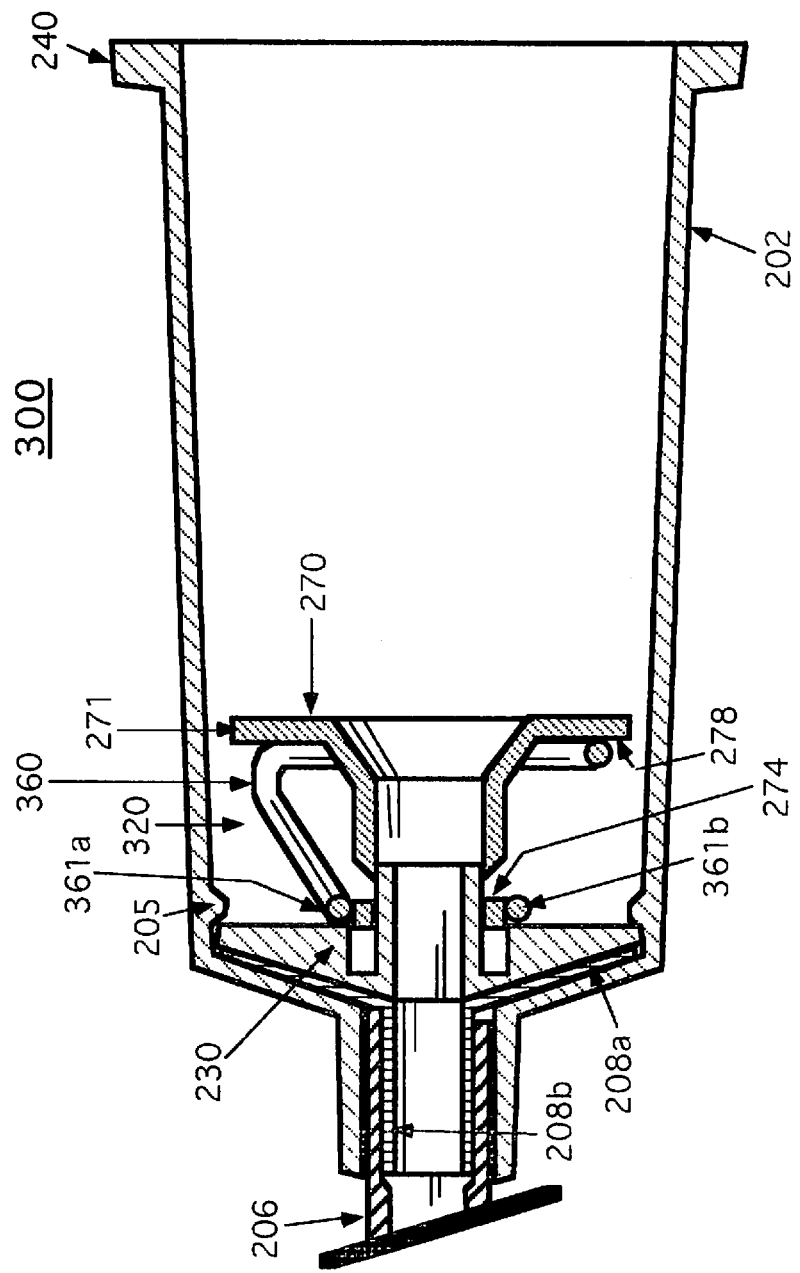
FIG. 24A shows a cross-sectional side view of an IV catheter having a luer-activated valve having an axial through-hole with a spring member in a first, retained position within an IV catheter hub before a needle is coaxially introduced into the IV catheter.
Figure 24B:
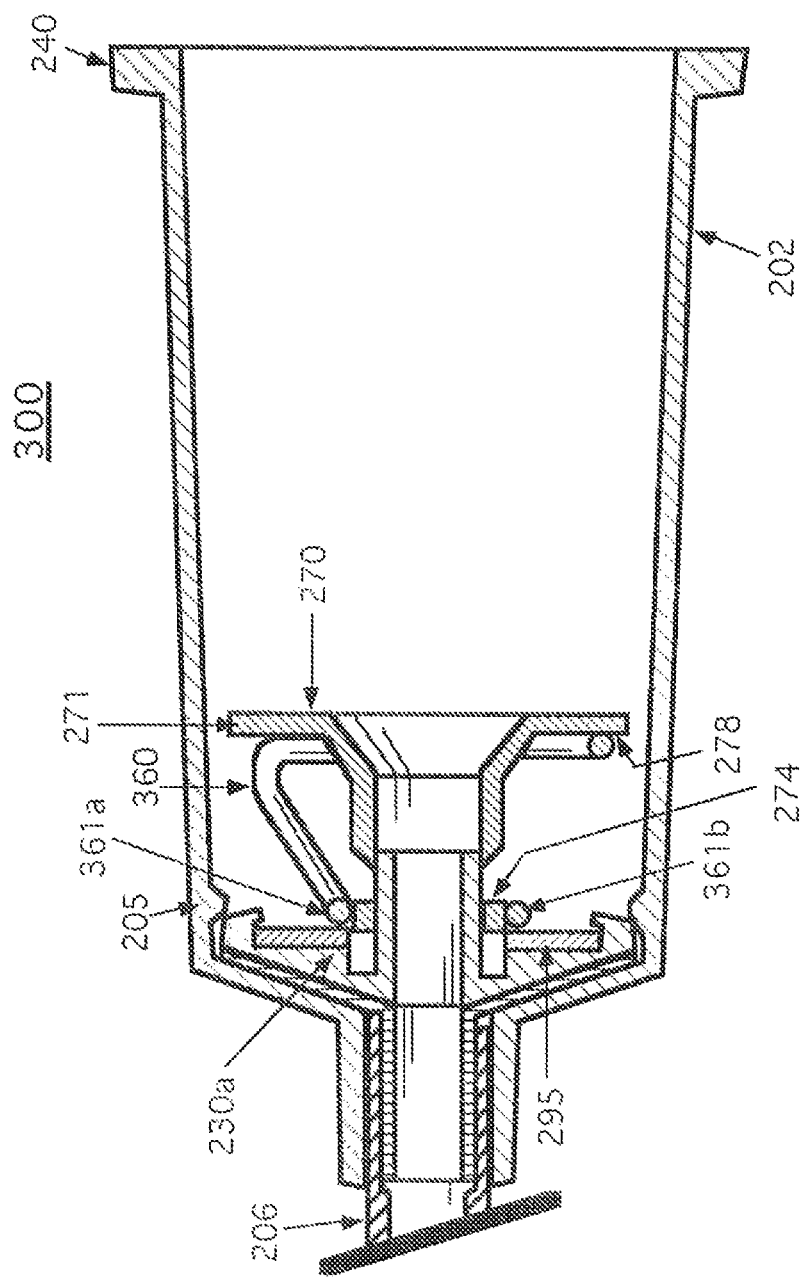
FIG. 24B shows a cross-sectional side view of the luer-activated valve of FIG. 24A having an annular rigid plate disposed between the distal end of the spring member and the proximal facing wall of the valve plug.

FIG. 24A shows a partial cross-sectional side view of IV catheter 300 with the valve assembly 320 positioned inside the catheter hub 202. The catheter tube 206 is coupled to the distal end of the catheter hub 202 by being fitted over an elongate portion 208b of the ferrule 208. According to one implementation the ferrule includes a first segment 208a that fits flush against an inner wall of the base 207 of the catheter hub 202. According to one implementation, like that shown in FIG. 24, the distal facing wall 233 of the valve plug 230 in turn fits flush against the proximal side of the ferrule 208.

According to some implementations the valve plug 230 is held in place inside the catheter hub 202 only as a result of being press-fit in the distal end of the catheter hub 202. According to other implementations the valve plug 230 is secured inside the catheter hub 202 by use of an adhesive. According to some implementations, as shown in FIG. 24A, one or more lips 205 protrude inward from the inner wall of the catheter hub 202 and function to hold or assist in holding the valve plug 230 in place.

As described previously in conjunction with the implementation of FIG. 1, prior to use, the IV catheter includes an introducer needle. The introducer needle is attached to a needle hub that is fixed to the catheter hub via a luer connection. In the "ready to use" state the introducer needle extends through the catheter hub and into the catheter tube with the sharpened distal tip of the needle protruding distally from the catheter tube as shown in FIG. 1. The use of an introducer needle applies to each of the IV catheter implementations disclosed herein.

FIG. 24A shows the IV catheter 300 prior to the introducer needle being introduced therein. In FIG. 24A the valve assembly is shown in a first operational state that allows the introducer needle to freely pass through the valve 320 and into the inner lumen of the catheter tube 206 during an assembly of the introducer needle into the IV catheter. In this first operational state, as with all operational states of the valve assembly, the spring clip 360 is held between the distal face 278 of the valve actuator flange 271 and the proximal facing wall 232 of the valve plug 230.

In regard to each of the operational states of the IV catheter 300 shown in FIGS. 24A-27, the first and second clamping segments 361a and 361b of spring clip 360 are positioned on the proximal facing wall 232 of the valve plug 230. According to other implementations a rigid annular plate or film 295 is disposed between the distal surface 245 of the clamp member 240 and the proximal facing wall 232 of the valve plug 230a as shown, for example, in FIG. 24B. According to some implementations the film may comprise a lubricious film applied to the proximal facing wall 232 of the valve plug 320.

According to some implementations the main body of the plug 230 is made of a first material having a first durometer and the annular plate 295 is made of a second material having a second durometer that is greater than the first durometer. According to some implementations the proximal facing surface of the annular plate 295 has a first surface roughness and the proximally facing wall 232 of the main body of the plug 230 has a second surface roughness that is greater than the first surface roughness.

The spring clip 360 is constructed and arranged in the valve assembly 320 such that the clamping segments 361a and 361b are continuously urged toward one another. Disposed between the first and second clamping segments 361a and 361b is the tubular projection 235 of the valve plug 230. Hence, when the clamping surfaces 361a and 361b are not being held apart by the first and second external tapered walls 277a and 277b of actuator 270, they are free to move radially inward toward one another to respectively press against the outer walls 237a and 237b of the tubular projection 235 of the valve plug 230.

Figure 25:
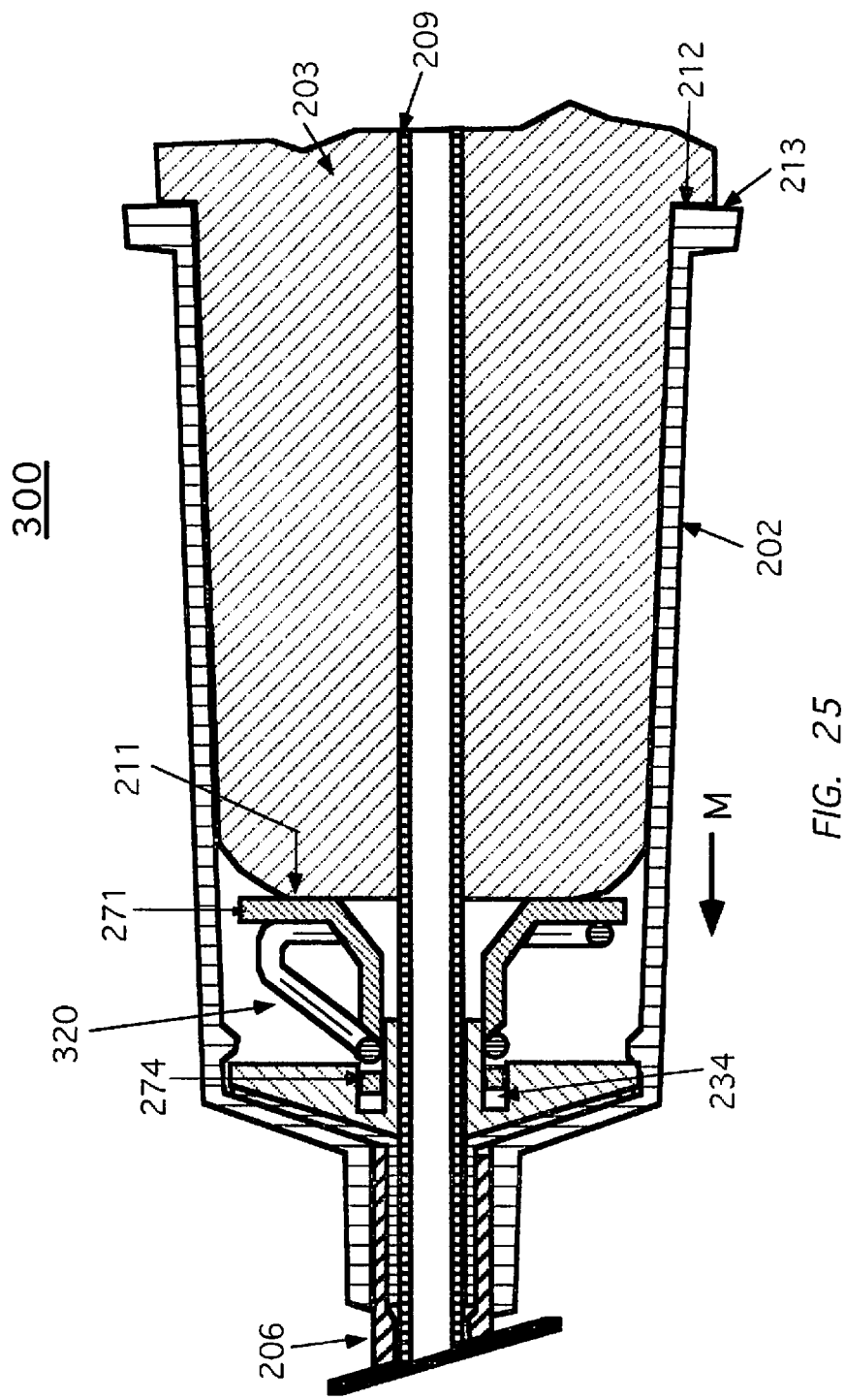
FIG. 25 shows a cross-sectional side view of a needle coaxially located in the luer-activated valve of FIG. 24A in a second, retained position with the distal end segments of the spring member placing clamping forces on a resilient elongate tube through which a needle passes.

In the first operational state of FIG. 24A, the actuator 270 is in a first axial position with the distal segment 274 of the actuator 270 being disposed between the clamping segments 361a and 361b and the tubular projection 235 of the valve plug 230, preventing the clamping segments 361a and 361b of spring clip 360 from pressing against the tubular projection 235. As a result, a through passage is provided through the valve assembly 220 to enable an introduction of the introducer needle into the IV catheter 300 allowing the needle to be threaded through the valve passageway during the assembly process without the need for a mandrel to open the passageway. As discussed above, the open passageway allows the needle bevel to move through the passageway without being damaged. FIG. 25 shows the introducer needle 209 assembled in the IV catheter 300.

FIG. 25 shows the IV catheter 300 in a second operational state with the actuator 270 located in a second axial position distal to the first axial position. The second operational state corresponds to the "ready to use" state discussed above. When the actuator 270 is in the second axial position, the distal end segment 274 of the prolongation 273 resides inside the recess 234 of the valve plug 230 allowing the clamping segments 361a and 361b of the spring clip 360 to move radially inward to press against the outer walls 237a and 237b of the tubular projection 235. Because the introducer needle 209 resides inside the tubular projection 235, the tubular projection substantially maintains its tubular form when the actuator 270 is in the second axial position.

As shown in FIG. 25, the introducer needle 209 is affixed to a needle hub 203 that resides inside the cavity 204 of the catheter hub 202. When the introducer needle 209 is assembled in the IV catheter 300, the distal end surface 211 of the needle hub 203 is caused to press against the flange 271 of the actuator 270 to cause the actuator to move from the first axial position to the second axial position. During the assembly process the needle hub 203 is moved distally in the direction M. According to one implementation the needle hub 203 is equipped with a stop 212 that engages with a part of the catheter hub 202 to limit the distal advancement of the needle hub into catheter hub to ensure or prevent the actuator 270 from being moved distally beyond the second axial position. In the example of FIG. 25 the stop comprises one or more protrusions 212 that extend radially from the needle hub 203. The one or more protrusions 212 are configured to act against a proximal end surface 213 of the catheter hub 202. According to one implementation the stop 212 constitutes a threaded part of the needle hub 203 that is configured to cooperate with the proximal luer flange 210 of the catheter hub 202 to achieve a fixation of the needle hub 203 with the catheter hub 202.

According to some implementations, as will be discussed in more detail below, the IV catheter 300 is equipped with a needle guard that is used to cover the distal sharpened tip of the introducer 209 upon its removal from the IV catheter. According to some implementations, the needle guard is disposed between the needle hub 203 and the actuator 270, and may in some instances transmit the force applied by the needle hub 203 to the actuator 270 during an assembly of the introducer needle 209 into the IV catheter.

With the IV catheter 200 in the "ready to use" state the clinician may introduce the catheter tube 206 into a vessel of a patient by puncturing the skin of the patient and also the wall of the vessel with the sharpened distal tip of the introducer needle 209 followed by an introduction of the distal end of the catheter tube 206 into the vessel. Upon the catheter tube 206 being successfully introduced into the vessel, the introducer needle is removed entirely from the IV catheter by disconnecting the needle hub from the catheter hub and advancing the needle 209 proximally.

Figure 26:
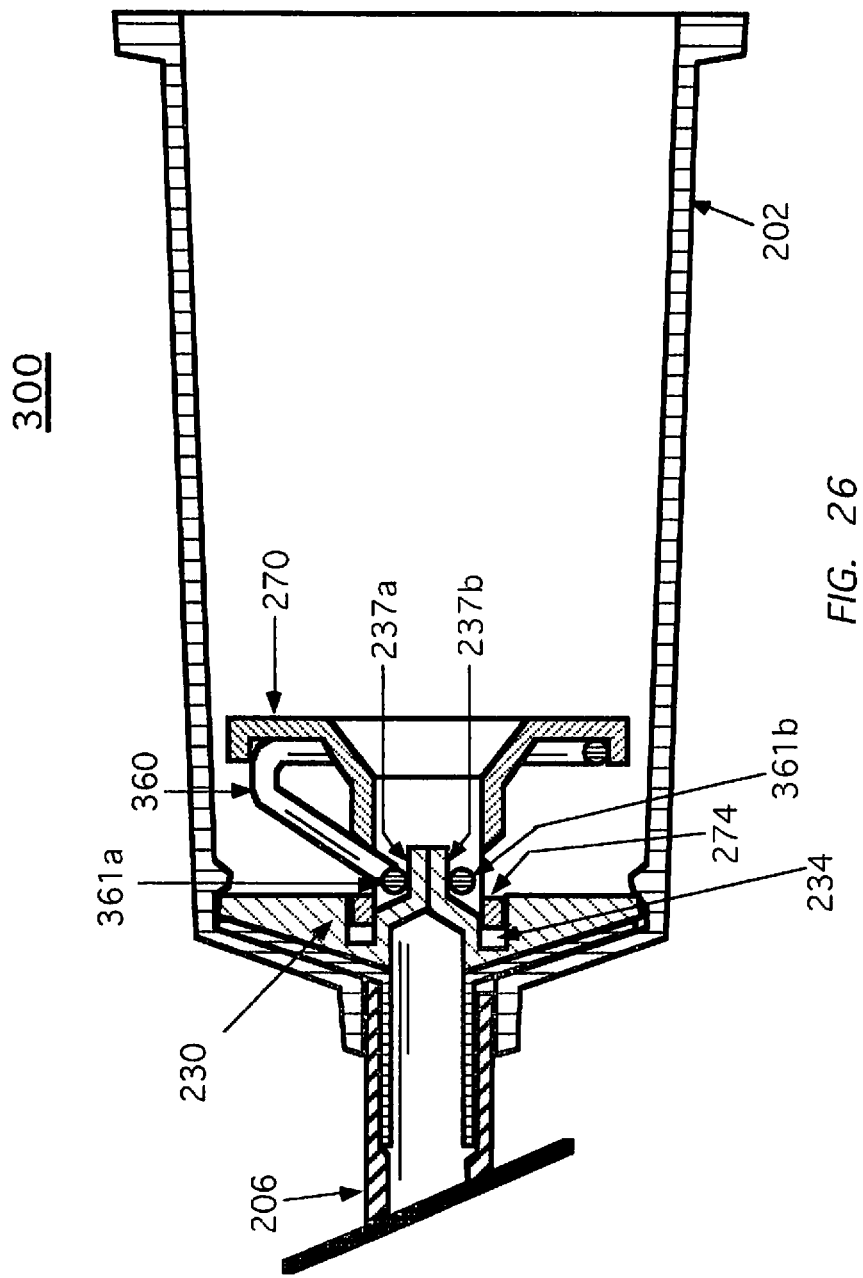
FIG. 26 shows a side view of the luer-activated valve shown in FIG. 24A in a third position (i.e. closed position) having a closed fluid path.

When the introducer needle 209 is removed from inside the tubular projection 235 of the valve plug 230, the forces exerted by the clamping 361a and 361b of spring clip 360 are capable of causing the outer walls of the tubular projection 235 to collapse causing the coming together of the opposing inner walls 238a and 238b to effectuate a closing of the valve as shown in FIGS. 26 and 29a-c. The configuration of FIG. 26 represents a third operational state of the IV catheter 300.

As discussed above, according to some implementations the actuator 270 includes a keyhole-shaped opening 275. The keyhole-shaped opening includes a central opening and first and second lobes 275a and 275b that protrude from opposite sides of the central opening. According to some implementations, when the tubular projection 235 of the valve plug 230 widens when being clamped, portions of the tubular projection extend outward from the central opening and into the first and second lobes 275a and 275b. According to some implementations the central opening has a circular shape and the lobes are defined by curved walls.

Figure 27:
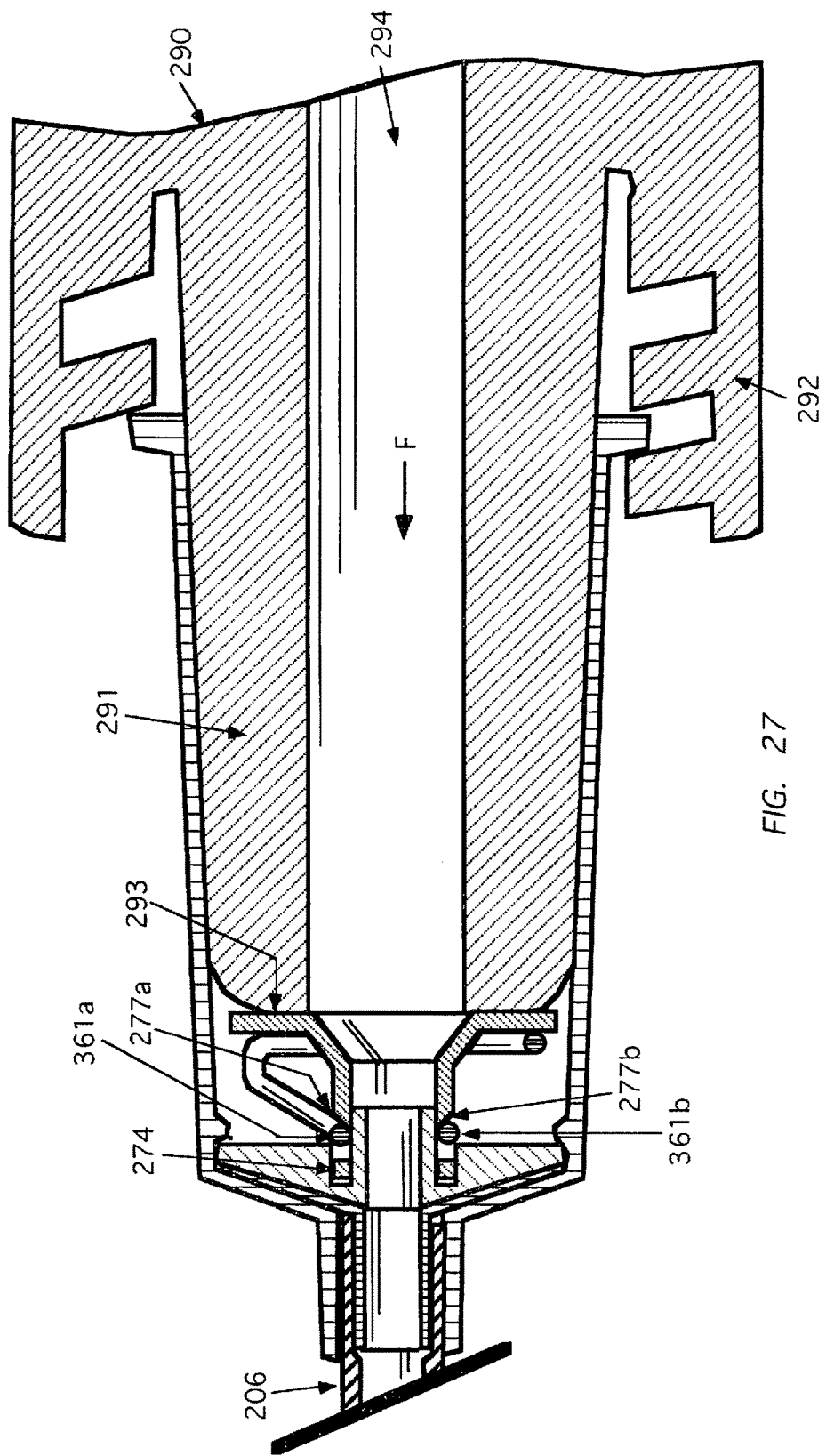
FIG. 27 shows a side view of the luer-activated valve of FIG. 24 in a fourth position having an unobstructed fluid path when a luer tipped connector is placed within the IV catheter hub.

When the IV catheter 300 is in the third operational state it is poised to receive a luer connector 290 as shown in FIG. 27 to facilitate an infusion of a therapeutic fluid into the vessel of the patient. In FIG. 27 the IV catheter 300 is shown in a fourth operational state. The luer connector 290 typically includes an elongate body 291 that extends into the cavity 204 of the catheter hub 202 as shown in FIG. 27. The luer connector 290 includes a threaded part 292 that is configured to cooperate with the proximal luer flange 210 of the catheter hub 202 to lock the luer connector in a fixed position inside the catheter hub 202 when the IV catheter is in the fourth operational state. As the luer connector 290 is advanced distally into the cavity of the catheter hub 202, at some point its distal end wall 293 makes contact with the proximal flange 271 of the actuator 270 and applies a force F to the actuator to cause the actuator to move in a distal direction to assume a third axial position as shown in FIG. 27. As the actuator 270 is moved distally toward the third axial position, the first and second external tapered walls 277a and 277b of the actuator respectively engage the clamping segments 361a and 361b of the spring clip 360 to cause the clamping segments 361a and 361b to disengage with the outer walls of the tubular projection 235 of the valve plug 230 to effectuate an opening of the valve 320. Thereafter, the through passage 236 of the valve plug 230 communicates a through passage 292 of the luer connector 290 with the inner lumen of the catheter tube 206 to enable a therapeutic agent to be administered into the vessel of the patient.

Figure 28:
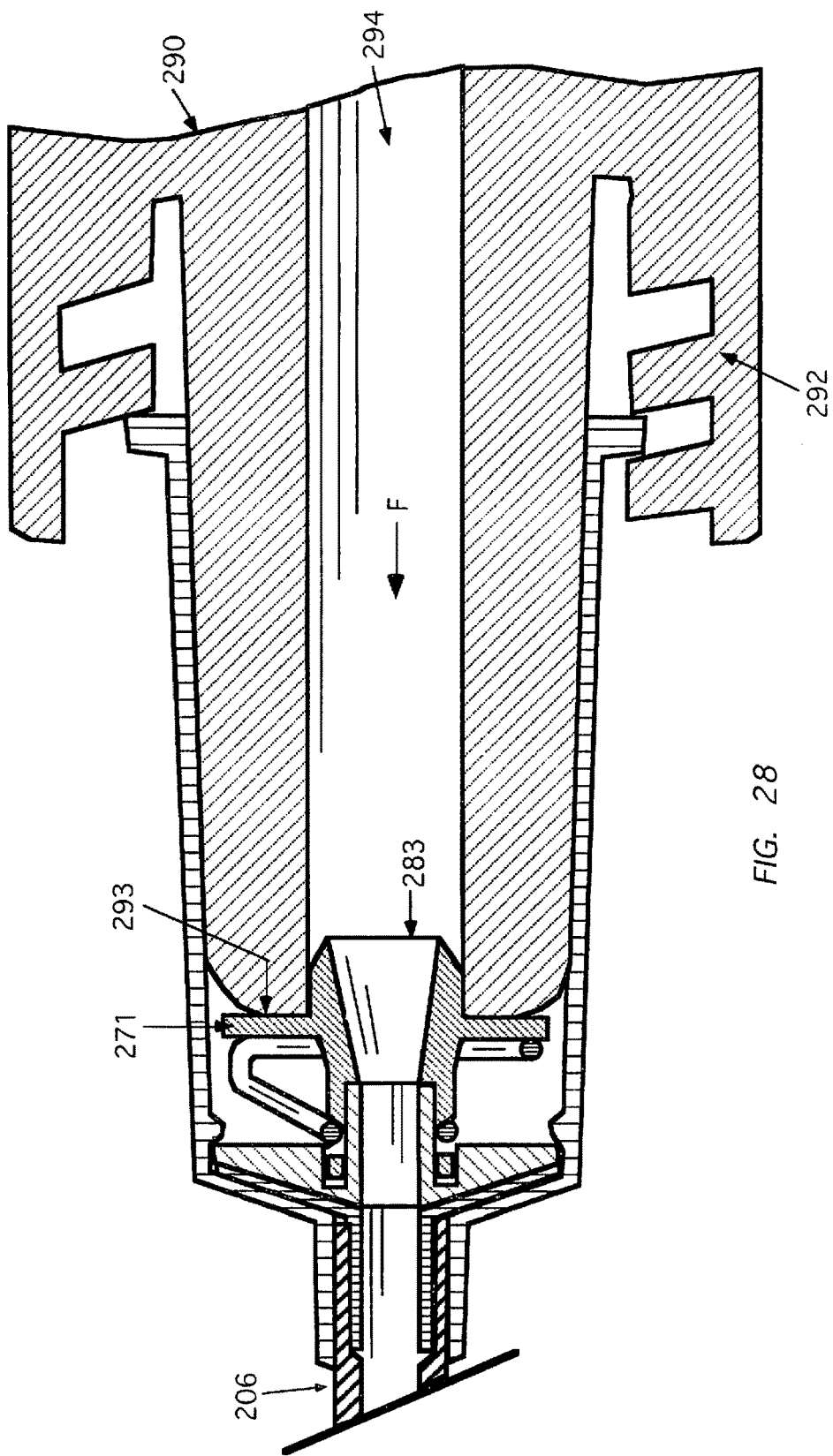
FIG. 28 is a cross-sectional side view of the IV catheter of FIG. 24A having incorporated therein the valve actuator of FIGS. 22A and 22B.

According to some implementations the actuator 270 includes a proximally extending tubular part 283 that extends proximally from the flange 271. The proximally extending tubular part 283 is sized to fit inside the inner lumen 294 of the luer connector 290 as shown in FIG. 28 to assist in placing the through passage of the actuator 270 and the lumen 294 of the luer connector in coaxial or near coaxial alignment to provide an unobstructed fluid pathway. According to some implementations, to avoid or minimize fluids administered through the luer connector 290 to pass distal to the actuator flange 271, the outer diameter d8 of the proximally extending tubular part 283 and the inner diameter of the luer connector lumen 294 are sized to produce a close sliding fit between them.

FIGS. 30A and 30B illustrate an IV catheter 400 similar to IV catheter 300 according to another implementation in which the sharpened distal end 34 of the introducer needle 209 is capable of being retracted proximally into a first internal chamber 411 of the needle hub 410 as the needle 209 is removed from the catheter tube 206. FIG. 30A shows the valve assembly 320 is its second operative state and FIG. 30B shows the valve assembly 320 in the third operational state.

In use, a trigger or other actuating device associated with the needle hub 410 is operative to evoke a proximal withdrawal of the sharpened distal end of the introducer needle 209 into the first internal chamber 411 through the use of a coil spring 420 that may be located in a second internal chamber 412 of the needle hub 410. As shown in FIGS. 30A and 30B, as the valve assembly 320 transitions from the second operational state to the third operational state the coil spring 420 axially expands inside the second chamber 412 to cause a proximal movement of the distal sharpened end 34 of the introducer needle 209 into safe storage inside the first internal chamber 411, thus adverting a possibility of a user of the IV catheter 400 being stuck by the needle tip 34.

According to one implementation the shaft of the needle just proximal to the sharpened distal tip 34 is provided with a change in profile (not shown in the figures). The change in profile region of the shaft has a width dimension (the width dimensional being orthogonal to the longitudinal axis of the introducer needle 209) that is greater than the diameter dimension of the remainder of the introducer needle. To limit the withdrawal of the sharpened distal tip 34 proximally beyond the first internal chamber 411, an internal wall portion located between or at the juncture of the first and second internal chambers 411 and 412 has a cross-sectional profile that is small enough to prevent a passage of the change in profile portion of the needle across the internal wall portion.

FIGS. 31A and 31B illustrate an IV catheter 500 according to another implementation having a needle guard 520 integrated therewith. FIG. 31A shows the valve assembly 320 is its second operational state and FIG. 31B shows the valve assembly 320 in the third operational state.

The needle guard 520 includes a base 521 from which resilient arms 522a and 522b distally extend. Each of arms 522a and 522b respectively includes a distal end segment 523a and 523b that extends radially inward toward the shaft of the introducer needle 209. When the IV catheter is in the ready-to-use state as shown in FIG. 31A, a portion 524a and 524b of each of segments 523a and 523b reside forced against the shaft of the introducer needle 209. According to one implementation the needle guard 520 further includes an elongate member 525 that extends axially between the base 521 and the distal end segments 523a and 523b of the resilient arms 522a and 522b.

The IV catheter assembly 500 also includes a needle hub 530 to which a distal end or distal end portion 531 of the introducer needle 209 is attached. When the IV catheter is in the ready-to-use state a distal end portion of the needle hub 530 is attached to a proximal end portion of the catheter hub 202 with a proximal end portion of the introducer needle 209 passing through a proximal opening in the elongate member 525 and an opening in the base 521 of the needle guard. In the ready-to-use state the introducer needle 209 passes through the needle guard 520, the valve assembly 320 and into the catheter tube 206 such that the sharpened distal end 34 resides distal to the distal end of the catheter tube 206. When the IV catheter is in the ready-to-use state, the inner wall of the catheter hub 202 may possess one or more inward protruding lips 528 that are configured to engage with portions 529a and 529b of the needle guard arms 521a and 521b to assist in fixing the axial position of the needle guard 520 inside the catheter hub 202.

Prior to having assumed the second operational state, the valve actuator 270 is forced in a distal direction to cause the distal end segment 274 of the actuator to move distally into the recess 234 of the valve plug 230. According to one implementation, the distally applied force originates from a distal movement of the needle hub 530 as it is being attached to the catheter hub 202. As the needle hub 530 moves distally, the distal face 535 of the needle hub engages with the proximal face 526 of the needle guard base 521 to cause at least one of the first and second distal end segments 523a and 523b of arms 522a and 522b to press against the actuator flange 271 to cause a movement of the distal end segment 274 of the actuator 271 to move distally into the recess 234 of the valve plug 230 to cause the valve assembly to transition from the first operational state to the second operational state.

Upon the distal end portion of the catheter tube 206 being successfully introduced into a vein of the patient, the clinician may then remove the introducer needle from the catheter tube 206 as shown in FIG. 31B. Removal is accomplished by detaching the needle hub 530 from the catheter hub 202 and pulling the needle hub proximally until the sharpened distal end 34 of the needle 209 resides inside a cavity of the elongate member 525 of the needle guard 520. Upon the sharpened distal tip 34 of the needle 209 entering the elongate member 525, the resilient arms 522a and 522b are free to move radially inward toward one another to assume the position as shown in FIG. 31B, locking the tip of the needle 209 inside the elongate member.

According to one implementation the shaft of the needle just proximal to the sharpened distal tip 34 is provided with a change in profile (not shown in the figures). The change in profile region of the introducer needle shaft has a width dimension (the width dimensional being orthogonal to the longitudinal axis of the introducer needle 209) that is greater than the diameter dimension of a proximal end portion 525a of the elongate member 525 in order to limit the withdrawal of the sharpened distal tip 34 proximally beyond the elongate member 525 as shown in FIG. 31B.

When the entirety of the sharpened distal tip 34 of the introducer needle 209 being located inside the elongate member 525, the distal end portions 523a and 523b move radially inward to reside over the distal opening 525b of the elongate member 525 to lock the sharpened distal tip inside the elongate member. Thereafter, the entirety of the needle guard 520 is removed from the inner cavity of the catheter hub 202 by a continued proximal withdrawal of the needle hub 530.

Needle guard 520 may be similar to or the same as the needle guard implementations disclosed in co-owned U.S. Pat. No. 8,764,711 (filed Feb. 28, 2011 and issued Jul. 1, 2014), which is incorporated by reference herein in its entirety.

Figure 32F:
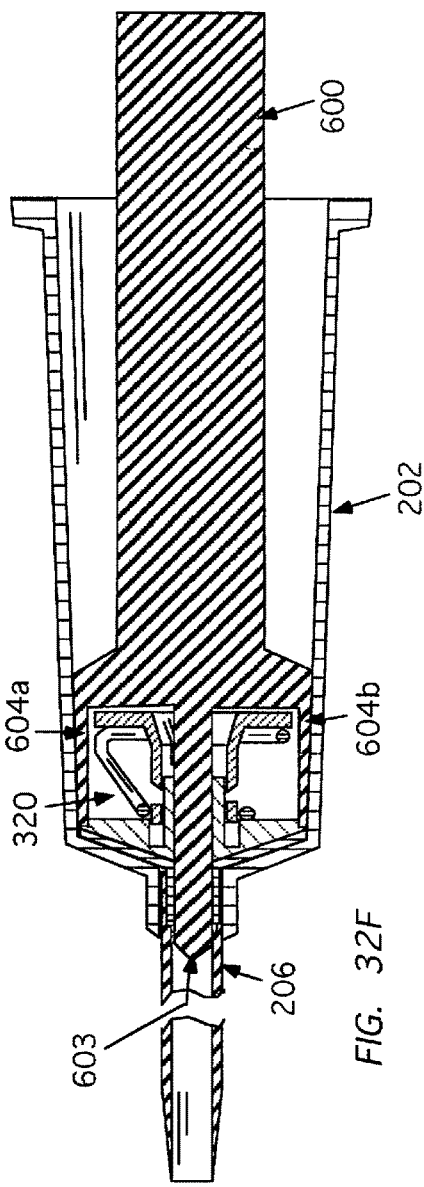
Figure 32G:
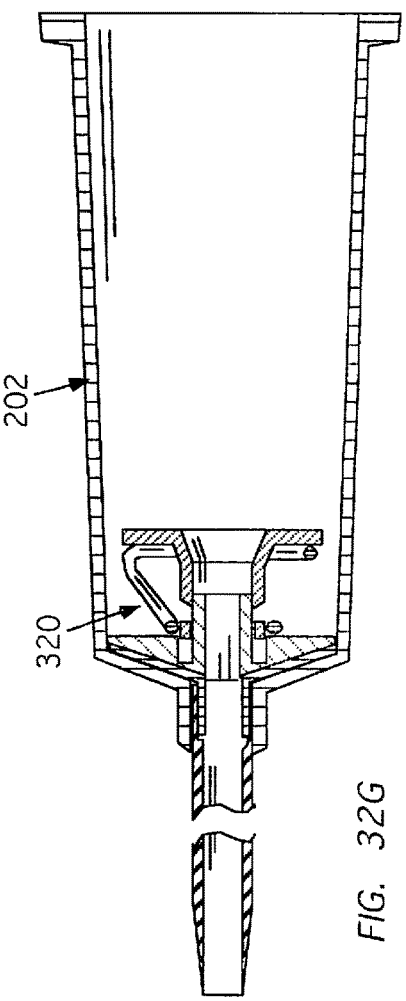
Figure 32E:
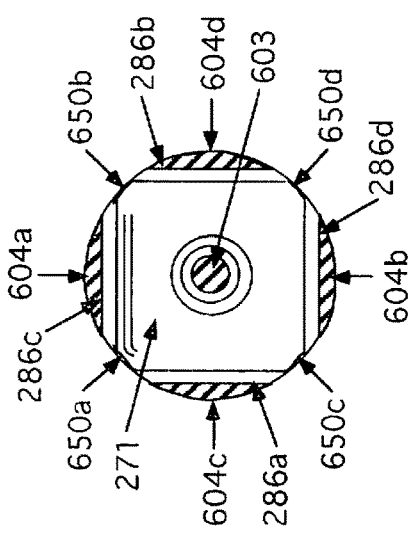

FIGS. 32A-G show a method of loading the valve assembly 320 in its first operational state into catheter hub 202. The method includes the use of a mandrel 600 that includes an elongate proximal handle 601 that can be gripped by an assembler or automated assembly means, during the loading process. Extending distally to the handle 601 are a central pin 603 and two or more side arms 604a and 604b that at least partially surround the central pin 603. In the implementation of FIG. 32D the mandrel includes two side arms 604a and 604b. In the implementation of FIG. 32E the mandrel includes four side arms 604a-d. The mandrel 600 is made of rigid material that prevents any part of the mandrel from flexing during an assembling of the valve assembly 320 into the catheter hub.

The assembly process includes assembling together the actuator 270, spring element 360 and plug 230 to form the valve assembly 320 in its first operational state as shown in FIG. 32B. As explained above, when the valve 320 is in the first operational state the clamping segments 361a and 361b of the spring element 360 reside forced against the distal end segment 274 of the actuator 270 to prevent the clamping segments 361a and 361b from acting on the tubular projection 235 of the valve plug 230.

The valve 320 may be pre-assembled before being placed on the mandrel 600 or valve 320 may be sequentially assembled on the mandrel 600 itself. When the valve 320 is pre-assembled before being placed on the mandrel 600, it is done so in its first operational state, being loaded onto the mandrel 600 such that the central pin 603 of the mandrel extends through the through passage 640 of the valve assembly 320 as shown in FIG. 32C. When the valve assembly 320 is fully loaded onto the mandrel, the distal ends 605a and 605b of the side arms 604a and 604b are positioned touching the proximal facing wall 232 of the valve plug 230 and the distal end 603a of the central pin 603 protrudes distally from the valve plug 230. According to one implementation the length L1 of each of side arms 604a and 604b is sufficiently long to ensure a gap 609 exists between the actuator 270 and a distal facing wall 608 of the mandrel from which the side arms protrude. The existence of the gap 609 guards against the actuator 270 being acted on by the mandrel 600 as the valve assembly 320 is loaded into the catheter hub 202, ensuring that the valve assembly 320 remains in its first operational state during the loading process.

As shown in FIG. 32A, the length L2 of the central pin 603 is greater than the length L1 of each of the side arms 604a and 604b.

In the implementation of FIG. 32D the flange 271 of the actuator 272 is shown having first and second curved sides 285a and 285b and first and second straight sides 286a and 286b like that shown in FIGS. 14C and 19C or in actuator 270. The existence of the first and second straight sides provides a passageway between the outer periphery of the actuator flange 271 and the inner wall of the catheter hub 202 through which the side arms 604a and 604b of the mandrel 600 pass when the valve assembly 320 is introduced into the catheter hub as shown in FIG. 32F.

In the implementation of FIG. 32E the mandrel 600 is equipped with four projecting side walls 604a-d and the actuator flange 271 includes four straight sides 286a-d separated by four curved corners 650a-d. According to other implementations the mandrel 600 is equipped with three projecting side walls and the actuator flange 271 includes three straight sides separated by three curved corners. The use of a mandrel having three or more projecting side walls spaced equidistantly about an outer perimeter of the mandrel ensures against a valve assembly 320 being skewed in one direction or another during its loading into the catheter hub.

While the valve assembly 320 is being introduced into the catheter hub 202, the distal ends 604a and 604b of side arms 603a and 603b press against the proximal facing wall 232 of the base 231 of plug 230 to force the distal facing wall 233 of the plug 230. According to some implementations the base 231 of the plug 230 is made of a material that prevents it from deforming during the insertion of the valve assembly 320 into the catheter hub 202. Alternatively, the base 231 of the plug 230 may be supported on a rigid structure attached to its distal facing wall 233.

As shown in FIG. 32F, the length L2 of the central pin 603 of mandrel 600 is sufficiently long such that it extends distally into the inner lumen of the catheter tube 206 when the valve assembly is distally positioned inside the catheter hub 202. This feature assures a proper axial alignment of the valve assembly 320 inside the catheter hub 202 to ensure the valve passageway 640 is properly aligned with the inner lumen of the catheter tube 206.

Upon the valve assembly 320 being fixed inside the catheter hub 202 as shown in FIG. 32F, the mandrel 600 is proximally withdrawn from the catheter hub such that the IV catheter configuration of FIG. 32G exists, the valve assembly 320 being in its first operational state. The introducer needle 209 may thereafter be introduced into the IV catheter assembly as described in detail above.

The following clauses disclose in an unlimited way additional implementations. Group A through F clauses are provided.

Group A Clauses:

Clause 1. A valve assembly configured for placement inside a hub that has a proximal opening, a distal opening and an internal cavity disposed between the proximal and distal openings, the cavity defined by one or more sidewalls and a distal wall of the hub, the distal opening extending through the distal wall, the valve assembly comprising:

a plug made of a resilient material, the plug including a main body having a proximal facing surface and a distal facing surface, the main body including an axial through opening and being configured such that the axial through opening is in fluid communication with the distal opening of the hub, the axial through opening extending through a tubular part that has a proximal end portion that protrudes proximal to the proximal facing surface of the main body, there existing a recess in the proximal facing surface that at least partially surrounds the tubular part;

an actuator including a proximal flange having a proximal facing surface, the actuator including a distally protruding structure that extends distal to the proximal flange, there being an axial through opening that extends through the proximal flange and the distally protruding structure, the distally protruding structure having a proximal part, a distal part and a transverse through opening disposed between the proximal and distal parts, the distal part having an outer wall, the proximal end portion of the tubular part of the plug residing inside the distally protruding structure; and a spring member including a proximal end segment and first and second clamping segments that are operatively coupled to the proximal end segment respectively by first and second arms, the spring member being configured to cause the first and second clamping segments to move radially apart from one another when a distally applied force is applied to the proximal end segment, when the actuator is in a first axial position the first and second clamping segments are urged against the outer wall of the distal part of the actuator, when the actuator is in a second axial position distal to the first axial position the distal part of the actuator is configured to move distally into the recess in the proximal facing surface of the main body of the plug and the first and second clamping segments of the spring member move radially inward into the transverse through opening of the actuator to act against the proximal end portion of the tubular part of the plug in a manner sufficient to cause a closing of the axial through opening of the plug in the proximal end portion.

Clause 2. The valve assembly according to clause 1, wherein the proximal part of the actuator has an outer wall that tapers distally inward, when the actuator is in the second axial position the actuator is movable distally to a third axial position distal to the second axial position to cause the tapered outer wall of the first part of the actuator to act on the first and second clamping segments in a manner that results in the first and second clamping segments to move radially outward in a manner sufficient to at least partially open the axial through opening of the plug.

Clause 3. The valve assembly according to clause 1, wherein when the actuator transitions from the first axial position to the second axial position the actuator is incapable of reassuming the first axial position.

Clause 4. The valve assembly according to clause 2, wherein when the actuator transitions from the first axial position to the second axial position the actuator is incapable of reassuming the first axial position.

Clause 5. The valve assembly according to clause 1, wherein the proximal end segment of the spring member abuts a distal facing surface of the proximal flange of the actuator and each of the first and second clamping segments abuts the proximal facing surface of the main body of the plug.

Clause 6. The valve assembly according to clause 1, wherein the proximal flange of the actuator has a first diameter dimension and the distally protruding part of the actuator has a second diameter dimension that is less than the first diameter dimension.

Clause 7. The valve assembly according to clause 1, wherein the axial through opening of the actuator comprises a key-hole shape.

Clause 8. The valve assembly according to clause 1, wherein the distal facing surface of the main body of the plug is configured to abut the distal wall of the hub.

Clause 9. The valve assembly according to clause 1, wherein a press fit exists between the main body of the plug and the one or more sidewalls of the hub.

Clause 10. The valve assembly according to clause 1, further comprising an annular plate disposed between the first and second clamping segments of the spring member and the proximal facing surface of the main body of the plug.

Clause 11. The valve assembly according to clause 10, wherein the first and second clamping segments of the spring member abuts a proximal facing surface of the annular plate.

Clause 12. The valve assembly according to clause 11, wherein the main body of the plug is made of a first material having a first durometer and the annular plate is made of a second material having a second durometer that is greater than the first durometer.

Clause 13. The valve assembly according to clause 11, wherein the proximal facing surface of the annular plate has a first surface roughness and the proximally facing surface of the main body of the plug has a second surface roughness that is greater than the first surface roughness.

Clause 14. The valve assembly according to clause 12, wherein the proximal facing surface of the annular plate has a first surface roughness and the proximally facing surface of the main body of the plug has a second surface roughness that is greater than the first surface roughness.

Clause 15. The valve assembly according to clause 1, wherein the outer wall of the distal part of the actuator includes an indentation in which the first and second clamping segments of the spring member reside when the actuator is in the first axial position, the indentation configured to assist in holding the first and second clamping segments on the distal part of the actuator.

Group B Clauses:

Clause 1. An intravenous catheter comprising:

a catheter hub that has a proximal opening, a distal opening and an internal cavity disposed between the proximal and distal openings, the cavity defined by one or more sidewalls and a distal wall of the catheter hub, the distal opening extending through the distal wall;

a plug made of a resilient material, the plug including a main body having a proximal facing surface and a distal facing surface, the main body including an axial through opening and being configured such that the axial through opening is in fluid communication with the distal opening of the hub, the axial through opening extending through a tubular part that has a proximal end portion that protrudes proximal to the proximal facing surface of the main body, there existing a recess in the proximal facing surface that at least partially surrounds the tubular part;

an actuator including a proximal flange having a proximal facing surface, the actuator including a distally protruding structure that extends distal to the proximal flange, there being an axial through opening that extends through the proximal flange and the distally protruding structure, the distally protruding structure having a proximal part, a distal part and a transverse through opening disposed between the proximal and distal parts, the distal part having an outer wall, the proximal end portion of the tubular part of the plug residing inside the distally protruding structure; and a spring member including a proximal end segment and first and second clamping segments that are operatively coupled to the proximal end segment respectively by first and second arms, the spring member being configured to cause the first and second clamping segments to move radially apart from one another when a distally applied force is applied to the proximal end segment, when the actuator is in a first axial position the first and second clamping segments are urged against the outer wall of the distal part of the actuator, when the actuator is in a second axial position distal to the first axial position the distal part of the actuator is configured to move distally into the recess in the proximal facing surface of the main body of the plug and the first and second clamping segments of the spring member move radially inward into the transverse through opening of the actuator to act against the proximal end portion of the tubular part of the plug in a manner sufficient to cause a closing of the axial through opening of the plug in the proximal end portion.

Clause 2. The catheter assembly according to clause 1, wherein the proximal part of the actuator has an outer wall that tapers distally inward, when the actuator is in the second axial position the actuator is movable distally to a third axial position to cause the tapered outer wall of the first part of the actuator to act on the first and second clamping segments in a manner that results in the first and second clamping segments to move radially outward in a manner sufficient to at least partially open the axial through opening of the plug.

Clause 3. The catheter assembly according to clause 1, wherein when the actuator transitions from the first axial position to the second axial position the actuator is incapable of reassuming the first axial position.

Clause 4. The catheter assembly according to clause 2, wherein when the actuator transitions from the first axial position to the second axial position the actuator is incapable of reassuming the first axial position.

Clause 5. The catheter assembly according to clause 1, wherein the proximal end segment of the spring member abuts a distal facing surface of the proximal flange of the actuator and each of the first and second clamping segments abuts the proximal facing surface of the main body of the plug.

Clause 6. The catheter assembly according to clause 1, wherein the proximal flange of the actuator has a first diameter dimension and the distally protruding part of the actuator has a second diameter dimension that is less than the first diameter dimension.

Clause 7. The catheter assembly according to clause 1, wherein the axial through opening of the actuator comprises a key-hole shape.

Clause 8. The catheter assembly according to clause 1, wherein the distal facing surface of the main body of the plug is configured to abut the distal wall of the catheter hub.

Clause 9. The catheter assembly according to clause 1, wherein a press fit exists between the main body of the plug and the one or more sidewalls of the catheter hub.

Clause 10. The catheter assembly according to clause 1, further comprising an annular plate disposed between the first and second clamping segments of the spring member and the proximal facing surface of the main body of the plug.

Clause 11. The catheter assembly according to clause 10, wherein the first and second clamping segments of the spring member abut a proximal facing surface of the annular plate.

Clause 12. The catheter assembly according to clause 11, wherein the main body of the plug is made of a first material having a first durometer and the annular plate is made of a second material having a second durometer that is greater than the first durometer.

Clause 13. The catheter assembly according to clause 11, wherein the proximal facing surface of the annular plate has a first surface roughness and the proximally facing surface of the main body of the plug has a second surface roughness that is greater than the first surface roughness.

Clause 14. The catheter assembly according to clause 12, wherein the proximal facing surface of the annular plate has a first surface roughness and the proximally facing surface of the main body of the plug has a second surface roughness that is greater than the first surface roughness.

Clause 15. The catheter assembly according to clause 1, wherein the outer wall of the distal part of the actuator includes an indentation in which the first and second clamping segments of the spring member reside when the actuator is in the first axial position, the indentation configured to assist in holding the first and second clamping segments on the distal part of the actuator.

Clause 16. The catheter assembly according to clause 1, further comprising a ferrule positioned between the distal wall of the catheter hub and the distal facing surface of the main body of the plug.

Clause 17. The catheter assembly according to clause 16, further comprising an elongate tube having a proximal end and a distal end, the proximal end being secured to the ferrule.

Clause 18. The catheter assembly according to clause 1, further comprising an introducer needle having a proximal end portion, a sharpened distal tip and a shaft extending between the proximal end and the sharpened distal tip, the shaft extending through the axial through opening the plug and the axial through opening of the actuator when the actuator is in the second axial position.

Clause 19. The catheter assembly according to clause 18, further comprising an elongate catheter tube having a proximal end, a distal end and an inner lumen extending through and between the proximal and distal ends, the proximal end of the catheter tube being fixed to a distal end portion of the catheter hub, the shaft of the introducer needle extending through the inner lumen of the catheter tube.

Clause 20. The catheter assembly according to clause 18, wherein the proximal end portion of the introducer needle is coupled to a needle hub, the needle hub being detachably coupled to a proximal end of the catheter hub.

Clause 21. The catheter assembly according to clause 20, wherein the needle hub has a distally facing surface that presses against the proximal facing surface of the proximal flange of the actuator to cause the actuator to transition from the first axial position to the second axial position.

Clause 22. The catheter assembly according to clause 18, wherein the shaft of the introducer needle has a first diameter and the inner diameter of the axial through opening extending through the proximal end portion of tubular part of the plug having a second diameter dimension, the first diameter dimension being no more than 20% greater than the second diameter dimension.

Clause 23. The catheter assembly according to clause 1, wherein the proximal facing surface of the main body of the plug has applied thereto a lubricious film, the first and second clamping segments of the spring member being positioned on a surface of the lubricious film.

Clause 24. The catheter assembly according to clause 20, wherein the sharpened distal tip of the introducer needle is retractable into the needle hub.

Clause 25. The catheter assembly according to clause 20, further comprising a needle guard disposed between the distally facing surface of the needle hub and the proximal flange of the actuator.

Clause 26. The catheter assembly according to clause 25, wherein the needle guard has a distally facing surface that presses against the proximal facing surface of the proximal flange of the actuator to cause the actuator to transition from the first axial position to the second axial position.

Group C Clauses:

Clause 1. A valve assembly configured for placement inside a hub that has a proximal opening, a distal opening and an internal cavity disposed between the proximal and distal openings, the cavity defined by one or more sidewalls and a distal wall, the distal opening extending through the distal wall, the valve assembly comprising:

a plug made of a resilient material, the plug including a main body having a proximal facing surface and a distal facing surface, the main body including an axial through opening and being configured such that the axial through opening is in fluid communication with the distal opening of the hub, the axial through opening extending through a tubular part that has a proximal end portion that protrudes proximal to the proximal facing surface of the main body, there existing a recess in the proximal facing surface that at least partially surrounds the tubular part;

an actuator including a proximal flange having a proximal facing surface, the actuator including a distally protruding structure that extends distal to the proximal flange, there being an axial through opening that extends through the proximal flange and the distally protruding structure, the distally protruding structure having a proximal part, a distal part and a transverse through opening disposed between the proximal and distal parts, the distal part having an outer wall, the proximal end portion of the tubular part of the plug residing inside the distally protruding structure;

a clamping device having first and second clamping arms that are resiliently urged inward toward one another, the clamping device having an axial through opening through which the distally protruding structure of the actuator passes, when the actuator is in a first axial position the first and second clamping arms are urged against the outer wall of the distal part of the actuator, when the actuator is in a second axial position distal to the first axial position the distal part of the actuator is configured to move distally into the recess in the proximal facing surface of the main body of the plug and the first and second clamping arms move radially inward into the transverse through opening of the actuator to act against the proximal end portion of the tubular part of the plug in a manner sufficient to cause a closing of the axial through opening of the plug at the proximal end portion; and a spring that acts on the actuator to urge the actuator in a proximal direction when the actuator is in the second axial position.

Clause 2. The valve assembly according to clause 1, wherein the proximal part of the actuator has an outer wall that tapers distally inward, when the actuator is in the second axial position the actuator is movable distally to a third axial position to cause the tapered outer wall of the first part of the actuator to act on the first and second clamping arms in a manner that results in the first and second clamping arms to move radially outward in a manner sufficient to at least partially open the axial through opening of the plug.

Clause 3. The valve assembly according to clause 1, wherein when the actuator transitions from the first axial position to the second axial position the actuator is incapable of reassuming the first axial position.

Clause 4. The valve assembly according to clause 2, wherein when the actuator transitions from the first axial position to the second axial position the actuator is incapable of reassuming the first axial position.

Clause 5. The valve assembly according to clause 1, wherein the spring has a proximal end that abuts a distal facing surface of the proximal flange of the actuator and a distal end that abuts the proximal facing surface of the main body of the plug.

Clause 6. The valve assembly according to clause 1, wherein the first and second clamping arms are urged radially inward at least in part by a resilient O-ring that circumscribes the clamping device.

Clause 7. The valve assembly according to clause 1, wherein the proximal flange of the actuator has a first diameter dimension and the distally protruding part of the actuator has a second diameter dimension that is less than the first diameter dimension.

Clause 8. The valve assembly according to clause 1, wherein the axial through opening of the actuator comprises a key-hole shape.

Clause 9. The valve assembly according to clause 1, wherein the distal facing surface of the main body of the plug is configured to abut the distal wall of the hub.

Clause 10. The valve assembly according to clause 1, wherein a press fit exists between the main body of the plug and the one or more sidewalls of the hub.

Clause 11. The valve assembly according to clause 1, wherein the clamping device has a distal facing surface that abuts the proximal facing surface of the main body of the plug.

Clause 12. The valve assembly according to clause 1, further comprising an annular plate disposed between a distal facing surface of the clamping device and the proximal facing surface of the main body of the plug.

Clause 13. The valve assembly according to clause 12, wherein a distal facing surface of the clamping device abuts a proximal facing surface of the annular plate.

Clause 14. The valve assembly according to clause 13, wherein the main body of the plug is made of a first material having a first durometer and the annular plate is made of a second material having a second durometer that is greater than the first durometer.

Clause 15. The valve assembly according to clause 13, wherein the proximal facing surface of the annular plate has a first surface roughness and the proximally facing surface of the main body of the plug has a second surface roughness that is greater than the first surface roughness.

Clause 16. The valve assembly according to clause 14, wherein the proximal facing surface of the annular plate has a first surface roughness and the proximally facing surface of the main body of the plug has a second surface roughness that is greater than the first surface roughness.

Clause 17. The valve assembly according to clause 1, wherein the outer wall of the distal part of the actuator includes an indentation in which a distal end segment of the spring resides when the actuator is in the first axial position, the indentation configured to assist in holding the distal end segment on the distal part of the actuator.

Group D Clauses:

Clause 1. An intravenous catheter comprising:

a catheter hub that has a proximal opening, a distal opening and an internal cavity disposed between the proximal and distal openings, the cavity defined by one or more sidewalls and a distal wall of the catheter hub, the distal opening extending through the distal wall;

a plug made of a resilient material, the plug including a main body having a proximal facing surface and a distal facing surface, the main body including an axial through opening and being configured such that the axial through opening is in fluid communication with the distal opening of the hub, the axial through opening extending through a tubular part that has a proximal end portion that protrudes proximal to the proximal facing surface of the main body, there existing a recess in the proximal facing surface that at least partially surrounds the tubular part;

an actuator including a proximal flange having a proximal facing surface, the actuator including a distally protruding structure that extends distal to the proximal flange, there being an axial through opening that extends through the proximal flange and the distally protruding structure, the distally protruding structure having a proximal part, a distal part and a transverse through opening disposed between the proximal and distal parts, the distal part having an outer wall, the proximal end portion of the tubular part of the plug residing inside the distally protruding structure;

a clamping device having first and second clamping arms that are resiliently urged inward toward one another, the clamping device having an axial through opening through which the distally protruding structure of the actuator passes, when the actuator is in a first axial position the first and second clamping arms are urged against the outer wall of the distal part of the actuator, when the actuator is in a second axial position distal to the first axial position the distal part of the actuator is configured to move distally into the recess in the proximal facing surface of the main body of the plug and the first and second clamping arms move radially inward into the transverse through opening of the actuator to act against the proximal end portion of the tubular part of the plug in a manner sufficient to cause a closing of the axial through opening of the plug at the proximal end portion; and a spring that acts on the actuator to urge the actuator in a proximal direction when the actuator is in the second axial position.

Clause 2. The catheter assembly according to clause 1, wherein the proximal part of the actuator has an outer wall that tapers distally inward, when the actuator is in the second axial position the actuator is movable distally to a third axial position to cause the tapered outer wall of the first part of the actuator to act on the first and second clamping arms in a manner that results in the first and second clamping arms to move radially outward in a manner sufficient to at least partially open the axial through opening of the plug.

Clause 3. The catheter assembly according to clause 1, wherein when the actuator transitions from the first axial position to the second axial position the actuator is incapable of reassuming the first axial position.

Clause 4. The catheter assembly according to clause 2, wherein when the actuator transitions from the first axial position to the second axial position the actuator is incapable of reassuming the first axial position.

Clause 5. The catheter assembly according to clause 1, wherein the spring has a proximal end and a distal end, the proximal end of the spring abutting a distal facing surface of the proximal flange of eh actuator, the distal end of the spring abutting the proximal facing surface of the main body of the plug.

Clause 6. The catheter assembly according to clause 1, wherein the proximal flange of the actuator has a first diameter dimension and the distally protruding part of the actuator has a second diameter dimension that is less than the first diameter dimension.

Clause 7. The catheter assembly according to clause 1, wherein the axial through opening of the actuator comprises a key-hole shape.

Clause 8. The catheter assembly according to clause 1, wherein the distal facing surface of the main body of the plug is configured to abut the distal wall of the catheter hub.

Clause 9. The catheter assembly according to clause 1, wherein a press fit exists between the main body of the plug and the one or more sidewalls of the catheter hub.

Clause 10. The catheter assembly according to clause 1, further comprising an annular plate disposed between the first and second clamping segments of the spring member and the proximal facing surface of the main body of the plug.

Clause 11. The catheter assembly according to clause 10, wherein the first and second clamping segments of the spring member abut a proximal facing surface of the annular plate.

Clause 12. The catheter assembly according to clause 11, wherein the main body of the plug is made of a first material having a first durometer and the annular plate is made of a second material having a second durometer that is greater than the first durometer.

Clause 13. The catheter assembly according to clause 11, wherein the proximal facing surface of the annular plate has a first surface roughness and the proximally facing surface of the main body of the plug has a second surface roughness that is greater than the first surface roughness.

Clause 14. The catheter assembly according to clause 12, wherein the proximal facing surface of the annular plate has a first surface roughness and the proximally facing surface of the main body of the plug has a second surface roughness that is greater than the first surface roughness.

Clause 15. The catheter assembly according to clause 1, wherein the outer wall of the distal part of the actuator includes an indentation in which the first and second clamping segments of the spring member reside when the actuator is in the first axial position, the indentation configured to assist in holding the first and second clamping segments on the distal part of the actuator.

Clause 16. The catheter assembly according to clause 1, further comprising a ferrule positioned between the distal wall of the catheter hub and the distal facing surface of the main body of the plug.

Clause 17. The catheter assembly according to clause 16, further comprising an elongate tube having a proximal end and a distal end, the proximal end being secured to the ferrule.

Clause 18. The catheter assembly according to clause 1, further comprising an introducer needle having a proximal end portion, a sharpened distal tip and a shaft extending between the proximal end and the sharpened distal tip, the shaft extending through the axial through opening the plug and the axial through opening of the actuator when the actuator is in the second axial position.

Clause 19. The catheter assembly according to clause 18, further comprising an elongate catheter tube having a proximal end, a distal end and an inner lumen extending through and between the proximal and distal ends, the proximal end of the catheter tube being coupled to a distal end portion of the catheter hub, the shaft of the introducer needle extending through the inner lumen of the catheter tube.

Clause 20. The catheter assembly according to clause 18, wherein the proximal end portion of the introducer needle is coupled to a needle hub, the needle hub being detachably coupled to a proximal end of the catheter hub.

Clause 21. The catheter assembly according to clause 20, wherein the needle hub has a distally facing surface that presses against the proximal facing surface of the proximal flange of the actuator to cause the actuator to transition from the first axial position to the second axial position Clause 22. The catheter assembly according to clause 18, wherein the shaft of the introducer needle has a first diameter and the inner diameter of the axial through opening extending through the proximal end portion of tubular part of the plug having a second diameter dimension, the first diameter dimension being no more than 20% greater than the second diameter dimension.

Clause 23. The catheter assembly according to clause 1, wherein the proximal facing surface of the main body of the plug has applied thereto a lubricious film, the first and second clamping segments of the spring member being positioned on a surface of the lubricious film.

Clause 24. The catheter assembly according to clause 20, wherein the sharpened distal tip of the introducer needle is retractable into the needle hub.

Clause 25. The catheter assembly according to clause 20, further comprising a needle guard disposed between the distally facing surface of the needle hub and the proximal flange of the actuator.

Clause 26. The catheter assembly according to clause 25, wherein the needle guard has a distally facing surface that presses against the proximal facing surface of the proximal flange of the actuator to cause the actuator to transition from the first axial position to the second axial position.

Group E Clauses:

Clause 1. An assembly comprising:
a hub having a proximal opening, a distal opening and an internal cavity disposed between the proximal and distal openings, the cavity defined by one or more sidewalls and a bottom wall of the hub, the distal opening extending through the bottom wall:
a catheter tube secured to a distal end of the hub and having an inner lumen in fluid communication with the distal opening of the hub;
a valve located inside the hub, the valve including a proximal flange, a distal flange and a tubular part extending between the proximal and distal flanges, the valve being configured to assume an open position and closed position, the valve being made of a resilient material and constructed such that the valve is continuously urged toward the closed position, in the open position fluid flow is permitted through an opening that extends through the proximal and distal flanges and the tubular part, in the closed position fluid flow is impeded through the opening, the valve being constructed such that when a distally applied force is applied to a proximal face of the proximal flange the valve transitions from the closed position to the open position and subsequently returns to the closed position when the distally applied force is removed.

Clause 2. The assembly according to clause 1, wherein a distal face of the distal flange abuts the bottom wall of the hub.

Clause 3. The assembly according to clause 2, wherein the distal flange includes an opening that communicates the tubular part of the valve with the catheter tube when the valve is in the open position and in the closed position.

Clause 4. The assembly according to clause 1, wherein the proximal face of the proximal flange is arranged at a first angle with respect to a longitudinal axis of the hub when the valve is in the open position and is arranged at a second angle with respect to the longitudinal axis of the hub when the valve is in the closed position, the first angle being greater than the second angle.

Clause 5. The assembly according to clause 1, wherein the distal flange has a circumferential surface that presses against the one or more sidewalls of the hub to hold the valve securely inside the cavity of the hub.

Clause 6. The assembly according to clause 1, wherein the distal flange has a circumferential surface that presses against the one or more sidewalls of the hub to hold the valve securely inside the cavity of the hub without the use of an adhesive.

Clause 7. The assembly according to clause 1, wherein the proximal flange has a first diameter when the valve is in the open position and a second diameter when the valve is in the closed position, the first diameter being greater than the second diameter.

Clause 8. The assembly according to clause 1, wherein the tubular part of the valve has walls that press against one another to impede fluid flow through the tubular part when the valve is in the closed position and the walls do not press against one another to permit fluid flow through the tubular part when the valve is in the open position.

Clause 9. An assembly comprising:
a hub having a proximal opening, a distal opening and an internal cavity disposed between the proximal and distal openings, the cavity defined by one or more sidewalls and a bottom wall of the hub, the distal opening extending through the bottom wall:
a catheter tube secured to a distal end of the hub and having an inner lumen in fluid communication with the distal opening of the hub;
an introducer needle residing in the catheter tube and having an outer wall and a distal tip, the distal tip extending distally from a distal end of the catheter tube,
a valve disposed about the introducer needle inside the hub, the valve including a proximal flange, a distal flange and a tubular part extending between the proximal and distal flanges, the valve being configured to assume an open position and a closed position, in the open position a through passage is provided that extends through the proximal and distal flanges and the tubular part, in the closed position the through passage is closed, the valve being made of a resilient material and constructed such that the valve is continuously urged toward the closed position, when the introducer needle resides inside the catheter tube the outer wall of the introducer needle causes the valve to assume the open position, when the introducer needle is removed from the catheter tube the valve assumes the closed position, when the valve is in the closed position the valve is constructed such that when a distally applied force is applied to a proximal face of the proximal flange the valve transitions from the closed position to the open position and subsequently returns to the closed position when the distally applied force is removed.

Group F Clauses:

Clause 1. An assembly comprising:
a hub having a proximal opening, a distal opening and an internal cavity disposed between the proximal and distal openings, the cavity defined by one or more sidewalls and a bottom wall of the hub, the distal opening extending through the bottom wall;
a catheter tube secured to a distal end of the hub and having a tubular wall with an inner surface that defines an inner lumen, the catheter tube having a proximal portion that resides inside the cavity of the hub and a distal portion that resides outside the hub, the proximal portion having an outer surface;

a valve located inside the hub that is transitional between an open position and a closed position, the valve including a base having a through opening through which a portion of the catheter tube passes, the valve including first and second arms that are positioned about the outer surface of the proximal portion of the catheter tube, each of the first and second arms including a first section having a distal end and a proximal end, the distal end of the first section being coupled to the base, the proximal end of the first section being disposed radially inward of the distal end of the first section, each of the first and second arms including a second section having a distal end and a proximal end, the distal end of the second section being coupled to the distal end of the first section, the proximal end of the second section being disposed radially outward of the distal end of the section, the proximal end of the first section of the first arm being coupled to the distal end of the second section of the first arm at a first location, the proximal end of the first section of the second arm being coupled to the distal end of the second section of the second arm at a second location, each of the first and second arms being made of a resilient material and constructed such that the first and second locations are continuously urged toward one another to position the valve in the closed position, in the closed position of the valve the first and second locations press against the outer surface of the proximal portion of the catheter tube to cause a collapse of the tubular wall in the proximal portion that results in a full or substantially full closing of the inner lumen of the catheter tube, in the open position of the valve the first and second locations are positioned radially apart from one another so as not to press against the outer surface of the proximal portion of the catheter tube that results in a full or substantially full opening.

What is claimed is:

1. An intravenous catheter comprising:
    a catheter hub that has a proximal opening, a distal opening and an internal cavity disposed between the proximal and distal openings, the internal cavity defined by one or more sidewalls and a distal wall of the catheter hub, the distal opening extending through the distal wall;
    a plug made of a resilient material, the plug including a main body having a proximal facing surface and a distal facing surface, the main body including an axial through opening and being configured such that the axial through opening is in fluid communication with the distal opening of the catheter hub, the axial through opening extending through a tubular part that has a proximal end portion that protrudes proximal to the proximal facing surface of the main body, there existing a recess in the proximal facing surface that at least partially surrounds the tubular part;
    an actuator including a proximal flange having a proximal facing surface, the actuator including a distally protruding structure that extends distal to the proximal flange, there being an axial through opening that extends through the proximal flange and the distally protruding structure, the distally protruding structure having a proximal part, a distal part and a transverse through opening disposed between the proximal and distal parts, the distal part having an outer wall, the proximal end portion of the tubular part of the plug residing inside the distally protruding structure; and
    a spring member including a proximal end segment and first and second clamping segments that are operatively coupled to the proximal end segment respectively by first and second arms, the spring member being configured to cause the first and second clamping segments to move radially apart from one another when a distally applied force is applied to the proximal end segment, when the actuator is in a first axial position the first and second clamping segments are urged against the outer wall of the distal part of the actuator, when the actuator is in a second axial position distal to the first axial position the distal part of the actuator is configured to move distally into the recess in the proximal facing surface of the main body of the plug and the first and second clamping segments of the spring member move radially inward into the transverse through opening of the actuator to act against the proximal end portion of the tubular part of the plug in a manner sufficient to cause a closing of the axial through opening of the plug in the proximal end portion.

2. The catheter assembly according to claim 1, wherein the proximal part of the actuator has an outer wall that tapers distally inward, when the actuator is in the second axial position the actuator is movable distally to a third axial position to cause the tapered outer wall of the first part of the actuator to act on the first and second clamping segments in a manner that results in the first and second clamping segments to move radially outward in a manner sufficient to at least partially open the axial through opening of the plug.

3. The catheter assembly according to claim 1, wherein when the actuator transitions from the first axial position to the second axial position the actuator is incapable of reassuming the first axial position.

4. The catheter assembly according to claim 2, wherein when the actuator transitions from the first axial position to the second axial position the actuator is incapable of reassuming the first axial position.

5. The catheter assembly according to claim 1, wherein the proximal end segment of the spring member abuts a distal facing surface of the proximal flange of the actuator and each of the first and second clamping segments abuts the proximal facing surface of the main body of the plug.

6. The catheter assembly according to claim 1, wherein the proximal flange of the actuator has a first diameter dimension and the distally protruding part of the actuator has a second diameter dimension that is less than the first diameter dimension.

7. The catheter assembly according to claim 1, wherein the axial through opening of the actuator comprises a key-hole shape.

8. The catheter assembly according to claim 1, wherein the distal facing surface of the main body of the plug is configured to abut the distal wall of the catheter hub.

9. The catheter assembly according to claim 1, wherein a press fit exists between the main body of the plug and the one or more sidewalls of the catheter hub.

10. The catheter assembly according to claim 1, further comprising an annular plate disposed between the first and second clamping segments of the spring member and the proximal facing surface of the main body of the plug.

11. The catheter assembly according to claim 10, wherein the first and second clamping segments of the spring member abut a proximal facing surface of the annular plate.

12. The catheter assembly according to claim 11, wherein the main body of the plug is made of a first material having a first durometer and the annular plate is made of a second material having a second durometer that is greater than the first durometer.

13. The catheter assembly according to claim 11, wherein the proximal facing surface of the annular plate has a first surface roughness and the proximally facing surface of the main body of the plug has a second surface roughness that is greater than the first surface roughness.

14. The catheter assembly according to claim 12, wherein the proximal facing surface of the annular plate has a first surface roughness and the proximally facing surface of the main body of the plug has a second surface roughness that is greater than the first surface roughness.

15. The catheter assembly according to claim 1, wherein the outer wall of the distal part of the actuator includes an indentation in which the first and second clamping segments of the spring member reside when the actuator is in the first axial position, the indentation configured to assist in holding the first and second clamping segments on the distal part of the actuator.

16. The catheter assembly according to claim 1, further comprising a ferrule positioned between the distal wall of the catheter hub and the distal facing surface of the main body of the plug.

17. The catheter assembly according to claim 16, further comprising an elongate tube having a proximal end and a distal end, the proximal end being secured to the ferrule.

18. The catheter assembly according to claim 1, further comprising an introducer needle having a proximal end portion, a sharpened distal tip and a shaft extending between the proximal end portion and the sharpened distal tip, the shaft extending through the axial through opening of the plug and the axial through opening of the actuator when the actuator is in the second axial position.

19. The catheter assembly according to claim 18, further comprising an elongate catheter tube having a proximal end, a distal end and an inner lumen extending through and between the proximal and distal ends, the proximal end of the catheter tube being fixed to a distal end portion of the catheter hub, the shaft of the introducer needle extending through the inner lumen of the catheter tube.

20. The catheter assembly according to claim 18, wherein the proximal end portion of the introducer needle is coupled to a needle hub, the needle hub being detachably coupled to a proximal end of the catheter hub.

21. The catheter assembly according to claim 20, wherein the needle hub has a distally facing surface that presses against the proximal facing surface of the proximal flange of the actuator to cause the actuator to transition from the first axial position to the second axial position.

22. The catheter assembly according to claim 18, wherein the shaft of the introducer needle has a first diameter and the inner diameter of the axial through opening extending through the proximal end portion of tubular part of the plug having a second diameter dimension, the first diameter dimension being no more than 20% greater than the second diameter dimension.

23. The catheter assembly according to claim 1, wherein the proximal facing surface of the main body of the plug has applied thereto a lubricious film, the first and second clamping segments of the spring member being positioned on a surface of the lubricious film.

24. The catheter assembly according to claim 20, wherein the sharpened distal tip of the introducer needle is retractable into the needle hub.

25. The catheter assembly according to claim 20, further comprising a needle guard disposed between the distally facing surface of the needle hub and the proximal flange of the actuator.

26. The catheter assembly according to claim 25, wherein the needle guard has a distally facing surface that presses against the proximal facing surface of the proximal flange of the actuator to cause the actuator to transition from the first axial position to the second axial position.

* * * * *